(12) United States Patent
Herr et al.

(10) Patent No.: US 10,155,063 B2
(45) Date of Patent: Dec. 18, 2018

(54) METHODS FOR VAS-OCCLUSIVE CONTRACEPTION AND REVERSAL THEREOF

(71) Applicant: University of Virginia Patent Foundation, Charlottesville, VA (US)

(72) Inventors: John C. Herr, Charlottesville, VA (US); Alexander L. Klibanov, Charlottesville, VA (US); Kevin Simon Eisenfrats, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/349,824

(22) Filed: Nov. 11, 2016

(65) Prior Publication Data

US 2017/0136143 A1   May 18, 2017

Related U.S. Application Data

(60) Provisional application No. 62/254,381, filed on Nov. 12, 2015, provisional application No. 62/369,807, filed on Aug. 2, 2016.

(51) Int. Cl.
*A61F 6/20* (2006.01)
*A61L 24/06* (2006.01)
(Continued)

(52) U.S. Cl.
CPC .............. *A61L 24/06* (2013.01); *A61B 8/085* (2013.01); *A61B 8/0833* (2013.01);
(Continued)

(58) Field of Classification Search
CPC ................ A61B 8/481; A61B 19/5244; A61B 2019/5272; A61B 19/52;
(Continued)

(56) References Cited

U.S. PATENT DOCUMENTS 3,716,056 A   2/1973   Brodsky et al.
4,269,174 A   5/1981   Adair
(Continued)

FOREIGN PATENT DOCUMENTS

CN   103724638 B   12/2015
EP      2233160 A2    9/2010
(Continued)

OTHER PUBLICATIONS

"U.S. Appl. No. 15/349,806, Non Final Office Action dated Feb. 24, 2017", 9 pgs.
(Continued)

*Primary Examiner* — Ophelia A Hawthorne
(74) *Attorney, Agent, or Firm* — Schwegman Lundberg & Woessner, P.A.

(57) ABSTRACT

Disclosed are methods of delivering an agent to the lumen of the vas deferens under guidance of ultrasound imaging. The methods include vas-occlusive contraception in which the vas deferens is non-surgically isolated and an occlusive substance is percutaneously administered into the lumen of the vas deferens under ultrasound. Also disclosed are methods of reversal of vas-occlusive contraception and methods of delivering an agent to the lumen of the vas deferens. Also disclosed are compositions for use in the methods of the invention.

26 Claims, 41 Drawing Sheets

(51) Int. Cl.

| | |
|---|---|
| *A61B 17/34* | (2006.01) |
| *A61F 6/22* | (2006.01) |
| *A61K 49/22* | (2006.01) |
| *A61L 24/00* | (2006.01) |
| *A61B 8/08* | (2006.01) |
| *A61L 27/52* | (2006.01) |
| *A61L 27/54* | (2006.01) |
| *A61B 17/12* | (2006.01) |

(52) U.S. Cl.
CPC ............ *A61B 8/0841* (2013.01); *A61B 17/12* (2013.01); *A61B 17/12022* (2013.01); *A61B 17/12186* (2013.01); *A61B 17/3403* (2013.01); *A61F 6/22* (2013.01); *A61K 49/223* (2013.01); *A61K 49/226* (2013.01); *A61L 24/001* (2013.01); *A61L 24/0015* (2013.01); *A61L 24/0031* (2013.01); *A61L 24/0036* (2013.01); *A61L 27/52* (2013.01); *A61L 27/54* (2013.01); *A61B 8/0891* (2013.01); *A61B 8/481* (2013.01); *A61B 8/488* (2013.01); *A61B 2017/3413* (2013.01); *A61L 2300/626* (2013.01); *A61L 2400/06* (2013.01); *A61L 2430/36* (2013.01)

(58) Field of Classification Search
CPC ...... A61B 2019/5251; A61B 17/12022; A61B 17/12099; A61L 2430/36; A61F 6/225; A61F 6/22; A61F 6/206
See application file for complete search history.

(56) References Cited

U.S. PATENT DOCUMENTS

| | | | |
|---|---|---|---|
| 4,804,691 A | 2/1989 | English et al. | |
| 4,920,982 A | 5/1990 | Goldstein | |
| 4,967,949 A | 11/1990 | Sandhaus | |
| 5,240,997 A | 8/1993 | Yanai et al. | |
| 5,258,042 A | 11/1993 | Mehta | |
| 5,383,896 A | 1/1995 | Gershony et al. | |
| 5,488,075 A | 1/1996 | Guha | |
| 5,612,052 A | 3/1997 | Shalaby | |
| 5,667,767 A | 9/1997 | Greff et al. | |
| 5,695,740 A | 12/1997 | Porter | |
| 5,702,717 A | 12/1997 | Cha et al. | |
| 5,714,159 A | 2/1998 | Shalaby | |
| 5,866,554 A | 2/1999 | Shalaby et al. | |
| 5,947,893 A | 9/1999 | Agrawal et al. | |
| 5,989,580 A * | 11/1999 | Wallace ............... | A61K 9/0039 128/831 |
| 6,037,331 A | 3/2000 | Shalaby et al. | |
| 6,096,052 A | 8/2000 | Callister et al. | |
| 6,103,254 A * | 8/2000 | Wallace ............... | A61K 9/0024 424/418 |
| 6,197,940 B1 | 3/2001 | Klinefelter | |
| 6,224,893 B1 | 5/2001 | Langer et al. | |
| 6,297,337 B1 | 10/2001 | Marchant et al. | |
| 6,413,539 B1 | 7/2002 | Shalaby | |
| 6,432,116 B1 | 8/2002 | Callister et al. | |
| 6,485,426 B2 | 11/2002 | Sandhu | |
| 6,514,534 B1 | 2/2003 | Sawhney | |
| 6,514,535 B2 | 2/2003 | Marchant | |
| 6,531,111 B1 * | 3/2003 | Whalen, II ......... | A61K 49/0002 424/1.65 |
| 6,703,047 B2 | 3/2004 | Sawhney et al. | |
| 6,723,781 B1 | 4/2004 | Frate | |
| 6,756,031 B2 | 6/2004 | Evans et al. | |
| 6,858,219 B2 | 2/2005 | Evans et al. | |
| 7,073,504 B2 | 7/2006 | Callister et al. | |
| 7,160,931 B2 | 1/2007 | Cheng et al. | |
| 7,398,780 B2 | 7/2008 | Callister et al. | |
| 7,694,683 B2 | 4/2010 | Callister et al. | |
| 7,754,212 B2 | 7/2010 | Klinefelter | |
| 7,789,891 B2 | 9/2010 | Wallace | |
| 7,918,863 B2 | 4/2011 | Nguyen et al. | |
| 7,975,697 B2 | 7/2011 | Callister et al. | |
| 8,048,086 B2 * | 11/2011 | Lee-Sepsick ......... | A61B 17/42 424/400 |
| 8,048,101 B2 | 11/2011 | Lee-Sepsick et al. | |
| 8,052,669 B2 * | 11/2011 | Lee-Sepsick .... | A61B 17/12099 424/1.11 |
| 8,113,205 B2 | 2/2012 | Callister et al. | |
| 8,123,693 B2 | 2/2012 | Connor et al. | |
| 8,226,680 B2 | 7/2012 | Wallace et al. | |
| 8,235,047 B2 | 8/2012 | Swann et al. | |
| 8,316,853 B2 | 11/2012 | Lee-Sepsick et al. | |
| 8,316,854 B2 | 11/2012 | Lee-Sepsick et al. | |
| 8,322,341 B2 | 12/2012 | Koeller | |
| 8,324,193 B2 | 12/2012 | Lee-Sepsick et al. | |
| 8,336,552 B2 | 12/2012 | Lee-Sepsick et al. | |
| 8,360,064 B2 | 1/2013 | Swann et al. | |
| 8,434,489 B2 | 5/2013 | Gopal et al. | |
| 8,440,487 B2 | 5/2013 | Furumura | |
| 8,550,085 B2 | 10/2013 | Callister et al. | |
| 8,551,001 B2 | 10/2013 | Connor et al. | |
| 8,603,080 B1 | 12/2013 | Fried et al. | |
| 8,613,282 B2 | 12/2013 | Nikolchev et al. | |
| 8,689,792 B2 | 4/2014 | Jimenez et al. | |
| 8,695,606 B2 | 4/2014 | Lee-Sepsick et al. | |
| 8,726,906 B2 | 5/2014 | Lee-Sepsick et al. | |
| 8,766,853 B2 | 7/2014 | Furumura et al. | |
| 8,933,784 B2 | 1/2015 | Furumura | |
| 9,034,053 B2 | 5/2015 | Lee-Sepsick et al. | |
| 9,220,880 B2 | 12/2015 | Lee-Sepsick et al. | |
| 2002/0051750 A1 | 5/2002 | Schutt et al. | |
| 2002/0106328 A1* | 8/2002 | Johnson ............... | A61K 49/223 424/9.51 |
| 2002/0106411 A1 | 8/2002 | Wironen et al. | |
| 2003/0185758 A1 | 10/2003 | Evans et al. | |
| 2003/0206864 A1 | 11/2003 | Mangin | |
| 2004/0087930 A1 | 5/2004 | Whalen, II et al. | |
| 2004/0240715 A1 | 12/2004 | Wicker et al. | |
| 2005/0045183 A1 | 3/2005 | Callister et al. | |
| 2005/0147599 A1 | 7/2005 | Hunter et al. | |
| 2005/0149117 A1* | 7/2005 | Khosravi ............ | A61B 17/00491 606/215 |
| 2005/0192616 A1 | 9/2005 | Callister et al. | |
| 2005/0266086 A1 | 12/2005 | Sawhney | |
| 2005/0283098 A1 | 12/2005 | Conston et al. | |
| 2006/0222596 A1 | 10/2006 | Askari et al. | |
| 2006/0241452 A1 | 10/2006 | Cerofolini | |
| 2007/0060906 A1 | 3/2007 | Wu | |
| 2008/0039890 A1* | 2/2008 | Matson ............... | A61L 24/0036 606/200 |
| 2008/0045865 A1 | 2/2008 | Kislev | |
| 2008/0308110 A1 | 12/2008 | Callister et al. | |
| 2009/0024155 A1 | 1/2009 | Lee-sepsick et al. | |
| 2009/0053276 A1 | 2/2009 | Richard | |
| 2009/0277457 A1 | 11/2009 | Hoey et al. | |
| 2010/0003297 A1 | 1/2010 | Tobias et al. | |
| 2010/0063392 A1 | 3/2010 | Nishina et al. | |
| 2010/0089406 A1 | 4/2010 | Kachiguina | |
| 2010/0158813 A1 | 6/2010 | Paradossi et al. | |
| 2011/0065809 A1 | 3/2011 | Benz et al. | |
| 2011/0137150 A1 | 6/2011 | Connor et al. | |
| 2011/0165114 A1 | 7/2011 | McCoy et al. | |
| 2012/0192872 A1* | 8/2012 | Rudakov ............. | A61B 17/12036 128/831 |
| 2014/0046182 A1 | 2/2014 | Connor et al. | |
| 2014/0128497 A1 | 5/2014 | Ladet et al. | |
| 2014/0261446 A1* | 9/2014 | Sjoquist ................ | A61F 6/206 128/843 |
| 2015/0068531 A1 | 3/2015 | Lee-Sepsick et al. | |
| 2015/0136144 A1* | 5/2015 | DePinto ............... | A61F 6/20 128/843 |
| 2016/0024326 A1 | 1/2016 | Khan et al. | |
| 2016/0193392 A1 | 7/2016 | Askari et al. | |

(56) References Cited

U.S. PATENT DOCUMENTS

| | | | |
|---|---|---|---|
| 2017/0136144 A1 | 5/2017 | Herr et al. | |
| 2017/0189581 A1 | 7/2017 | Desai et al. | |

FOREIGN PATENT DOCUMENTS

| | | |
|---|---|---|
| WO | WO-2017174071 A1 | 10/2007 |
| WO | WO-2008115694 A2 | 9/2008 |
| WO | WO-2012112417 A2 | 8/2012 |
| WO | WO-2017044983 A1 | 3/2017 |
| WO | WO-2017083753 A1 | 5/2017 |

OTHER PUBLICATIONS

"Co-pending U.S. Appl. No. 15/349,806, filed Nov. 11, 2016", 137 pgs.

"International Application Serial No. PCT/US2016/061671, International Search Report dated Mar. 17, 2017", 5 pgs.

"International Application Serial No. PCT/US2016/061671, Invitation to Pay Additional Fees and Partial Search Report dated Jan. 10, 2017".

"International Application Serial No. PCT/US2016/061671, Written Opinion dated Mar. 17, 2017", 24 pgs.

"Sigma-Aldrich Product Safety Data Sheet", Sigma-Aldrich Corporation "poly(vinyl alcohol coethylene) with ethylene 32 mol %" Product No. 414093, Version 4.2, (Print Date: Mar. 27, 2017), 6 pgs.

Abdala, N., et al., "Use of Ethylene Vinyl Alcohol Copolymer for Tubal Sterilization by Selective Catheterization in Rabbits", Journal of Vascular and Interventional Radiology,12(8):, (2001), 979-984.

Attaran, Robert R., et al., "Protocol for Optimal Detection and Exclusion of a Patent Foramen Ovale Using Transthoracic Echocardiography with Agitated Saline Microbubbles", Echocardiography (Mount Kisco, N.Y.), 23(7), (2006), 616-622.

Bank, Alan J, et al., "Contribution of Collagen, Elastin, and Smooth Muscle to In Vivo Human Brachial Artery Wall Stress and Elastic Modulus", Circulation 1996;94, (Jan. 1997), 23 pgs.

Calliada, Fabrizio, et al., "Ultrasound contrast agents: basic principles", Eur J Radiol 27 Suppl 2, (1998), 4.

Chaki, S P, et al., "A short-term evaluation of semen and accessory sex gland function in phase III trial subjects receiving intranasal contraceptive RISUG", Contraception, 67(1), (2003), 73-78.

Clenney, Timothy L, et al., "Vasectomy Techniques", Am Fam Physician. 60(1):, (1999), 9 pgs.

Cosgrove, David, "Ultrasound contrast agents: An overview", Radiology vol. 60, Issue 3, (2006), 324-330.

El-Sherif, Dalia M, et al., "Development of a novel method for synthesis of a polymeric ultrasound contrast agent", Journal of Biomedical Materials Research Part A, 66A(2),, (2003), 347-355.

Flickinger, Charles J, "Alterations in the fine structure of the rat epididymis after vasectomy", Anat Rec, 1972. 173(3), (1972), 277-299.

Flickinger, Charles J, et al., "The influence of vasovasostomy on testicular alterations after vasectomy in lewis rats", Anat Rec 217(2)., (1987), 137-145.

Flickinger, Charles J, "Ultrastructure of the rat testis after vasectomy", Anat Rec 174(4), (1972), 477-493.

Guha, Sujoy K, et al., "Phase II Clinical Trial of a Vas Deferens Injectable Contraceptive for the Male Contraception", Elsevier Science Inc. 56:4, (1997), 245-250.

Hafez, E S, et al., "Atlas of Human Reproduction: By Scanning Electron Microscopy", 982, MTP Press, Hingham, MA. Part 1-1 (separated into 4 parts for Filing), (1982), 85 pgs.

Hafez, E. S., et al., "Atlas of Human Reproduction: By Scanning Electron Microscopy", 982, MTP Press, Hingham, MA. Part 1-2 (separated into 4 parts for Filing), (1982), 85 pgs.

Hafez, E. S., et al., "Atlas of Human Reproduction: By Scanning Electron Microscopy", 982, MTP Press, Hingham, MA. Part 2-1 (separated into 4 parts for Filing), (1982), 66 pgs.

Hafez, E. S., et al., "Atlas of Human Reproduction: By Scanning Electron Microscopy", 982, MTP Press, Hingham, MA. Part 2-2 (separated into 4 parts for Filing), (1982), 101 pgs.

Jha, Rakhi K, et al., "Smart RISUG: A potential new contraceptive and its magnetic field-mediated sperm interaction", International Journal of Nanomedicine 4, (2009), 55-64.

Koul, Veena, et al., "Reversibility With Sodium Bicarbonate of Styrene Maleic Anhydride, an Intravasal Injectable Contraceptive, in Male Rats", Elsevier Science Inc. Contraception 58(4), (1998), 227-231.

Liu, Xiaozhang, et al., "The Relationship Between the Vas Volume and the Anatomic Size of the Vas Deferens", Elsevier Science Inc. Contraception, 56(6), (1997), 391-394.

Lohiya, N K, et al., "RISUG: An intravasal injectable male contraceptive", Indian J Med Res 140 (Supplement), (2017), 63-72.

Lohiya, Nirmal K, et al., "Preclinical evaluation for noninvasive reversal following long-term vas occlusion with styrene maleic anhydride in langur monkeys", Contraception 71(3), (2005), 214-226.

Middleton, William D, et al., "High-Resolution Sonography of the Normal Extrapelvic Vas Deferens", J Ultrasound Med., 28(7), (2009), 839-46.

Naughton, Cathy K, et al., "The Use of URYX for Reversible Vasectomy in a Rabbit Model", Journal of Andrology, 25, (2004), 545-553.

Reddy, Neena M, et al., "Vasectomy-Related Changes on Sonographic Examination of the Scrotum", J. Clin. Ultrasound 32, (2004), 394-398.

Robinette, William B., "Ultrasound Contrast Agents", JDMS 13:29S-34S, (1997), 29S-34S.

Roy, Sohini, et al., "Polyelectrolyte polymer properties in relation to male contraceptive RISUG® action", Colloids and Surfaces B: Biointerfaces 69, (2009), 77-84.

Soebadi, D M, et al., "Intravasal injection of formed-in-place medical grade silicone for vas occlusion", International Journal of Andrology 18, (1995), 45-52.

Stockton, D M, et al., "No-scalpel vasectomy: a technique for family physicians", Am Fam Physician 46 1153-67, (1992), 19 pgs.

Szabo, Thomas L, et al., "Ultrasound Transducer Selection in Clinical Imaging Practice", Journal of Ultrasound in Medicine 32(4), (2013), 573-582.

Waller, Donald, et al, "Azoospermia in rabbits following an intravas injection of Vasalgel", Basic and Clinical Andrology, 26:6 (2016)., (2016), 1-8.

Zambon, J V, et al., "Efficacy of percutaneous vas occlusion compared with conventional vasectomy", BJU International 86, (2000), 699-706.

Zhao, Sheng Cai, et al., "Intravasal injection of formed-in-place silcone rubber as a method of vas occlusion", International Journal of Andrology 15, (1992), 460-464.

Zhao, Sheng Cai, "Vas Deferens Occlusion by Percutaneous Injection of Polyurethane Elastomer Plugs: Clinical Experience and Reversibility", Shanxi Provincial People's Hospital, Taiyuan, People's Republic of China 41(5), (1990), 453-459.

"U.S. Appl. No. 15/349,806, Non Final Office Action dated Aug. 22, 2017", 14 pgs.

"U.S. Appl. No. 15/349,806, Response filed May 23, 2017 to Non Final Office Action dated Feb. 24, 2017", 14 pgs.

McKay, Craig S., et al., "Click Chemistry in Complex Mixtures: Bioorthogonal Bioconjugation", Chem Biol. Sep. 18, 2014; 21(9): 1075-1101. doi:10.1016/j.chembiol.2014.09.002., (2014), 51 pgs.

"International Application Serial No. PCT/US2016/061671, International Preliminary Report on Patentability dated May 24, 2018", 26 pgs.

"U.S. Appl. No. 15/863,759 Non-Final Office Action dated Apr. 3, 2018", New River Valley IP, Contraline, (Apr. 3, 2018), 11 pages.

* cited by examiner

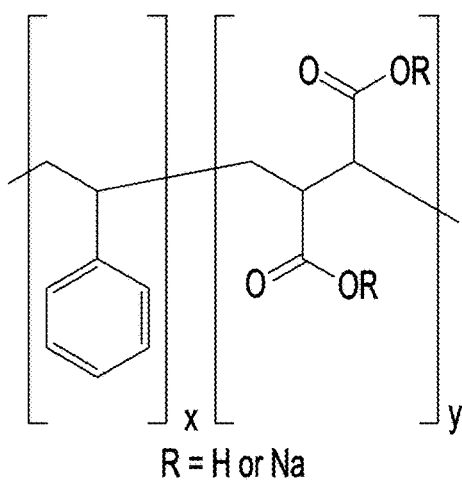
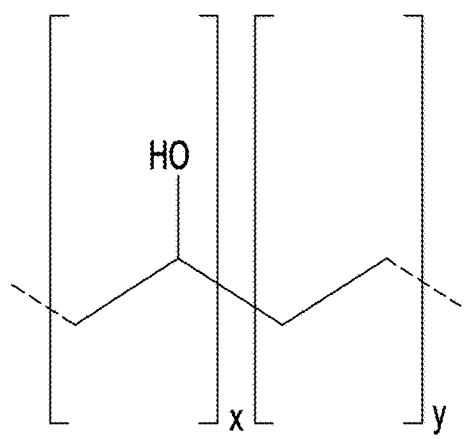
FIG. 15A
FIG. 15B

GROUP A: EVOH
GROUP B: SMA
GROUP C: NEGATIVE CONTROL

| TREATMENTS PAIR | TUKEY HSD Q STATISTIC | TUKEY HSD p-VALUE | TUKEY HSD INFERFENCE |
|---|---|---|---|
| A vs B | 22.4164 | 0.0010053 | **p<0.01 |
| A vs C | 3.1174 | 0.0762742 | INSIGNIFICANT |
| B vs C | 15.1801 | 0.0010053 | **p<0.01 |

TUKEY RESULTS: COMPARING EVOH WT% (5%, 10%, 15%, 20%)
GROUP A: ALL 5% EVOH
GROUP B: ALL 10% EVOH
GROUP C: ALL 15% EVOH
GROUP D: ALL 20% EVOH
GROUP E: CONTROL

| TREATMENTS PAIR | TUKEY HSD Q STATISTIC | TUKEY HSD p-VALUE | TUKEY HSD INFERFENCE |
|---|---|---|---|
| A vs B | 9.0516 | 0.0010053 | **p<0.01 |
| A vs C | 7.4023 | 0.0010053 | **p<0.01 |
| A vs D | 5.4861 | 0.0020664 | **p<0.01 |
| A vs E | 7.5697 | 0.0010053 | **p<0.01 |
| B vs C | 1.6493 | 0.7442152 | INSIGNIFICANT |
| B vs D | 3.5655 | 0.0970243 | INSIGNIFICANT |
| B vs E | 1.1693 | 0.8999947 | INSIGNIFICANT |
| C vs D | 1.9163 | 0.6386164 | INSIGNIFICANT |
| C vs E | 2.3355 | 0.4711142 | INSIGNIFICANT |
| D vs E | 3.6905 | 0.0792642 | INSIGNIFICANT |

FIG. 22

| NELSON LABS, NON-GLP CYTOTOXICITY (MEM ELUTION) | | | |
|---|---|---|---|
| ID | POLYMER SOLUTION | SCORE | RESULT |
| 1 | EVOH-32 10% | 0 | PASS |
| 2 | EVOH-32 15% | 0 | PASS |
| 3 | EVOH-38 15% | 0 | PASS |

FIG. 23

|  | INNER DIAMETER (DILATED) | INJECTION VOLUME OF OCCLUSIVE AGENT |
| --- | --- | --- |
| LARGE SIZE | 1.6-1.8 mm | 150-190 µL |
| MEDIUM SIZE | 1.4-1.6 mm | 120-150 µL |
| SMALL SIZE | 1.2-1.4 mm | 90-120 µL |

FIG. 28

| POLYMER CANDIDATE | SURFACE AREA ($m^2/g$) | PORE VOLUME ($m^3/g$) | PORE DIAMETER (nm) |
| --- | --- | --- | --- |
| EVOH-32, 10% | 32.24 | $2.8*10^{\wedge}(-8)$ | 3.474 |
| EVOH-32, 15% | 20.875 | $1.2*10^{\wedge}(-10)$ | 0.0229 |
| EVOH-32, 20% | 148.72 | $5.9*10^{\wedge}(-10)$ | 0.0158 |
| SMA, 20% | 21.6 | $1.3*10^{\wedge}(-7)$ | 24.07 |
| SMA, 25% | 8.743 | $1.7*10^{\wedge}(-7)$ | 80.52 |

FIG. 29

| FORMULATIONS | HARDNESS (kPa) | ELASTIC MODULUS (kPa) |
|---|---|---|
| EVOH-32, 10% | 0.61 | 3.546666667 |
| EVOH-32, 15% | 3.54 | 54.78 |
| EVOH-32, 20% | 26.65 | 219.93 |
| SMA, 25% | 10.92 | 185.4325 |

| SOURCE | SUM OF SQUARES SS | DEGREES OF FREEDOM | MEAN SQUARES SS | F-STATISTIC | p-VALUE |
|---|---|---|---|---|---|
| TREATMENT | 21,536.2105 | 5 | 4307.2421 | 172.0666 | 1.1102e-16 |
| ERROR | 801.0371 | 32 | 25.0324 | | |
| TOTAL | 22,337.2476 | 37 | | | |

FIG. 34A

| COMPARISON GROUPS | TUKEY STATISTIC | INFERENCE |
|---|---|---|
| INITIAL V. DMSO (NEGATIVE CONTROL) | $p<0.01$ | DMSO SIGNIFICANTLY DECREASED SPERM MOTILITY |
| INITIAL V. ALL EVOH POLYMERS | $p<0.01$ | EVOH POLYMERS SIGNIFICANTLY DECREASED SPERM MOTILITY |
| INITIAL V. SMA POLYMERS | $p<0.01$ | SMA POLYMERS SIGNIFICANTLY DECREASED SPERM MOTILITY |
| DMSO VS. ALL EVOH POLYMERS | $p<0.01$ | EVOH POLYMERS SIGNIFICANTLY DECREASED SPERM MOTILITY |
| DMSO VS. ALL SMA POLYMERS | $p<0.01$ | SMA POLYMERS SIGNIFICANTLY DECREASED SPERM MOTILITY |
| EVOH POLYMERS VS. SMA POLYMERS | $p<0.01$ | THERE WAS NO SIGNIFICANT DIFFERENCE IN SPERM MOTILITY BETWEEN SMA AND EVOH |

FIG. 34B

| SOURCE | SUM OF SQUARES SS | DEGREES OF FREEDOM | MEAN SQUARES SS | F-STATISTIC | p-VALUE |
|---|---|---|---|---|---|
| TREATMENT | 27,822.5264 | 5 | 5,564.5053 | 142.7883 | 1.1102e-16 |
| ERROR | 1,013.2283 | 26 | 38.9703 | | |
| TOTAL | 28,835.7547 | 31 | | | |

FIG. 36A

| COMPARISON GROUPS | TUKEY STATISTIC | INFERENCE |
|---|---|---|
| INITIAL V. DMSO (NEGATIVE CONTROL) | $p<0.01$ | INCUBATION WITH DMSO SIGNIFICANTLY DECREASED SPERM VIABILITY |
| INITIAL V. ALL EVOH POLYMERS | $p<0.01$ | INCUBATION WITH EVOH POLYMERS SIGNIFICANTLY DECREASED SPERM VIABILITY |
| INITIAL V. SMA POLYMERS | $p<0.01$ | INCUBATION WITH SMA POLYMERS SIGNIFICANTLY DECREASED SPERM VIABILITY |
| DMSO VS. ALL EVOH POLYMERS | $p<0.01$ | INCUBATION WITH EVOH POLYMERS SIGNIFICANTLY DECREASED SPERM VIABILITY |
| DMSO VS. ALL SMA POLYMERS | $p<0.01$ | INCUBATION WITH SMA POLYMERS SIGNIFICANTLY DECREASED SPERM VIABILITY |
| EVOH POLYMERS VS. SMA POLYMERS | $p<0.01$ | INCUBATION WITH SMA POLYMERS DID NOT SIGNIFICANTLY DECREASED SPERM VIABILITY |

FIG. 36B

METHODS FOR VAS-OCCLUSIVE CONTRACEPTION AND REVERSAL THEREOF

CROSS-REFERENCE TO RELATED APPLICATIONS

This application relies on the disclosure of and claims priority to and the benefit of the filing date of U.S. Provisional Application No. 62/254,381, filed on Nov. 12, 2015 and U.S. Provisional Application No. 62/369,807, filed on Aug. 2, 2016, the disclosures of each of which are hereby incorporated by reference herein in their entireties.

BACKGROUND OF THE INVENTION

Field of the Invention

The present invention is generally directed to the field of urology. More particularly, the present invention is directed to the field of male contraception. Even more particularly, the present invention is directed to methods and compositions for male contraception by way of percutaneous administration of one or more occlusive substance into the vas deferens. The methods are advantageously performed under the guidance of an imaging modality, such as ultrasound imaging, to ensure placement of the occlusive substance into the lumen of the vas deferens. Also disclosed are methods of reversal of the male contraception. Also disclosed are compositions of occlusive substances that are visible by way of ultrasound imaging and other types of imaging.

Description of Related Art

Vasectomy is a procedure for producing male contraception which involves severing the vas deferens. Potential complications of vasectomy include bleeding at the site of the surgical procedure, which may cause swelling or bruising; infection at the site of the incision; infection in the scrotum; sperm granuloma; congestive epididymitis; recanalization; and the inability to reverse the vasectomy. Additionally, a portion of patients report pain after the procedure. Possibly the largest deterring factor of vasectomy, besides the surgical nature of the procedure, is the difficulty of reversing the vasectomy. The procedure, known as vasovasostomy, is a three to four hour long, expensive microsurgical procedure in which the patient is under general anesthesia. Further, a vasovasostomy also does not guarantee the man restores his fertility due to the presence of anti-sperm antibodies that persist in the body after the vasovasostomy.

Due to these potential complications and difficulty in reversing the procedure, alternative procedures for long-lasting male contraception have been explored. One strategy that has been the subject of research and development is vas-occlusive contraception, which involves injecting or implanting a substance into the vas deferens lumen to occlude this vessel so that the flow of sperm cells from the epididymis is blocked. Particular examples include RISUG, which involves implantation of styrene maleic anhydride, VASALGEL, which involves implantation of styrene maleic acid, as well as polyurethane and silicone implants. However, technical barriers for successfully introducing these procedures into the male contraceptive armamentarium have been documented.

Examples of related efforts include those described in U.S. Pat. Nos. 5,488,075; 5,667,767; 6,103,254; 6,858,219; 6,756,031; 8,551,001; 8,123,693; 8,613,282; 8,689,792; 8,550,085; 8,434,489; 8,113,205 7,975,697; 7,694,683; 7,398,780; 7,073,504; 6,432,116; 6,096,052; 8,360,064; 9,034,053; 8,322,341; 8,235,047; 7,918,863; 7,694,683; 8,048,086; 9,220,880; 9,034,053; 8,726,906; 8,695,606; 8,336,552; 8,324,193; 8,316,854; 8,316,853; 8,052,669; 8,048,101; 8,048,086; 8,226,680; 7,789,891; 4,920,982; 8,603,080; 4,269,174; 6,485,426; 8,316,854; and 8,551,001; as well as U.S. Patent Application Publication Nos. 2005/0045183; 2015/0068531; 2015/0136144; 2008/0308110; 2005/0192616; 2010/0063392; and 2004/0240715. Additional related efforts include the following: Reddy, N. M., et al., *J. Clin. Ultrasound*, 32: 394-398 (2004); Abdala, N. et al., *Journal of Vascular and Interventional Radiology*, 12(8): 979-984 (2001); Zhao, S. C., *Contraception*, 41(5):453-459 (1990); Guha, S. K. et al., *Contraception*, 56:4, 245-250 (1997); Chaki, S. P. et al., *Contraception*, 67(1):73-78 (2003); Lohiya, N. K. et al., *Contraception*, 71(3):214-226 (2005); Liu, X. et al., *Contraception*, 56(6): 391-394 (1997) ("Liu, X. et al."); Koul, V. et al., *Contraception* 58(4):227-31 (1998); Lohiya, N. K., et al., *Indian J Med Res* 140 (Supplement): 63-72 (2014); Roy, S. et al., *Colloids and Surfaces B: Biointerfaces* 69: 77-84 (2009); Zhao, S. C., *International Journal of Andrology*, 15:460-464 (1992); Soebadi, D. M., *International Journal of Andrology*, 18: 45-52 (1995); Jha, R. K., et al., *International Journal of Nanomedicine*, 4:55-64 (2009); Middleton, W. D., et al., *J Ultrasound Med.*, 28(7):839-46 (2009); Naughton, C. K., et al., *Journal of Andrology*, 25: 545-553 (2004); Waller et al., *Basic and Clinical Andrology*, 26:6 (2016); and Zambon, J. V., *BJU International*, 86, 699-706 (2000). Yet, despite these efforts, there remains a need in the art for an improved method of male contraception that can be made available to men in need of a safe, effective, and easily administered reversible contraceptive.

SUMMARY OF THE INVENTION

According to embodiments, the present invention provides a method which includes non-surgically or surgically isolating the vas deferens of a subject, placing an ultrasound probe on or near the vas deferens and administering ultrasonic energy to image a lumen portion of the vas deferens. Any aspect of the methods can be performed surgically, non-surgically, or a combination of non-surgically and surgically. A needle or catheter or portion thereof can be placed into the lumen portion of the vas deferens, such as percutaneously and/or optionally under guidance of ultrasound imaging, and a substance is administered into the lumen portion of the vas deferens through the needle or catheter. In various embodiments, the methods encompass any therapeutic or diagnostic application of administering a substance into the vas deferens, optionally under ultrasound imaging.

In more particular embodiments, the present invention provides a method of vas-occlusive contraception involving non-surgical or surgical isolation of the vas deferens and administration of an occlusive substance into the lumen of the vas deferens. In some embodiments, the substance administered into the lumen of the vas deferens is a polymer (i.e. vas-occlusive polymer), such as a substance capable of forming a polymer or mass, or a combination of substances capable of forming a polymer or mass when combined. According to embodiments, the entire procedure, or one or more portions of the procedure, is guided by way of an imaging modality, such as ultrasound imaging. According to embodiments, the polymer or substance can be administered as a solution and form an occlusion or mass in the lumen of the vas deferens in situ. Formation of the occlusion or mass can take place in whole or in part in the lumen. The polymer or substance can be echogenic such that it can be visualized by way of an imaging modality, such as ultrasound imaging.

In embodiments, the method includes non-surgically or surgically isolating the vas deferens and placing an ultrasound probe on or near the vas deferens. In some embodiments, the method further includes applying ultrasonic energy and visually identifying the vas-deferens by way of ultrasound imaging prior to, during, or after administering the occlusive substance. In some embodiments, the method further includes applying ultrasonic energy and determining an inner (i.e. lumen) diameter, outer diameter, and length of the vas deferens by way of ultrasound imaging prior to, during, or after administering the occlusive substance. In some embodiments, the method further includes applying ultrasonic energy and identifying the lumen of the vas deferens by way of ultrasound imaging prior to, during, or after administering the occlusive substance. In some embodiments, the method further includes applying ultrasonic energy and visually confirming placement of a needle or catheter or a portion thereof into the lumen of the vas-deferens by way of ultrasound imaging prior to, during, or after administering the occlusive substance. In some embodiments, the method further includes applying ultrasonic energy and visually confirming placement of the occlusive substance in the lumen of the vas deferens by way of ultrasound imaging. In some embodiments, when the occlusive substance is a polymer, such as a substance capable of forming a polymer or mass, or a combination of substances capable of forming a polymer or mass when combined, the method further includes applying ultrasonic energy and monitoring of polymerization of the echogenic vas-occlusive polymer in real time by way of ultrasound imaging. In some embodiments, the method further includes determining one or more dimensions of an occlusion formed by the administered substance inside the lumen of the vas deferens by way of ultrasound imaging.

According to embodiments, the non-surgical or surgical isolation of the vas deferens optionally includes use of the "three-finger technique" to isolate the vas deferens close to the scrotal skin. According to other embodiments, the non-surgical or surgical isolation of the vas deferens alternatively or in addition includes use of a vas-fixation clamp to grip the vas deferens through the skin of the scrotum. In some embodiments, a combination of these techniques is used. Once isolated and secured beneath the scrotal skin, an occlusive substance such as a vas-occlusive polymer (including a substance capable of forming a polymer or mass, or a combination of substances capable of forming a polymer or mass when combined) can be administered into the vas deferens by way of any technique now or later available in the field, such as by way of percutaneous injection or controlled intra-vasal infusion.

According to embodiments, the vas-occlusive polymer, or substance(s) capable of forming a polymer, copolymer, or block copolymer, is first dissolved in a solvent prior to administration into the vas deferens. Not wishing to be bound by any particular theory, it is believed that dissipation of the solvent in the aqueous environment of the vas deferens lumen and/or uptake via epithelial cells causes the polymer to polymerize in situ, or otherwise form as mass thereby eventually forming an occlusion inside the lumen.

According to some embodiments, the occlusive substance such as a vas-occlusive polymer is innately echogenic. In some embodiments, the vas-occlusive polymer is echogenic due to the presence of microbubbles present in the polymer solution. In other embodiments, the vas-occlusive polymer is echogenic due to other constituents present in the polymer solution.

Embodiments of the invention additionally provide for the use of ultrasonic imaging to confirm placement of the occlusive substance into the vas deferens lumen, determine location of the occlusion, one or more dimensions of the occlusion such as length and diameter, as well as monitor the long-term stability of the occlusion in the vas deferens.

According to another embodiment of the invention, a method of reversal of occluding a body lumen, such as a reversal of a vas-occlusive contraception, is provided. The methods of reversal include non-surgically or surgically isolating the vas deferens and administering a solvent into the vas deferens lumen. In embodiments, the solvent is capable of deteriorating, breaking down, degrading, disintegrating, reversing, dissolving, destroying, removing, dislodging, de-precipitating, liquefying, flushing and/or reducing, in whole or part, an occlusion or mass, such as a vas-occlusive polymer occlusion disposed in the lumen of the vas deferens. In some embodiments, the method includes alternatively or in addition applying ultrasonic energy and visually identifying an echogenic polymer occlusion in the lumen of the vas-deferens by way of ultrasound imaging prior to, during, or after administering the solvent. In some embodiments, the method further includes alternatively or in addition applying ultrasonic energy and visually confirming placement of a needle or catheter or a portion thereof into the lumen of the vas-deferens by way of ultrasound imaging prior to, during, or after administering the solvent. In some embodiments, the method further includes alternatively or in addition applying ultrasonic energy and visually confirming dissolution of the echogenic polymer occlusion disposed in the lumen of the vas deferens by way of ultrasound imaging, for example, during or after administering the solvent. In some embodiments, instead of administering a solvent, ultrasonic energy can be applied at an intensity and/or frequency capable of breaking down the occlusion. For example, the ultrasonic energy can be applied at an intensity and/or frequency that are capable of lysing microbubbles present in the occlusion, thereby breaking down the occlusion.

According to another embodiment of the invention, a method of delivering an agent to the lumen of the vas deferens is provided. The method includes formulating or incorporating one or more agents into microbubbles of a vas-occlusive polymer solution and/or the solution itself, non-surgically or surgically isolating the vas deferens of a subject, administering the solution into the lumen of the vas deferens, thereby administering the agent into the lumen, and/or allowing the microbubbles to lyse thereby releasing the agent into the lumen of the vas deferens. In some embodiments, the method further includes applying ultrasonic energy at a frequency which is capable of lysing the microbubbles, thereby releasing the agent into the lumen of the vas deferens. In some embodiments, the method further includes applying ultrasonic energy and visually identifying the lumen of the vas-deferens by way of ultrasound imaging prior to, during, or after administering the solution. In some embodiments, the method further includes applying ultrasonic energy and visually confirming placement of a needle or catheter or a portion thereof into the lumen of the vas-deferens by way of ultrasound imaging prior to, during, or after administering the solution. In some embodiments, the method further includes applying ultrasonic energy and visually confirming lysing of the microbubbles in real time by way of ultrasound imaging.

According to another embodiment, the present invention provides compositions and formulations that are visible by way of ultrasound imaging and other types of imaging. The compositions and formulations are designed for use in the methods of the invention. In embodiments, the compositions and formulations include one or more monomers, a polymer or polymers, a copolymer or copolymers, or a block copolymer or block copolymers. In particular embodiments, different formulations of ethylene vinyl alcohol (EVOH) in dimethyl sulfoxide (DMSO) are designed to have advantageous properties for use in methods of the invention such as biocompatibility, gelation time, porosity, hardness, viscosity, swelling/fluid absorbance, melting temperature, gelation temperature, sperm motility, sperm viability, degradation, and/or echogenicity.

Specific aspects of embodiments of the invention include Aspect 1, which are methods of vas-occlusive contraception, comprising: (a) identifying a vas deferens of a subject in need of contraception; (b) placing an ultrasound probe on or near the vas deferens and administering ultrasonic energy to image a lumen portion of the vas deferens, and (c) performing one or more or all of the following steps optionally under guidance of ultrasound imaging: (i) measuring one or more dimensions of the lumen portion of the vas deferens; (ii) percutaneously placing a needle or catheter or portion thereof into the lumen portion of the vas deferens; (iii) administering a substance into the lumen portion of the vas deferens through the needle or catheter; (iv) confirming formation of an occlusion inside the lumen portion, which occlusion is provided by the substance administered into the lumen; and/or (v) determining one or more dimensions of the occlusion inside the lumen portion.

Aspect 2 includes such methods where the substance is a polymer, such as a substance capable of forming a polymer or mass, or a combination of substances capable of forming a polymer or mass when combined, including for example one or more monomers, one or more polymers or polymer precursors, one or more copolymers, or one or more block copolymers, or any combination thereof.

Aspect 3 includes such methods where the polymer is administered as a solution.

Aspect 4 is a method of any of Aspects 1-3, wherein the polymer forms an occlusion in situ by polymerization inside the lumen portion of the vas deferens.

Aspect 5 is a method of any of Aspects 1-4, wherein the step of identifying is performed using a finger technique, such as a three-finger technique. Aspect 6 is a method of any of Aspects 1-5, wherein the step of identifying is further performed using a vas clamp to secure the vas deferens to overlying scrotal skin.

Aspect 7 is a method of any of Aspects 1-6, wherein at least the placing and administering steps are performed under guidance of ultrasound imaging. Aspect 8 is a method of any of Aspects 1-7, wherein at least the confirming and determining steps are performed under guidance of ultrasound imaging. Aspect 9 is a method of any of Aspects 1-8, wherein at least the determining step is performed under guidance of ultrasound imaging. Aspect 10 is a method of any of Aspects 1-9, wherein at least the administering and confirming steps are performed under guidance of ultrasound imaging. Aspect 11 is a method of any of Aspects 1-10, wherein at least the placing, administering, confirming, and determining steps are performed under guidance of ultrasound imaging.

Aspect 12 is a method of any of Aspects 1-11, wherein the ultrasound probe is placed longitudinally to the vas deferens. Aspect 13 is a method of any of Aspects 1-12, wherein the ultrasound probe is placed axially to the vas deferens.

Aspect 14 is a method of any of Aspects 1-13, wherein local anesthesia is administered prior to, during or after the placing step.

Aspect 15 is a method of any of Aspects 1-14, wherein the polymer solution comprises a hydrogel. Aspect 16 is a method of any of Aspects 1-15, wherein the polymer solution is echogenic.

Aspect 17 is a method of any of Aspects 1-16, wherein the polymer solution is echogenic by way of microbubbles present in the polymer solution. Aspect 18 is a method of any of Aspects 1-17, wherein the microbubbles are present in the vas-occlusive polymer solution at a concentration between about $1 \times 10^2$ to about $1 \times 10^9$ microbubbles/ml. Aspect 19 is a method of any of Aspects 1-18, wherein the microbubbles have an average size in the range from about 1 to about 1,000 μm in diameter.

Aspect 20 is a method of any of Aspects 1-19, wherein the substance is injected into the lumen portion at a rate of between about 0.10 to about 1.0 cc/min.

Aspect 21 is a method of any of Aspects 1-20, wherein the occlusion formed inside the lumen portion comprises a plurality of pores. Aspect 22 is a method of any of Aspects 1-21, wherein the pores of the occlusion have a diameter less than about 3 μm. Aspect 23 is a method of any of Aspects 1-22, wherein the pores of the occlusion have a diameter of between about 0.1 nm to about 1 μm. Aspect 24 is a method of any of Aspects 1-23, wherein the pores of the occlusion have a diameter which is small enough to restrict passage of sperm cells but large enough to permit passage of fluids.

Aspect 25 is a method of any of Aspects 1-24, wherein the polymer solution has a viscosity in the range of about 1 to about 1000 centipoise, or from about 1 to 7 Pa*s, and preferably from about 1-3 Pa*s.

Aspect 26 is a method of any of Aspects 1-25, wherein the ultrasonic energy is administered at a frequency between about 1 and about 20 MHZ. Aspect 27 is a method of any of Aspects 1-26, wherein the ultrasonic energy is administered at an intensity between about 0.1 to about 1 Watts/cm2. Aspect 28 is a method of any of Aspects 1-27, wherein between about 0.1 to about 20 Watts of energy is delivered. Aspect 29 is a method of any of Aspects 1-28, wherein the ultrasonic energy is administered in pulsed or continuous mode.

Aspect 30 is a method of any of Aspects 1-29, wherein two substances are injected together inside a lumen portion of the vas deferens to form an occlusion in situ once they meet. Aspect 31 is a method of any of Aspects 1-30, wherein the two substances are different polymers.

Aspect 32 is a method of any of Aspects 1-31, wherein the polymers are each present in a solution.

Aspect 33 is a method of any of Aspects 1-32, wherein the vas-occlusive substance is a medical device.

Aspect 34 is a method of any of Aspects 1-33, wherein the occlusion is washed with saline in situ to assist with removal of solvent from the polymer.

Aspect 35 is a method of any of Aspects 1-34, wherein the substance includes a spermicide.

Aspect 36 is a method of any of Aspects 1-35, wherein the substance is administered into the lumen portion of the vas deferens toward the testes. Aspect 37 is a method of any of Aspects 1-36, wherein the substance is administered into the lumen portion of the vas deferens toward the prostate.

Aspect 38 is a method of any of Aspects 1-37, wherein the one or more dimensions of the occlusion comprise length, width, and diameter.

Aspect 39 is a method of any of Aspects 1-38, wherein the subject is an animal. Aspect 40 is a method of any of Aspects 1-39, wherein the subject is a human.

Aspect 41 is a method of any of Aspects 1-40, wherein the substance is administered by injection. Aspect 42 is a method of any of Aspects 1-41, wherein the substance is administered by controlled infusion.

Aspect 43 is a method of any of Aspects 1-42, wherein the substance is a polymer and formation of an occlusion due to polymerization of the polymer is visualized in real time.

Aspect 44 is a method of any of Aspects 1-43, wherein the polymer comprises from about 5 to about 20 weight percent of an ethylene vinyl copolymer, such as ethylene vinyl alcohol (EVOH), dissolved in a solvent, such as an organic solvent, wherein the ethylene vinyl copolymer comprises about 27 to about 48 mole percent of ethylene, and preferably about 32 mole percent of ethylene. Aspect 45 is a method of any of Aspects 1-44, wherein the polymer comprises from about 10 to about 20 weight percent of an ethylene vinyl copolymer. Aspect 46 is a method of any of Aspects 1-45, wherein the polymer comprises from about 15 to about 20 weight percent of an ethylene vinyl copolymer. Aspect 47 is a method of any of Aspects 1-46, wherein the polymer comprises from about 31 to about 33 mole percent of ethylene. Aspect 48 is a method of any of Aspects 1-47, wherein the polymer comprises about 32 mole percent of ethylene.

Aspect 49 is a method of any of Aspects 1-48, wherein the solvent is dimethyl sulfoxide.

Aspect 50 is a method of any of Aspects 1-49, wherein the solution further comprises an imaging agent. Aspect 51 is a method of any of Aspects 1-50, wherein the imaging agent comprises one or more ultrasound contrast agents. Aspect 52 is a method of any of Aspects 1-51, wherein the one or more ultrasound contrast agents are microbubbles.

Aspect 53 is a method of reversing vas-occlusive contraception, comprising: identifying a vas deferens of a subject in need of reversal of contraception; placing an ultrasound probe on or near the vas deferens and administering ultrasonic energy to image a lumen portion of the vas deferens, and optionally under guidance of ultrasound imaging, performing one or more or all of the following steps: identifying an occlusion in the vas deferens; percutaneously placing a needle or catheter or portion thereof into the lumen portion of the vas deferens; administering one or more substance into the lumen portion of the vas deferens toward the occlusion; and/or confirming removal of the occlusion inside the lumen portion as a result of administering the substance.

Aspect 54 is a method of reversing vas-occlusive contraception, comprising: identifying a vas deferens of a subject in need of reversal of contraception; placing at least one ultrasound probe on or near the vas deferens and administering ultrasonic energy to image a lumen portion of the vas deferens, and optionally under guidance of ultrasound imaging, performing one or more or all of the following steps: identifying an occlusion in the vas deferens; and/or administering focused ultrasonic energy at an intensity or frequency capable of breaking down, deteriorating, degrading, disintegrating, reversing, dissolving, destroying, removing, dislodging, de-precipitating, liquefying, flushing and/or reducing the occlusion in whole or part.

Aspect 55 is a method of any of Aspects 53-54, wherein the focused ultrasonic energy is capable of lysing microbubbles present in the occlusion.

Aspect 56 is a method of delivering an agent to the lumen of the vas deferens, the method comprising: identifying the vas deferens of a subject; placing at least one ultrasound probe on or near the vas deferens; administering one or more solution into the lumen of the vas deferens, which solution comprises microbubbles incorporating an agent; and/or allowing the microbubbles to dissipate to release the agent in the lumen of vas deferens.

Aspect 57 is a method of Aspect 56, comprising applying ultrasonic energy at a frequency which is capable of lysing the microbubbles present in the solution, thereby releasing the agent into the lumen of the vas deferens.

Aspect 58 is a method of any of Aspects 56-57, wherein the agent renders sperm inviable, immotile, and/or infertile. Aspect 59 is a method of any of Aspects 56-58, wherein the agent is a therapeutic drug, antimicrobial, anti-inflammatory, steroid, hormone, ionic solution, protein, peptide, antibody, nucleic acid, and/or fragment thereof.

Aspect 60 is a method of any of Aspects 56-59, wherein the ultrasound probe is a sector, linear, or convex transducer.

Aspect 61 is a method of administering a substance, comprising: identifying a vas deferens of a subject; placing an ultrasound probe on or near the vas deferens and administering ultrasonic energy to image a lumen portion of the vas deferens; and optionally under guidance of ultrasound imaging performing one or more or all of the following: percutaneously placing a needle or catheter or portion thereof into the lumen portion of the vas deferens; and/or administering a substance into the lumen portion of the vas deferens through the needle or catheter.

Aspect 62 is a method of Aspect 61, wherein the substance comprises a diagnostic agent. Aspect 63 is a method of Aspect 61 or 62, wherein the substance comprises an imaging agent. Aspect 64 is a method of any of Aspects 61-63, wherein the imaging agent is detectable by way of radiofrequency, photoacoustic, infrared, or ultrasonic energy. Aspect 65 is a method of any of Aspects 61-64, wherein the imaging agent is an ultrasound contrast agent. Aspect 66 is a method of any of Aspects 61-65, wherein the ultrasound contrast agent comprises microbubbles. Aspect 67 is a method of any of Aspects 61-66, wherein the imaging agent is a dye. Aspect 68 is a method of any of Aspects 61-67, wherein the substance comprises a therapeutic agent. Aspect 69 is a method of any of Aspects 61-68, wherein the therapeutic agent provides contraception. Aspect 70 is a method of any of Aspects 61-69, wherein the therapeutic agent is an occlusive substance.

Aspect 71 is a method of any of Aspects 61-70, wherein the occlusive substance is a polymer. Aspect 72 is a method of any of Aspects 61-71, wherein the polymer is administered as a solution.

Aspect 73 is a method of any of Aspects 61-72, wherein the therapeutic agent comprises a sclerotic agent. Aspect 74 is a method of any of Aspects 61-73, wherein the therapeutic agent enhances fertility of the subject. Aspect 75 is a method of any of Aspects 61-74, wherein the therapeutic agent reduces motility, viability, or fertility of sperm cells.

Aspect 76 is a composition comprising from about 5 to about 20 weight percent of an ethylene vinyl copolymer, such as ethylene vinyl alcohol (EVOH), dissolved in a solvent, such as an organic solvent, wherein the ethylene vinyl copolymer comprises about 27 to about 48 mole percent of ethylene, and preferably about 32 mole percent of ethylene.

Any of the compositions disclosed in this specification can be used in any of the methods, uses, or systems disclosed herein, including the methods, uses, and systems for example of Aspects 1-73, 99-103, 108, 111-119, 122-126, 128-139, and 159-179.

Aspect 77 is the composition of Aspect 76, wherein the composition comprises from about 10 to about 20 weight percent of an ethylene vinyl copolymer. Aspect 78 is the composition of Aspect 76 or 77, wherein the composition comprises from about 15 to about 20 weight percent of an ethylene vinyl copolymer. Aspect 79 is the composition of any of Aspects 76-78, wherein the composition comprises from about 31 to about 33 mole percent of ethylene. Aspect 80 is any of the compositions of Aspects 76-79, wherein the composition comprises about 32 mole percent of ethylene.

Aspect 81 is any of the compositions of Aspects 76-80, wherein the solvent is dimethyl sulfoxide.

Aspect 82 is any of the compositions of Aspects 76-81 comprising an imaging agent. Aspect 83 is any of the compositions of Aspects 76-82, wherein the imaging agent comprises one or more ultrasound contrast agents. Aspect 84 is any of the compositions of Aspects 76-83, wherein the one or more ultrasound contrast agents are microbubbles. Aspect 85 is any of the compositions of Aspects 76-84, wherein the microbubbles are present in the composition at a concentration between about $1\times10^2$ to about $1\times10^9$ microbubbles/ml. Aspect 86 is any of the compositions of Aspects 76-85, wherein the microbubbles have an average size in the range from about 1 to about 1,000 μm in diameter.

Aspect 87 is any of the compositions of Aspects 76-86 comprising an agent that decreases the fertility, motility, or viability of sperm cells. Aspect 88 is any of the compositions of Aspects 76-87, wherein the agent is a small molecule, protein, antibody, peptide, nucleic acid, or fragment thereof. Aspect 89 is any of the compositions of Aspects 76-88, wherein the agent is nonoxynol-9, oxtoxynol-9, benzalkonium chloride, or chlorhexidine.

Aspect 90 is any of the compositions of Aspects 76-89, wherein the microbubbles comprise a gas or a plurality of gases. Aspect 91 is any of the compositions of Aspects 76-90, wherein the gas or plurality of gases is air. Aspect 92 is any of the compositions of Aspects 76-91, wherein the gas comprises nitrogen, argon, or perfluorocarbon. Aspect 93 is any of the compositions of Aspects 76-92, wherein the microbubbles have a shell comprising a polymer, a lipid, a protein, a surfactant, a monosaccharide, a polysaccharide, or glass.

Aspect 94 is any of the compositions of Aspects 76-93, wherein the polymer comprises one or more of natural or synthetic monomers, polymers or copolymers, biocompatible monomers, polymers or copolymers, polystyrene, neoprene, polyetherether 10 ketone (PEEK), carbon reinforced PEEK, polyphenylene, PEKK, PAEK, polyphenylsulphone, polysulphone, PET, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, TEFLON® TFE, polyethylene terephthalate (PETE), TEFLON® FEP, TEFLON® PFA, and/or polymethylpentene (PMP) styrene maleic anhydride, styrene maleic acid, polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamine) (PNIPAM), poly (vinylmethylether), poly (ethylene oxide), poly (ethyl (hydroxyethyl) cellulose), poly(2-ethyl oxazoline), polylactide (PLA), polyglycolide (PGA), poly(lactide-co-glycolide) PLGA, poly(e-caprolactone), polydiaoxanone, polyanhydride, trimethylene carbonate, poly(β-hydroxybutyrate), poly(g-ethyl glutamate), poly (DTH-iminocarbonate), poly(bisphenol A iminocarbonate), poly(orthoester) (POE), polycyanoacrylate (PCA), polyphosphazene, polyethyleneoxide (PEO), polyethylene glycol (PEG), polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly(vinyl alcohol) (PVOH), PEG diacrylate (PEGDA), poly(hydroxyethyl methacrylate) (pHEMA), N-isopropylacrylamide (NIPA), poly(vinyl alcohol) poly(acrylic acid) (PVOH-PAA), collagen, silk, fibrin, gelatin, hyaluron, cellulose, chitin, dextran, casein, albumin, ovalbumin, heparin sulfate, starch, agar, heparin, alginate, fibronectin, fibrin, keratin, pectin, elastin, ethylene vinyl acetate, polyethylene oxide, PEG or any of its derivatives, PLLA, PDMS, PIPA, PEVA, PILA, PEG styrene, Teflon RFE, FLPE, Teflon FEP, methyl palmitate, NIPA, polycarbonate, polyethersulfone, polycaprolactone, polymethyl methacrylate, polyisobutylene, nitrocellulose, medical grade silicone, cellulose acetate, cellulose acetate butyrate, polyacrylonitrile, PLCL, and/or chitosan.

Aspect 95 is any of the compositions of Aspects 76-94, wherein the microbubbles comprise an agent that decreases the fertility, motility, or viability of sperm cells. Aspect 96 is any of the compositions of Aspects 76-95, wherein the agent is cross-linked to the microbubbles. Aspect 97 is any of the compositions of Aspects 76-96, wherein the agent enclosed within a shell of the microbubbles. Aspect 98 is any of the compositions of Aspects 76-97, wherein the agent is a small molecule, protein, antibody, peptide, nucleic acid, or fragment thereof.

Aspect 99 is a method of occluding a lumen comprising: identifying a lumen; administering ultrasonic energy to image the lumen, and performing one or more or all of the following steps optionally under guidance of ultrasound imaging: measuring one or more dimensions of the lumen; percutaneously placing a needle or catheter or portion thereof into the lumen; administering a substance into the lumen through the needle or catheter; confirming formation of an occlusion inside the lumen; and/or determining one or more dimensions of the occlusion inside the lumen.

Aspect 100 is the method of Aspect 99, wherein the lumen is a lumen of a body chosen from one or more of vas deferens, fallopian tube, aneurysm, blood vessel, ducts, tumors, and organs. Aspect 101 is the method of Aspect 100, wherein the substance administered into the lumen is any one or more of the compositions disclosed in this specification, including in particular any one or more of the compositions of Aspects 76-98.

Aspect 102 is use of any one or more of the compositions of Aspects 76-98 for the manufacture of a medicament for the treatment of fertility or infertility of a male or female human or animal subject. Aspect 103 is use according to Aspect 102, wherein the medicament is a vas-occlusive contraceptive.

Aspect 104 is a composition of any one or more of the compositions of Aspects 76-98 for use in the treatment of fertility or infertility of a male or female human or animal subject. Aspect 105 is the composition of Aspect 104, wherein the composition is a vas-occlusive contraceptive.

Aspect 106 is the composition of any one or more of the compositions of Aspects 76-98 for use as a medicament. Aspect 107 is the composition of Aspect 106, wherein the medicament is a vas-occlusive contraceptive.

Aspect 108 is a system for treating infertility or fertility of a male or female human or animal subject, the system comprising: one or more ultrasound imaging apparatus; one or more of any of the compositions disclosed in this specification, including any one or more of those of Aspects 76-98, and optionally provided in a syringe or catheter.

Aspect 109 is any one or more of the compositions disclosed in this specification, including those of Aspects 76-98, wherein the composition has a viscosity in the range of about 1 to about 1000 centipoise, or from about 1 to 7 Pa*s, and preferably from about 1-3 Pa*s. Aspect 110 is the composition of Aspect 109, wherein the composition exhibits a Newtonian fluid behavior rather than shear thinning.

Aspect 111 is the method of any method disclosed in this specification, including any of the methods disclosed in Aspects 1, 61, or 99, wherein the substance or solution comprises a polymer and DMSO and the substance or solution is allowed to precipitate, polymerize, or otherwise form into a hydrogel and the DMSO leaks out, followed by absorption of the DMSO into a lining of the vas deferens.

Aspect 112 is the method of any Aspect disclosed in this specification, including for example Aspect 15, wherein the hydrogel is formulated to swell no more than 80% based on volume of the hydrogel. Aspect 113 is the method of any Aspect disclosed in this specification, including for example Aspect 15, wherein the hydrogel is formulated to swell only so much that the hydrogel does not completely erode epithelial cells or basement membrane of the vas deferens, such as formulated to swell but not completely erode epithelial cells or basement membrane of the vas deferens.

Aspect 114 the method of any Aspect disclosed in this specification, including for example Aspect 15, wherein the hydrogel in the vas deferens has a plug length, which is a length capable of blocking sperm from traversing through the hydrogel, for example the minimal length that achieves the highest efficacy qualified by azoospermia or lack of sperm that are able to traverse the hydrogel.

Aspect 115 is the method of Aspect 114, wherein the plug length is dependent on polymer composition, monomer ratio, molecular weight, concentration in solvent, such as in organic solvent, injection volume, and/or injection speed of the polymer solution, and/or diameter of the inner lumen of the vas deferens.

Aspect 116 is the method of Aspect 114 or 115, wherein the plug length is longer than the average length of the smooth muscle fibers in the vas deferens, such that when the vas deferens constricts and contracts during peristalsis, the hydrogel resists being dislodged, or does not get dislodged, or is prevented from being dislodged.

Aspect 117 is the method of any of Aspects 114-116, wherein the plug length is determined based on lumen diameter, injection volume, and a coefficient (Beta), which is the volume of the plug/injection volume of the polymer-DMSO solution and is a function of the polymer formulation, such as the composition, molecular weight, monomer ratio, and/or concentration.

Aspect 118 is the method of any of Aspects 114-117, wherein Beta is >1 for hydrogels such that the hydrogel takes up more volume than the injection volume, such as a Beta of >2 or >3, such that an injection volume of 100 uL does not exceed 3-4 cm plug length. Aspect 119 is the method of any of Aspects 114-118, wherein the greater the Beta, the lesser the plug length.

Aspect 120 is a composition of any Aspect or composition disclosed in this specification, including those of Aspects 76-98, which is non-biodegradable in a human or animal body or begins to degrade in a human or animal body 1-3 years after implantation, or 2-5 years after implantation, or 3-10 years after implantation, or longer. Aspect 121 is the composition of Aspect 120, wherein the life span of the composition is days, weeks, months, or years, and is preferably permanent.

Aspect 122 is the method of Aspect 101, wherein the substance is allowed to form, polymerize, or precipitate into a hydrogel occlusion in the vas deferens and DMSO leaks out from the substance, followed by absorption of the DMSO into a lining of the vas deferens.

Aspect 123 is the method of Aspect 122, wherein the occlusion is capable of causing sperm that come in contact with the occlusion inviable or immotile.

Aspect 124 is the composition of any of Aspects 76-98, wherein the composition is capable of causing sperm that come in contact with the composition inviable or immotile.

Aspect 125 is any method disclosed in this specification, including those of Aspects 1, 53, 54, 56, 61, or 99, which is capable of being performed and completed in no more than 10 minutes, such as no more than 5 minutes, such as from 3-5 minutes.

Aspect 126 is any method disclosed in this specification, including those of Aspects 1, 53, 54, 56, 61, or 99, wherein an occlusion is formed and the occlusion is washed with saline in situ to assist with removal of solvent from the polymer.

Aspect 127 is a polymer formed from any of the compositions of Aspects 76-98, wherein the polymer has a weight average molecular weight ($M_w$) or Number-Average Molecular weight ($M_n$) ranging from about 1,000 to 1,000,000 Daltons.

Aspect 128 is the method of Aspect 1, wherein the identifying step includes non-surgically identifying the vas deferens.

Aspect 129 is any method disclosed in Aspects 1-128, wherein the identifying step includes surgically identifying the vas deferens. Aspect 130 is any method disclosed in Aspects 1-129, wherein the identifying step includes non-surgically and surgically identifying the vas deferens.

Aspect 131 is any method disclosed in Aspects 1-130 comprising administering a vasodilator prior to, during, or after the identifying step.

Aspect 132 is any method disclosed in Aspects 1-131, wherein the substance comprises microbubbles. Aspect 133 is any method disclosed in Aspects 1-132, wherein the microbubbles have a shell comprising a polymer, a lipid, a protein, a surfactant, a monosaccharide, a polysaccharide, or glass. Aspect 134 is any method disclosed in Aspects 1-133, wherein the microbubbles are formed by way of double syringe agitation.

Aspect 135 is any method disclosed in Aspects 1-134, wherein the one or more substance is a therapeutic agent capable of producing a therapeutic effect upon male urological function. Aspect 136 is any method disclosed in Aspects 1-135, wherein the substance is one or more substance chosen from a contraceptive, an occlusive device, a therapeutic agent, and imaging agent, and echogenic agent, microbubbles, spermicide, antimicrobials, vasodilators, and/or a composition or device for increasing or decreasing motility, viability, and/or fertility of sperm or ova.

Aspect 137 is any method disclosed in Aspects 1-136, wherein the solution comprises a therapeutic drug, antimicrobial, anti-inflammatory, steroid, hormone, ionic solution, protein, peptide, antibody, nucleic acid, and/or fragment thereof.

Aspect 138 is any method disclosed in Aspects 1-137, wherein the substance is sterile or is subject to one or more sterilization method. Aspect 139 is any method disclosed in Aspects 1-138, wherein the substance is sterilized by one or more of using a DMSO compatible 0.22 micron filter, dry heat, autoclave, ethylene oxide, gamma, and/or e-beam based sterilization method.

Aspect 140 is a composition comprising: about 5 to about 20 weight percent of an ethylene vinyl copolymer; wherein the ethylene vinyl copolymer is dissolved in a solvent; wherein the ethylene vinyl copolymer comprises about 27 to about 48 mole percent of ethylene.

Aspect 141 is the composition of Aspect 140 comprising about 10 to about 20 weight percent of the ethylene vinyl copolymer. Aspect 142 is the composition of Aspect 140 or Aspect 141 comprising about 31 to about 33 mole percent of ethylene.

Aspect 143 is the composition of any of Aspects 140-142, which has a viscosity in the range of about 1 to 7 Pa*s. Aspect 144 is the composition of any of Aspects 140-143, which has a viscosity in the range of about 1-3 Pa*s.

Aspect 145 is the composition of any of Aspects 140-144, wherein the ethylene vinyl copolymer is ethylene vinyl alcohol (EVOH).

Aspect 146 is the composition of any of Aspects 140-145, wherein the solvent is an organic solvent.

Aspect 147 is the composition of any of Aspects 140-146 comprising one or more ultrasound contrast agents.

Aspect 148 is the composition of any of Aspects 140-147 comprising one or more microbubbles. Aspect 149 is the composition of any of Aspects 140-148, wherein the microbubbles are present in the composition at a concentration between about $1\times10^2$ to about $1\times10^9$ microbubbles/ml. Aspect 150 is the composition of any of Aspects 140-149, wherein the microbubbles have an average size in the range from about 1 to about 1,000 μm in diameter.

Aspect 151 is the composition of any of Aspects 140-150, wherein the microbubbles have a shell encompassing a gas or a plurality of gases chosen from one or more of air, nitrogen, argon, or perfluorocarbon.

Aspect 152 is the composition of any of Aspects 140-151, wherein the shell of the microbubbles comprises a polymer, a lipid, a protein, a surfactant, a monosaccharide, a polysaccharide, or glass.

Aspect 153 is the composition of any of Aspects 140-152, wherein the shell of the microbubbles comprises a polymer comprising one or more of natural or synthetic monomers, polymers, copolymers or block copolymers, biocompatible monomers, polymers, copolymers or block copolymers, polystyrene, neoprene, polyetherether 10 ketone (PEEK), carbon reinforced PEEK, polyphenylene, PEKK, PAEK, polyphenylsulphone, polysulphone, PET, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, TEFLON® TFE, polyethylene terephthalate (PETE), TEFLON® FEP, TEFLON® PFA, and/or polymethylpentene (PMP) styrene maleic anhydride, styrene maleic acid, polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamine) (PNIPAM), poly (vinylmethylether), poly (ethylene oxide), poly (ethyl (hydroxyethyl) cellulose), poly(2-ethyl oxazoline), polylactide (PLA), polyglycolide (PGA), poly(lactide-co-glycolide) PLGA, poly(e-caprolactone), polydiaoxanone, polyanhydride, trimethylene carbonate, poly(μ-hydroxybutyrate), poly(g-ethyl glutamate), poly(DTH-iminocarbonate), poly (bisphenol A iminocarbonate), poly(orthoester) (POE), polycyanoacrylate (PCA), polyphosphazene, polyethyleneoxide (PEO), polyethylene glycol (PEG), polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly (vinyl alcohol) (PVOH), PEG diacrylate (PEGDA), poly (hydroxyethyl methacrylate) (pHEMA), N-isopropylacrylamide (NIPA), poly(vinyl alcohol) poly(acrylic acid) (PVOH-PAA), collagen, silk, fibrin, gelatin, hyaluron, cellulose, chitin, dextran, casein, albumin, ovalbumin, heparin sulfate, starch, agar, heparin, alginate, fibronectin, fibrin, keratin, pectin, elastin, ethylene vinyl acetate, polyethylene oxide, PEG or any of its derivatives, PLLA, PDMS, PIPA, PEVA, PILA, PEG styrene, Teflon RFE, FLPE, Teflon FEP, methyl palmitate, NIPA, polycarbonate, polyethersulfone, polycaprolactone, polymethyl methacrylate, polyisobutylene, nitrocellulose, medical grade silicone, cellulose acetate, cellulose acetate butyrate, polyacrylonitrile, PLCL, and/or chitosan.

Aspect 154 is the composition of any of Aspects 140-153 comprising an agent that decreases the fertility, motility, or viability of sperm cells. Aspect 155 is the composition of any of Aspects 140-154, wherein the agent is one or more of a small molecule, protein, antibody, peptide, nucleic acid, or fragment thereof, or nonoxynol-9, oxtoxynol-9, benzalkonium chloride, or chlorhexidine.

Aspect 156 is the composition of any of Aspects 140-155, which is a hydrogel formulated such that when the hydrogel is exposed to water the hydrogel swells no more than 80% by volume.

Aspect 157 is the composition of any of Aspects 140-156, which is capable of polymerizing into a polymer and wherein the polymer is non-biodegradable in a human or animal body or begins to degrade in a human or animal body 1-3 years after implantation, or 2-5 years after implantation, or 3-10 years after implantation, or longer.

Aspect 158 is a composition comprising: ethylene vinyl alcohol (EVOH) dissolved in dimethyl sulfoxide (DMSO); wherein the EVOH comprises about 5-20 wt % of ethylene vinyl copolymer; wherein the ethylene vinyl copolymer comprises about 27-48 mole percent ethylene; wherein the EVOH is capable of polymerizing into a polymer comprising a plurality of pores having an average pore size in the range of about 0.1 nm to about 3 μm.

Aspect 159 is a method of occluding a body lumen comprising: imaging a body lumen using ultrasound; and percutaneously placing a needle or catheter or portion thereof into the lumen; administering the composition of Aspect 1 into the lumen through the needle or catheter; and allowing the composition to form an occlusion in the lumen.

Aspect 160 is a method of occluding a body lumen comprising: imaging an animal or human body lumen to view an image of the body lumen; administering a substance into the body lumen; and polymerizing the substance or forming a mass from the substance in the body lumen.

Aspect 161 is the method of Aspect 160, wherein the imaging step is performed prior to, during, and/or after the administering or polymerizing or forming a mass steps.

Aspect 162 is the method of Aspect 160 or 161, wherein as a result of the polymerizing or forming a mass step an occlusion is formed in situ in the body lumen.

Aspect 163 is the method of any of Aspects 160-162, wherein the occlusion is echogenic.

Aspect 164 is the method of any of Aspects 160-163, wherein microbubbles are present in the substance and the microbubbles have an average size in the range from about 1 to about 1,000 μm in diameter.

Aspect 165 is the method of any of Aspects 160-164, wherein the occlusion comprises a plurality of pores having an average pore size in the range of about 0.1 nm to about 3 μm.

Aspect 166 is the method of any of Aspects 160-165, wherein, wherein the occlusion comprises a plurality of pores sized to restrict passage of sperm cells but permit passage of fluids through the pores.

Aspect 167 is the method of any of Aspects 160-166, wherein the substance is a composition having a viscosity in the range of about 1 to 7 Pa*s.

Aspect 168 is the method of any of Aspects 160-167, wherein the microbubbles have a shell comprising a polymer, a lipid, a protein, a surfactant, a monosaccharide, a polysaccharide, or glass.

Aspect 169 is the method of any of Aspects 160-168, wherein the substance includes one or more of a contraceptive, an occlusive device, a therapeutic agent, and imaging agent, and echogenic agent, microbubbles, spermicide, antimicrobials, vasodilators, and/or a composition or device for increasing or decreasing motility, viability, and/or fertility of sperm or ova.

Aspect 170 is the method of any of Aspects 160-169, wherein the polymer comprises one or more of natural or synthetic monomers, polymers, copolymers or block copolymers, biocompatible monomers, polymers, copolymers or block copolymers, polystyrene, neoprene, polyetherether 10ketone (PEEK), carbon reinforced PEEK, polyphenylene, PEKK, PAEK, polyphenylsulphone, polysulphone, PET, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, TEFLON® TFE, polyethylene terephthalate (PETE), TEFLON® FEP, TEFLON® PFA, and/or polymethylpentene (PMP) styrene maleic anhydride, styrene maleic acid, polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamine) (PNIPAM), poly (vinylmethylether), poly (ethylene oxide), poly (ethyl (hydroxyethyl) cellulose), poly(2-ethyl oxazoline), polylactide (PLA), polyglycolide (PGA), poly(lactide-co-glycolide) PLGA, poly(e-caprolactone), polydiaoxanone, polyanhydride, trimethylene carbonate, poly (µhydroxybutyrate), poly(g-ethyl glutamate), poly(DTH-iminocarbonate), poly(bisphenol A iminocarbonate), poly (orthoester) (POE), polycyanoacrylate (PCA), polyphosphazene, polyethyleneoxide (PEO), polyethylene glycol (PEG), polyacrylacid (PAA), polyacrylonitrile (PAN), polyvinylacrylate (PVA), polyvinylpyrrolidone (PVP), polyglycolic lactic acid (PGLA), poly(2-hydroxy-propyl methacrylamide) (pHPMAm), poly(vinyl alcohol) (PVOH), PEG diacrylate (PEGDA), poly(hydroxyethyl methacrylate) (pHEMA), N-i sopropylacrylamide (NIPA), poly(vinyl alcohol) poly(acrylic acid) (PVOH-PAA), collagen, silk, fibrin, gelatin, hyaluron, cellulose, chitin, dextran, casein, albumin, ovalbumin, heparin sulfate, starch, agar, heparin, alginate, fibronectin, fibrin, keratin, pectin, elastin, ethylene vinyl acetate, polyethylene oxide, PEG or any of its derivatives, PLLA, PDMS, PIPA, PEVA, PILA, PEG styrene, Teflon RFE, FLPE, Teflon FEP, methyl palmitate, NIPA, polycarbonate, polyethersulfone, polycaprolactone, polymethyl methacrylate, polyisobutylene, nitrocellulose, medical grade silicone, cellulose acetate, cellulose acetate butyrate, polyacrylonitrile, PLCL, and/or chitosan.

Aspect 171 is the method of any of Aspects 160-170, wherein the substance is a composition comprising from about 5 to about 20 weight percent of an ethylene vinyl copolymer dissolved in a solvent, wherein the ethylene vinyl copolymer comprises about 27 to about 48 mole percent of ethylene.

Aspect 172 is the method of any of Aspects 160-171, wherein the composition comprises from about 10 to about 20 weight percent of an ethylene vinyl copolymer and from about 31 to about 33 mole percent of ethylene.

Aspect 173 is the method of any of Aspects 160-172, wherein the composition comprises dimethyl sulfoxide (DMSO) as the solvent and ethylene vinyl alcohol (EVOH) as the ethylene vinyl copolymer.

Aspect 174 is the method of any of Aspects 160-173, wherein the substance comprises an imaging agent.

Aspect 175 is the method of any of Aspects 160-174, wherein the body lumen is chosen from one or more of a vas deferens, fallopian tube, aneurysm, blood vessel, ducts, tumors, and organs.

Aspect 176 is a method of removing an occlusion disposed in a body lumen, comprising: imaging a body lumen and an occlusion disposed therein; performing one or more or all of the following: administering a substance into the body lumen and allowing the substance to deteriorate, break down, degrade, disintegrate, reverse, dissolve, destroy, remove, dislodge, de-precipitate, liquefy, flush and/or reduce the occlusion in whole or part; and/or administering ultrasonic energy to the occlusion at an intensity and/or frequency capable of deteriorating, breaking down, degrading, disintegrating, reversing, dissolving, destroying, removing, dislodging, de-precipitating, liquefying, flushing and/or reducing the occlusion in whole or part; confirming deterioration of the occlusion.

Aspect 177 is the method of Aspect 176, wherein the body lumen is chosen from one or more of a vas deferens, fallopian tube, aneurysm, blood vessel, ducts, tumors, and organs.

Aspect 178 is a method of occluding a body lumen comprising: imaging a body lumen with ultrasound; injecting a composition comprising ethylene vinyl alcohol (EVOH) and dimethyl sulfoxide (DMSO) into the body lumen; and polymerizing the composition or forming a mass from the composition in situ in the body lumen.

Aspect 179 is the method of Aspect 178, wherein the body lumen is chosen from one or more of a vas deferens, fallopian tube, aneurysm, blood vessel, ducts, tumors, and organs.

Additional embodiments and aspects of the invention will be apparent in the foregoing detailed description.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

FIG. 15A is a diagram representing the chemical structure of styrene maleic acid (SMA).

FIG. 15B is a diagram representing the chemical structure of ethylene vinyl alcohol (EVOH).

FIG. 22 is a table showing the results of statistical analysis (Tukey testing) of the results of FIG. 21 comparing EVOH at different weight percentages (5%, 10%, 15%, and 20%).

FIG. 23 is a table showing the results of a cytotoxicity assay (MEM elution) for select EVOH polymer candidates.

FIG. 28 is a table showing the relationship between inner diameter (dilated) and injection volume and for various targeted occlusion sizes for human vas-occlusive contraception.

FIG. 29 is a table showing results of Brunauer-Emmett-Teller analysis for select polymer candidates.

FIG. 34A is a table showing the results of statistical analysis (initial ANOVA) of the results of FIG. 33.

FIG. 34B is table showing the results of statistical analysis (Tukey testing) of the results of FIG. 33.

FIG. 36A is a table showing the results of statistical analysis (initial ANOVA) of the results of FIG. 35.

FIG. 36B is table showing the results of statistical analysis (Tukey testing) of the results of FIG. 36.

DETAILED DESCRIPTION OF VARIOUS EMBODIMENTS OF THE INVENTION

Figure 1A:
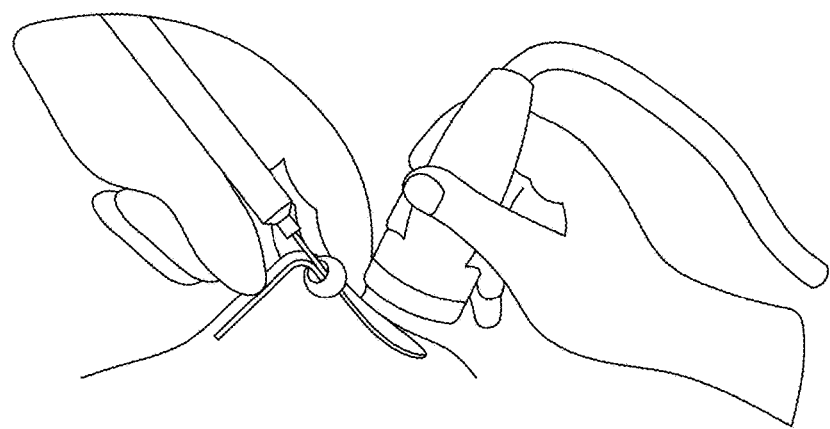
FIG. 1A is diagram illustrating a method of vas-occlusive contraception according to an embodiment of the invention.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

As used herein, a "subject" is an animal. Such animals include mammals, including companion animals such as a dog or cat, farm animals such as a horse or cow, laboratory animals such as a mouse or rat, as well as non-human primates and humans.

As used herein, a "subject in need of contraception" is a patient, animal, mammal, or human, who will benefit from the method of this invention.

The term "biocompatible," as used herein, refers to a material that does not elicit a substantial detrimental response in the host.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 40%-60%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "peptide" typically refers to short polypeptides.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, a "non-surgical" (or "non-surgically") aspect of a procedure is performed without surgery. "Non-surgical isolation" refers to any non-surgical technique which identifies an anatomical part through the intact skin or connective tissues such that it is positioned underneath the skin or connective tissue. Thus, "non-surgical isolation" does not involve the use of a scalpel to incise the skin or the use of sutures to close the skin after incision.

As used herein, the word "VASINTOMY™" refers to any embodiment of the contraceptive methods described in this disclosure.

As used in this specification, ethylene vinyl alcohol (EVOH) compositions are referred to as "EVOH X-Y %", where X is the ethylene content (mole percentage) of EVOH and Y % is the weight percentage of EVOH in the composition. For example, EVOH 32-10% indicates that the EVOH in the composition has an ethylene content of 32%, a vinyl alcohol content of 68%, and EVOH represents 10% of the composition by weight.

In embodiments, the present invention relates generally to methods of administration of a substance into any lumen in the body, such as the lumen of the vas deferens, optionally under guidance of ultrasound through non-surgical or surgical routes of administration. In a preferred embodiment, the substance is administered percutaneously. Further, the present invention contemplates any therapeutic or diagnostic aspect of the methods of the invention that can be appreciated by a skilled artisan.

For example, one embodiment provides a method which includes non-surgically or surgically isolating a vas deferens of a subject, placing an ultrasound probe on or near the vas deferens and administering ultrasonic energy to image a lumen portion of the vas deferens, and optionally under guidance of ultrasound imaging percutaneously placing a needle or catheter or portion thereof into the lumen portion of the vas deferens, and administering a substance into the lumen portion of the vas deferens through the needle or catheter.

The substance can include any substance that has the potential to produce a therapeutic effect upon male urological function, or serve as a diagnostic of urological function. For example, the substance can be or include a diagnostic agent such as an imaging agent.

The imaging agent can be detectable by way of any form of energy used in diagnostic imaging, such as, for example, by way of radiofrequency, photoacoustic, infrared, or ultrasonic energy. For example, the imaging agent can be or include an ultrasound contrast agent such as microbubbles or can be or include a dye. Additionally, the substance can be or include a therapeutic agent. In one particular embodiment, the agent is therapeutic in the sense that it produces a desirable contraceptive effect. For example, the therapeutic agent can be an occlusive substance (otherwise known herein as a vas-occlusive substance) that exerts a desired contraceptive effect by blocking the transport of sperm cells through the vas deferens lumen. The therapeutic agent can include any non-occlusive substance, such as small molecules, antibodies, peptides, proteins, nucleic acids, and the like.

In one particular embodiment, the therapeutic agent is a polymer such as those described further herein, and the polymer is administered as a solution and results in polymerization in situ to form an occlusion in the vas deferens. However, the present invention contemplates any agent that can exert a contraceptive mechanism of action in the vas deferens. Additional contraceptive agents are contemplated, including sclerotic agents, which cause vessels to shrink by producing endothelial damage. Alternatively, the therapeutic agent can target sperm cells and exert a contraceptive effect through reduced motility, viability, or fertility of the sperm cells.

In alternative embodiments, the therapeutic agent can be an agent that enhances fertility, such as an agent that has an effect of increasing sperm transport, or enhances motility, viability, or fertility of sperm cells, if such is the therapeutic goal. In one embodiment, the therapeutic agent may be an antibiotic. These are merely illustrative examples of the different applications of the invention and are not intended to limit the scope. This invention contemplates that any agent can be administered in the methods of administration of substances into the vas deferens, such that the method covers any therapeutic or diagnostic urological application.

While the invention generally relates to methods of administration of a substance into the lumen of the vas deferens optionally under guidance of ultrasound through non-surgical or surgical routes of administration, more particular embodiments concerning contraceptive implementations of the methods will be discussed. Particularly advantageous embodiments of the present invention for which there is a critical need for include methods of vas-occlusive contraception that are minimally invasive, highly accurate, reproducible, safe, long-lasting, and easy to implement in an outpatient setting. According to embodiments, these advantages stem from the use of ultrasound imaging throughout at least a portion of the procedure.

The inventors' advantageous implementation of ultrasound to guide the placement of a vas-occlusive substance into the lumen of the vas deferens has not been previously established in the contraceptive arts. Even further, the use of a non-surgical or surgical method for isolating the vas deferens and placement of a contraceptive in the lumen by way of percutaneous injection or controlled intra-vasal infusion is a significant improvement over previous vas-occlusive procedures in development, which generally require an incision to isolate the vas deferens. Moreover, the inventive procedure can be performed by a physician using local anesthesia in an outpatient setting very rapidly, in as little as five minutes, thus minimizing any discomfort to the subject. Moreover, the inventive procedure requires minimal training to perform, such that it can be performed by any medical practitioner familiar with ultrasound imaging. Even further, while the inventive procedure provides long-lasting contraception, it is easily reversible by way of a similar procedure. These advantages of the invention, only some of which are discussed herein, will be further apparent as various embodiments and features of the invention are described.

One embodiment of the invention includes a method of vas-occlusive contraception. The method can include non-surgically or surgically isolating a vas deferens of a subject in need of contraception, placing an ultrasound probe on or near the vas deferens and administering ultrasonic energy to image the lumen of the vas deferens, and performing at least one of the following steps optionally under guidance of ultrasound imaging, such as (a) determining one or more dimensions of the lumen of the vas deferens (b) percutaneously placing a needle or catheter or portion thereof into the lumen of the vas deferens, (c) administering a substance into the lumen of the vas deferens, (d) confirming formation of an occlusion inside the lumen as a result of administering the substance, and (e) determining one or more dimensions of the occlusion inside the lumen portion.

According to embodiments, the non-surgical or surgical isolation of the vas deferens includes use of a vas-fixation clamp to grip the vas deferens through the skin of the scrotum, and/or subcutaneous isolation through the physician's fingers. For example, the vas deferens can be isolated through the use of the "three-finger technique," in which the non-dominant hand is used to manipulate the vas into a subcutaneous position (see Stockton D M et al. "No-scalpel vasectomy: a technique for family physicians." Am Fam Physician. 1992; 46:1153-67; Clenney T L, "Vasectomy Techniques," Am Fam Physician. 1999; 60(1):137-146). Alternatively or in addition, a vas-fixation clamp can be used to secure the vas deferens in a sub-cutaneous position. Further, the vas clamp can contain an additional component that guides the needle into the lumen of the vas deferens. Additionally, the needle may include a ball-and-socket joint which allows for easier manipulation of the needle.

In embodiments, the substance is any substance which forms an occlusion inside the vas deferens when administered into the lumen. The substance can be solid, semi-solid, or liquid. Conceivably, any substance that can be administered into the vas deferens lumen and forms a plug or occlusion can be used. Preferably, the substance is biocompatible. The substance can be organic or inorganic. The substance can form an occlusion in situ through a phase state change, such as from liquid to solid. The substance can form an occlusion by expansion in situ. The substance can also be a medical device, such as a nanoparticle, stent-like device, electro-spun mesh, or a nanobot. In embodiments, the substance is selectively porous such that is allows fluids to pass while blocking the passage of sperm cells. In some embodiments, the substance is a composition. In some embodiments, the substance is a polymer. In some embodiments, more than one substance is administered. In some embodiments, the substance is selectively toxic to sperm cells but not toxic to other cells of the genitourinary tissues. The selective toxicity can result in decreased motility, viability, or fertility of the sperm cells.

According to embodiments, a vas-occlusive polymer can then be administered into the vas deferens of both sides by way of percutaneous injection or controlled intra-vasal infusion into the vas, optionally under the guidance of ultrasound imaging. For example, the vas-occlusive polymer can be dissolved in a solvent, preloaded in a syringe, and injected into the lumen of the vas deferens by way of a needle or catheter. The needle or catheter is chosen to be of a size that fits inside the lumen of the vas deferens. For example, one publication has estimated the lumen of the vas deferens in humans to vary from 0.25 to 0.55 mm in diameter, while having an external diameter of between 2 and 4 mm (see E. S. Hafez, P. Kenemans, "Atlas of Human Reproduction: By Scanning Electron Microscopy," 1982, MTP Press, Hingham, Mass.). Thus, the inner diameter (lumen) of the vas is only a small portion of its outer diameter. However, various other studies have shown that the inner diameter can dilate as large as 1.8 mm (Liu, X. et al.). The outer portion of the vas is made up of layers of smooth muscle. This size differential underscores the need for ultrasound imaging to confirm successful administration of the vas-occlusive substance into the lumen rather than "off-target" administration into the smooth muscle. The size of the needle or catheter can be chosen based on the estimated size of the vas from the literature, or determined by imaging the dimensions of the vas lumen of the subject through ultrasound. In embodiments, the size of the needle can be between 18 gauge to 34 gauge, depending on the estimated or determined diameter of the vas lumen of the particular species that is the target of contraception. In other embodiments, the size of the needle is between 21 gauge and 31 gauge. In other embodiments, the size of the needle is at least 23 gauge, such as between 23 gauge and 29 gauge. In another aspect, the needle that is used to deliver the injection solution contains bores on the side, which allow for the solution to be excreted around the needle, in addition to the bevel.

According to embodiments, the vas-occlusive polymer is first prepared as a solution. The solution can be prepared at a concentration of polymer ranging from about 0.1 to about 1.0 g/ml (or higher) of solvent medium. In other embodiments, the vas-occlusive polymer is prepared as a solution at a concentration ranging from about 0.25 to about 0.75 g/ml. In some embodiments, the concentration is about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, or 1.0 g/ml. Various solvents for dissolving the above polymers include dimethyl sulfoxide (DMSO), or other organic solvents, or solutions of sodium bicarbonate, and the like. The solvents may also contain agents that selectively dissolve or de-precipitate the polymer by breaking the cross-links including, but not limited to, reducing agents. The polymers can be prepared as a solution using these solvents and delivered (e.g. injected) into the lumen of the vas deferens by way of a needle or catheter. In some embodiments, the polymer gel can be washed with saline after delivery to fully form the occlusion and help with removal of solvents such as DMSO. In some embodiments, two different polymer solutions are prepared. The two different polymer solutions together are capable of forming a hydrogel when they are mixed together. For example, the two different polymer solutions can be administered into the vas deferens and can form a hydrogel inside the lumen once they meet. Examples of such systems include PEG-thiol and PEG maleimide, which form a cross-linked hydrogel via "Click" reaction upon mixing.

Polymers that are generally useful for forming an occlusion or embolism inside a vessel are known in the art. Non-limiting examples of such polymers include styrene maleic anhydride, styrene maleic acid, polyurethane, silicone and those described in International Patent Application Publication No. WO 2015058169. Additional non-limiting examples include hydrogels such as such as polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamine) (PNIPAM), poly (vinylmethylether), poly (ethylene oxide), poly (ethyl (hydroxyethyl) cellulose), poly(2-ethyl oxazoline), polylactide (PLA), polyglycolide (PGA), poly(lactide-co-glycolide) PLGA, poly(e-caprolactone), polydiaoxanone, polyanhydride, trimethylene carbonate, poly(μ-hydroxybutyrate), poly(g-ethyl glutamate), poly(DTH-iminocarbonate), poly (bisphenol A iminocarbonate), poly(orthoester) (POE), polycyanoacrylate (PCA), polyphosphazene, polyethyleneoxide (PEO), polyethylene glycol (PEG), polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly (vinyl alcohol) (PVOH), PEG diacrylate (PEGDA), poly (hydroxyethyl methacrylate) (pHEMA), N-isopropylacrylamide (NIPA), poly(vinyl alcohol) poly(acrylic acid) (PVOH-PAA), or natural polymers such as collagen, silk, fibrin, gelatin, hyaluron, cellulose, chitin, dextran, casein, albumin, ovalbumin, heparin sulfate, starch, agar, heparin, alginate, fibronectin, fibrin, keratin, pectin, or elastin. Additional examples include those described in U.S. Pat. No. 6,878,384, which discloses that hydrogels can be prepared by forming a liquid reaction mixture that contains a) monomer(s) and/or polymer(s) at least portion(s) of which are sensitive to environmental changes (e.g., changes in pH or temperature), b) a crosslinker and c) a polymerization initiator. Additional examples of hydrogels include those described in U.S. Patent Application Publication No. 20090053276A1 and U.S. Pat. Nos. 6,703,047; 5,612,052; 5,714,159; 6,413,539; 4,804,691; 6,723,781; 5,866,554; 6,037,331; 6,514,534; 6,297,337; 6,514,535; and 5,702,717. In embodiments, the polymers can be prepared as a solution prior to administration into the lumen of the vas.

Additional non-limiting examples include ethylene vinyl acetate, polyethylene oxide, PEG or any of its derivatives, PLLA, PDMS, PIPA, PEVA, PILA, PEG styrene, PEEK, nylon, Teflon RFE, PEKEKK, FLPE, neoprene, PETE, Teflon FEP, Teflon PFA, PMP, methyl palmitate, NIPA, polycarbonate, polyethersulfone, polycaprolactone, polymethyl methacrylate, polypropylene, polyurethane, polystyrene, polyisobutylene, nitrocellulose, medical grade silicone, cellulose acetate, cellulose acetate butyrate, polyacrylonitrile, PLCL, and/or chitosan.

In some embodiments, the polymer is a copolymer such as a block copolymer, an alternating copolymer, a graft copolymer, a random copolymer, a periodic copolymer, and a statistical copolymer. In a particular embodiment, the copolymer is ethylene vinyl alcohol (EVOH). According to another specific embodiment, the copolymer is EVOH dissolved in dimethylsulfoxide (DMSO).

In one embodiment, the EVOH has a weight percent from around 1% to around 50% of the complete polymer composition in DMSO, such as from 1% to 2%, from 2% to 3%, from 3% to 4%, from 4% to 5%, from 5% to 6%, from 6%, to 7%, from 7%, to 8%, from 8% to 9%, from 9% to 10%, and so on. In another embodiment, the weight percent of the EVOH is from around 6% to around 20% of the complete polymer composition, including 7% to around 20%, 8% to around 20%, 9% to around 20%, as so on. In another embodiment, the weight percent of the EVOH is around 10% to around 20% of the complete polymer composition, including 10%, 11%, 12%, 13%, 14%, 15%, 16%, 17%, 18%, 19%, 20%, and any percentage in between. In another embodiment, the weight percent of the EVOH is around 10% to around 18% of the complete polymer composition. EVOH begins to reach its saturation point at 20 wt %. Further, as the wt % increases, so does the viscosity making injection of the material difficult. Thus, solutions at a weight percentage of greater than 20% are less desirable.

In another aspect, the weight percent of EVOH is chosen such that when the polymer gel is formed, the pores of the gel are small enough to prevent sperm from traveling through. In one aspect, the EVOH may have an effect on sperm motility, fertility, and viability. In another aspect, sperm that interact with EVOH may lose biomarkers, carbohydrates, or proteins that are important for fertilization.

In one embodiment, the ethylene content in the EVOH can be a molar ratio (mole percent) of around 20% to around 60% of the polymer, including 20%, 25%, 30%, 35%, 40%, 45%, 50%, 55%, and 60%, or any percentage in between these values. According to one embodiment, the ethylene content is a molar ratio of about 27% to about 44% of the polymer. According to another embodiment, the ethylene content is in the range of from about 27% to about 38% of the polymer, including 27%, 28%, 29%, 30%, 31%, 32%, 33%, 34%, 35%, 36%, 37%, and 38%. According to another embodiment, the ethylene content is in the range of about 31% to about 33% of the polymer. According to another embodiment, the ethylene content is about 32% of the polymer. The ethylene content controls the hydrophilicity/hydrophobicity of the polymer: the lower the ethylene content, the higher the vinyl alcohol and therefore, greater hydrophilicity. These factors can impact how the hydrogel forms in water, swells, and absorbs water, as well as its viscosity, thermal stability, and durability. In embodiments, the hydrogel swells no more than 80%, such as no more than 75%, or no more than 70%, or no more than 65%, or no more than 60% and so on. Additionally, the percentage of ethylene can impact the injection force required for administration. For example, a 27% ethylene-content allows for an easy injection because the polymer gel does not adhere to the inside of the needle.

According to embodiments, the EVOH polymeric gel may produce a partial or full occlusion when injected into the vas. In one aspect, the EVOH polymer may block sperm, fluids, molecules such as proteins (e.g., antibodies), carbohydrates, gases, and/or lipids. In another aspect, the EVOH gel may occlude sperm due to small pore size but may allow fluids and other molecules to pass. In another aspect, the EVOH has spermicidal properties causing the sperm that come in contact to become inviable or immotile.

Embodiments of the invention provide inventive compositions of EVOH for use in the methods of the invention. By adjusting the molecular weights and monomer ratios of EVOH, the present inventors have demonstrated that other polymer properties important for contraception can be tailored. The inventive compositions are designed to optimize various properties that are relevant to the methods of the invention, including biocompatibility, gelation time, porosity, hardness, viscosity, swelling/fluid absorbance, melting temperature, gelation temperature, sperm motility, sperm viability, degradation, and/or echogenicity.

Embodiments of the invention include a composition comprising EVOH dissolved in a solvent. Preferably the solvent is DMSO, but the compositions can include any biocompatible solvent or solvents. Non-limiting examples of the compositions expressed as "EVOH X-Y %" where X is the ethylene content (mole percentage) of EVOH and Y % is the weight percentage of EVOH in the composition include the following: EVOH 27-8%, EVOH 27-9%, EVOH 27-10%, EVOH 27-11%, EVOH 27-12%, EVOH 27-13%, EVOH 27-14%, EVOH 27-15%, EVOH 27-16%, EVOH 27-17%, EVOH 27-18%, EVOH 27-19%, EVOH 27-20%, EVOH 28-8%, EVOH 28-9%, EVOH 28-10%, EVOH 28-11%, EVOH 28-12%, EVOH 28-13%, EVOH 28-14%, EVOH 28-15%, EVOH 28-16%, EVOH 28-17%, EVOH 28-18%, EVOH 28-19%, EVOH 28-20%, EVOH 29-8%, EVOH 29-9%, EVOH 29-10%, EVOH 29-11%, EVOH 29-12%, EVOH 29-13%, EVOH 29-14%, EVOH 29-15%, EVOH 29-16%, EVOH 29-17%, EVOH 29-18%, EVOH 29-19%, EVOH 29-20%, EVOH 30-8%, EVOH 30-9%, EVOH 30-11%, EVOH 30-12%, EVOH 30-13%, EVOH 30-14%, EVOH 30-15%, EVOH 30-16%, EVOH 30-17%, EVOH 30-18%, EVOH 30-19%, EVOH 30-20%, EVOH 31-8%, EVOH 31-9%, EVOH 31-10%, EVOH 31-11%, EVOH 31-12%, EVOH 31-13%, EVOH 31-14%, EVOH 31-15%, EVOH 31-16%, EVOH 31-17%, EVOH 31-18%, EVOH 31-19%, EVOH 31-20%, EVOH 32-8%, EVOH 32-9%, EVOH 32-10%, EVOH 32-11%, EVOH 32-12%, EVOH 32-13%, EVOH 32-14%, EVOH 32-15%, EVOH 32-16%, EVOH 32-17%, EVOH 32-18%, EVOH 32-19%, EVOH 32-20, 3 EVOH 3-8%, EVOH 33-9%, EVOH 33-10%, EVOH 33-11%, EVOH 33-12%, EVOH 33-13%, EVOH 33-14%, EVOH 33-15%, EVOH 33-16%, EVOH 33-17%, EVOH 33-18%, EVOH 33-19%, EVOH 33-20%, EVOH 34-8%, EVOH 34-9%, EVOH 34-10%, EVOH 34-11%, EVOH 34-12%, EVOH 34-13%, EVOH 34-14%, EVOH 34-15%, EVOH 34-16%, EVOH 34-17%, EVOH 34-18%, EVOH 34-19%, EVOH 34-20%, EVOH 35-8%, EVOH 35-9%, EVOH 35-10%, EVOH 35-11%, EVOH 35-12%, EVOH 35-13%, EVOH 35-14%, EVOH 35-15%, EVOH 35-16%, EVOH 35-17%, EVOH 35-18%, EVOH 35-19%, EVOH 35-20%, EVOH 36-8%, EVOH 36-9%, EVOH 36-10%, EVOH 36-11%, EVOH 36-12%, EVOH 36-13%, EVOH 36-14%, EVOH 36-15%, EVOH 36-16%, EVOH 36-17%, EVOH 36-18%, EVOH 36-19%, EVOH 36-20%, EVOH 37-8%, EVOH 37-9%, EVOH 37-10%, EVOH 37-11%, EVOH 37-12%, EVOH 37-13%, EVOH 37-14%, EVOH 37-15%, EVOH 37-16%, EVOH 37-17%, EVOH 37-18%, EVOH 37-19%, EVOH 37-20%, EVOH 38-8%, EVOH 38-9%, EVOH 38-10%, EVOH 38-11%, EVOH 38-12%, EVOH 38-13%, EVOH 38-14%, EVOH 38-15%, EVOH 38-16%, EVOH 38-17%, EVOH 38-18%, EVOH 38-19%, EVOH 38-20%, and so on. However, these compositions are intended to be merely exemplary. A skilled artisan can appreciate that the present invention includes other compositions not explicitly stated, such as those having an ethylene content or EVOH weight percentage outside of these ranges or between values that are explicitly stated.

In the foregoing examples at the end of this disclosure, the present inventors have developed novel EVOH compositions with respect to ethylene content and EVOH concentrations that have optimal properties with respect to one or more of biocompatibility, gelation time, porosity, hardness, viscosity, swelling/fluid absorbance, melting temperature, gelation temperature, sperm motility, sperm viability, degradation, and echogenicity. The compositions are optimized for use in the inventive methods. Thus, the present invention encompasses novel EVOH compositions that have been specifically designed for use in ultrasound-guided vas-occlusive contraception.

In embodiments, the viscosity of the polymer solution ranges from about 0.10 centipoise to about 100,000 centipoise, or any viscosity in between, including 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100,000 centipoise. In other embodiments, the viscosity of the polymer solution ranges from about 1 to about 1,000 centipoise, or from about 1 to 7 Pa*s, such as from about 1 to 3 Pa*s. In other embodiments, the viscosity of the polymer solution ranges from about 1 to about 100 centipoise. By way of illustrative examples, a solution of about 1 centipoise has the viscosity of water, a solution in the hundreds of centipoise has the viscosity of motor oil, a solution of about 1000 centipoise has the viscosity of glycerin, and a solution of about 50,000 centipoise has the viscosity of ketchup. However, it is preferred that the viscosity of the polymer solution is maintained low enough so that it is not too viscous such that the injection cannot be performed with a syringe and needle. The viscosity of the polymer solution can be manipulated by the varying the polymer and/or solvent chosen, the polymer concentration, polymer molecular weight, microbubble composition, microbubble size, microbubble concentration, and cross-linking.

In embodiments, the substance, solution, or composition administered into the body lumen can be a composition comprising a polymer, copolymer, block copolymer, monomers, or a polymer precursor or pre-polymer, wherein the composition is capable of forming a polymer occlusion in the body lumen upon administration therein. In some cases, polymerization of the substance, solution, or composition may occur before, during, and/or after administration of the substance, solution, or composition into the body lumen, such as a vas deferens. Further, for example, in the context of this specification referring to administering a polymer can include administering a polymer already formed, or administering the precursor or pre-polymer to a copolymer or block copolymer, such as polymer(s) or copolymer(s), or administering the precursor or pre-polymer to a polymer, such as one or more monomers, or combinations thereof, whether or not the monomer(s), polymer(s), or copolymer(s) have already begun forming the polymer, copolymer or block copolymer prior to, during, or after administration of the composition, solution, or substance. In situ forming of the occlusion in a body lumen, such as a vas deferens, includes methods where any part of the forming of the occlusion occurs in the body lumen and not necessarily that the occlusion must be formed completely in situ. Thus, forming the occlusion completely or partially in a body lumen are included as aspects of embodiments of the invention.

In embodiments, other constituents are included in the vas-occlusive polymer solution. These may include additional contrast agents, imaging agents, therapeutic drugs, antimicrobials, anti-inflammatories, spermicidal agents, vasodilators, steroids, hormones, ionic solutions, proteins, nucleic acids, antibodies, or fragments thereof. The other constituents can provide additional contraceptive activity to the vas-occlusive polymer solution. For example, the other constituents may produce an effect on sperm motility, viability, or fertility and may be a small molecule, protein, peptide, antibody, nucleic acid, or fragment thereof. For example, a 22 kD sperm protein, SP-22, correlates with fertility and predicts fertility in males. See U.S. Pat. No. 6,197,940. Antibodies to this protein, such as those described in U.S. Pat. No. 7,754,212 can be included in the vas-occlusive polymer solution. Antibodies against other sperm proteins can be included. In one aspect, the antibody is S19, also known as MHS-8, against the sperm-specific glycoprotein SAGA1. Additionally, spermicidal agents such as nonoxynol-9, oxtoxynol-9, benzalkonium chloride, or chlorhexidine can be included. Additionally, the vas-occlusive polymer and/or solvent can be innately spermicidal, such that no exogenous spermicidal agent is included.

In one embodiment, the vas-occlusive polymer may be modified or cross-linked with fusion proteins, amino acid sequences, or peptides (natural or synthetic). In one aspect, the polymer may be modified with polyethylene glycol (PEG), where PEGylation may enhance the biocompatibility of the polymer. The polymer may be modified with an amino acid sequence. In another aspect, the amino acid sequence contains lysine residues which are cross-linked to the maleic acid or maleic anhydride groups. The amino acid sequence may be cleaved with an endo- or exo-protease. In one aspect, the amino acid sequence is a dipeptide. The addition of a protease causes the gel to de-precipitate, liquefy, or dissolve for reversal. In one aspect, the protease is found naturally in the human body. In one aspect, the protease is not found in the human body. The amino acid sequence and protease may be chosen from a database. In one aspect, the protease is papain, bromelain, actinidin, ficin, or zingibain. In another aspect, the di-amino acid scission site may only be cleaved by a bacterial protease. Preferably, the protease is injected in a solution form into the vas deferens to reverse, de-precipitate, liquefy, dissolve, or flush out the polymer gel.

In embodiments, the vas-occlusive polymer solution is formulated to include an ultrasound contrast-enhancing agent such that is or becomes echogenic. The ultrasound contrast agent can be microbubbles, or any other known ultrasound contrast agent or which becomes known in the art. Ultrasound contrast agents have been reviewed in the literature (see Calliada F, et al., "Ultrasound contrast agents: basic principles", Eur J Radiol. 1998 27 Suppl 2:S157-60 and Cosgrove D, "Ultrasound contrast agents: An overview", Radiology 2006 Volume 60, Issue 3, Pages 324-330). In one embodiment, the microbubbles decrease the lateral and axial resolution (as calculated by the full-width, half-maximum formula), thereby enhancing the visibility of the gel on the ultrasound. The addition of microbubbles allow for the gel to be echogenic (visible on ultrasound) for extended duration.

In embodiments, the ultrasound contrast-enhancing agent includes gas-containing microbubbles or microspheres. The microbubbles may also be hollow or porous. The gas may include a mixture or combination of gases (e.g. air), or any inert gas, such as nitrogen, argon, perfluorocarbon, and the like. The microbubbles may have a shell which includes as components a polymer, a lipid, a protein, a surfactant, a monosaccharide, a polysaccharide, or glass. Provisional Patent Application No. 62/254,381 disclosed a vas-occlusive polymer gel containing microbubbles (e.g., glass). The microbubbles caused the gel to be echogenic, or visible under ultrasound.

Useful polymers for microbubbles may include, but are not limited to, polystyrene, neoprene, polyetherether 10 ketone (PEEK), polyethylene, polypropylene, polyetherketoneetherketoneketone (PEKEKK), nylon, TEFLON® TFE, polyethylene terephthalate (PETE), TEFLON® FEP, TEFLON® PFA, and polymethylpentene (PMP). The polymers may be insoluble in DMSO. Useful polysaccharides for microbubbles include, but are not limited to, cellulose, cellophane, or carboxymethyl cellulose, or any derivative thereof. An example of a protein constituent of a microbubble shell includes albumin, and an example of a saccharide constituent of a microbubble shell includes galactose. Additionally, the microbubbles may include multiple constituents.

In embodiments, the microbubbles can be formulated to contain additional agents or drugs, including, but not limited to, therapeutic drugs, antimicrobials, anti-inflammatories, steroids, drugs, hormones, ionic solutions, proteins, peptides, antibodies, or nucleic acids, or fragments thereof. The additional drugs or agents can be controlled through sustained release. The molecules can be conjugated to the microbubbles of the invention or included as internal components of the microbubbles. The molecule may be a small molecule, protein, a peptide, antibody, or a ligand which targets sperm to render the sperm immotile, infertile, or inviable.

In embodiments, the microbubbles or microspheres of the invention can vary in size, or can be provided in a fairly uniform size range. The microbubbles can range in size from about 0.10 to about 1,000 μm in diameter. However, a substantially uniform size range is preferred to provide maximum contrast. For example, the microbubbles can be provided in a size ranging from about 1-2, 2-3, 3-4, 4-5, 5-6, 6-8, or 8-10 μm in diameter. Additionally, the microbubble shell thickness can vary in size. In embodiments, the microbubbles are provided at a concentration ranging from about $1\times10^2$ to about $1\times10^9$ microbubbles/ml, including $1\times10^3$, $1\times10^4$, $1\times10^5$, $1\times10^6$, $1\times10^7$, and $1\times10^8$ microbubbles/ml. In some embodiments, the microbubbles are innately present in the vas-occlusive polymer solution. In other embodiments, the microbubbles are fabricated separately and added to the vas-occlusive polymer solution.

For example, microbubbles or microspheres of the invention can be crosslinked to the polymer gel. The microbubbles or microspheres can be added separately to the gel solution and mixed to form a homogenous solution. The solution can be mixed by stirring. For example, the microbubbles can be formed by mixing a polymer-DMSO solution to form a foam solution. In other embodiments, a double emulsion method can be used (see El-Sherif, D. M., & Wheatley, M. A. "Development of a novel method for synthesis of a polymeric ultrasound contrast agent", Journal of Biomedical Materials Research Part A, (2003) 66A(2), 347-355), as well as by pumping the polymer-DMSO mixture through 2 syringes and 3-way stopcock, a method which has been employed for producing agitated microbubbles, but only in saline solutions (see Attaran, R. R, "Protocol for Optimal Detection and Exclusion of a Patent Foramen Ovale Using Transthoracic Echocardiography with Agitated Saline Microbubbles" (2006), Echocardiography (Mount Kisco, N.Y.), 23(7), 616-22). Using the double emulsion method according to the present invention, air-filled polystyrene and polyvinyl alcohol (PVA) microbubbles were produced. The mixing can also be accomplished by transferring the solution between syringes (from one to another). Further, specific size ranges of microbubbles can be isolated by differential centrifugation and added to samples of vas-occlusive polymer solutions, and the samples may be subject to ultrasound imaging. In this way, the maximum echogenicity (contrast) of the microbubbles in different size ranges can be determined.

In one embodiment, microbubbles are prepared by pumping the polymer-DMSO solution through 2 syringes connected by a 3-way stopcock with swivel male luer lock. The number of pumps can be from 1-200, such as from 1-2, 2-3, 3-4, 4-5, 5-6, and so on. The lateral and axial resolution of the gel decreases with number of pumps, indicating that more microbubbles are formed with increased number of pumps. The volume of air in the syringe loaded prior to the pumps can be varied from 0-1 mL. In one example, performing 80 pumps with a loaded air-volume of 0.75 mL yields the lowest lateral and axial resolution (highest visibility of the gel). This combination also yields the smallest decrease in visibility over time. In some embodiments, the microbubbles that are formed have no shell and comprise air. Larger microbubbles are found at the top of the polymer solution in the syringe. In another aspect, the smaller microbubbles are found at the bottom of the polymer solution in the syringe. In embodiments, the polymer-DMSO-microbubble solution is injected into a bodily duct (e.g., vas deferens).

In one embodiment, the microbubbles are prepared through the following double emulsion procedure. The polymer of interest is dissolved in organic solvent such as chloroform. Water is added and the solution is sonicated. Further, a surfactant such as PEG stearate is added to separate the water droplets within the bulk of organic solvent and polymer. The emulsion is poured into a polyvinyl alcohol (PVA) solution and homogenized. Preferably, the PVA solution is 5%, but can range from about 1% to about 80%, such as from 1% to 2%, 2% to 3%, 3% to 4%, 4% to 5%, 5% to 6%, 6% to 7%, and so on. The homogenized solution is poured into isopropanol. Preferably, the isopropanol solution is 2%, but can range from around 1% to about 50%, such as from 1% to 2%, 2% to 3%, 3% to 4%, 4% to 5%, 5% to 6%, 6% to 7%, and so on. The mixture is stirred for one hour at room temperature with stirring times that may vary. The mixture is then centrifuged to obtain a pellet of microbubbles. The pellet is resuspended in water and re-centrifuged. The solution is then lyophilized to remove the water from inside the microbubbles.

In one embodiment, perfluorocarbon gas (including perfluoromethane, perfluoroethane, perfluoropropane, perfluorobutane, perfluoropentane, and/or other such perhalocarbon gases) is contained within the microbubbles, preferably as a contrast agent. In one aspect, double emulsion is used to prepare microbubbles containing perfluorocarbon gas. In one aspect, the gas is sonicated within a polymer and organic solvent solution. In one example, the emulsion is poured into around 5% PVA, but can range from around 1% to around 50%, such as from 1% to 2%, 2% to 3%, and so on. In one aspect, the emulsion is poured into 2% isopropanol, but can range from around 1% isopropanol to around 35%, such as from 1% to 2%, 2% to 3%, and so on. In one aspect, the solution is allowed to stir at room temperature for around one hour. After around one hour, the mixture is centrifuged, re-suspended in water, and centrifuged again to obtain a pellet of microbubbles. See U.S. Pat. No. 5,695,740.

In one embodiment, the microbubbles include polyvinyl alcohol (PVA). The PVA bubbles can be cross-linked. The method by which the bubbles are prepared can include dissolving PVA in a solvent. In one example, an oxidizing agent is added, followed by double emulsion. The ends of the PVA polymeric chains are functionalized with aldehyde groups before continuing double emulsion. See Chinese Patent No. 103724638 A and U.S. Patent Application Publication No. US 20100158813 A1.

In one embodiment, the shells of the microbubbles are made of polystyrene. In one aspect, the molecular weight of the polystyrene ranges from 35,000-400,000 daltons, such as from 35,000 to 40,000 daltons, from 40,000 to 45,000 daltons, from 45,000 to 50,000 daltons, from 50,000 to 55,000 daltons, and so on.

In one embodiment, the microbubbles include one or more spermicides, such as those discussed herein. In one aspect, the microbubbles contain a degradation agent such as a reducing agent (e.g., glutathione) to assist in reversal of the polymer gel.

According to embodiments, the vas-occlusive polymer solution is formulated to have a specific porosity once it polymerizes in situ to form a gel. For example, the porosity can be tailored to allow passage of fluids (as well as constituents such as proteins, nutrients, etc.) in the vas deferens while blocking sperm cells. In embodiments, the pore diameter is less than about 3 μm (e.g. the approximate width of the head of a human sperm cell). In embodiments, the pore diameter of the formed polymer can range from 0.001 nm to 3 µm, such as from 0.001 nm to 1 µm. In other embodiments, the pore diameter can range from 0.01 nm to 100 nm. In other embodiments, the pore diameter can range from about 1 nm to about 1 µm. In other embodiments, the pore diameter can be 0.01, 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 95, 90, 95, or 100 nm. In other embodiments, the pore diameter is at least the size of an atom (0.5 nm). Specific pore sizes can be targeted to provide an optimum porosity that provides maximum flow of fluid while blocking the flow of sperm cells.

In embodiments, the vas-occlusive polymer solution of the invention is administered into the vas deferens at a rate or amount which dictates the shape and length of the vas-occlusive plug that forms. The rate of administration can be constant or variable. For example, the vas-occlusive polymer solution can be injected or infused at a rate of 0.001 cc/min (1 µl/min) to 1.0 cc/min (1 ml/min), including 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.15, 0.2, 0.25, 0.30, 0.35, 0.40, 0.45, 0.50, 0.55, 0.60, 0.65, 0.70, 0.75, 0.80, 0.85, 0.90, 0.95, and 1.0 cc/min. It is preferable that the physician injects the polymer material at a constant rate. With a relatively slow injection rate (e.g. about 0.1 to 0.2 cc/min), the polymer will form a tightly-packed, cylindrical gel. At a relatively fast injection speed (e.g. greater than about 0.50 cc/min), the polymer gel can be more string-like and may not fully occlude the vas. A pressure-controlled syringe or device may be used to ensure a constant injection speed.

Total volumes administered can vary from about 1 µl to about 1000 µl (1 ml), including 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 350, 400, 450, 500, 550, 600, 650, 700, 750, 800, 850, 900, 950, and 1000 µl.

The rate of administration and total volume administered can depend on the size of the vas deferens in terms of diameter and length of the lumen, as well as the composition and properties of the polymer solution in terms of molecular weight and concentration of the polymer, viscosity, gelation temperature, rate of polymerization, and desired length of the occlusion. Such is within the capabilities of a skilled artisan. In one aspect, the volume and rate injection is low enough that the polymer does not leak into the vas wall or rupture the vas.

In embodiments, the length of occlusion produced in the vas deferens as a result of administering the occlusive substance can range from 0.1-5 centimeters in length, including 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0 cm in length. In embodiments, the length of the occlusion formed in the vas deferens is longer than the smooth muscle fibers of the vas deferens so that the plug is not dislodged by peristaltic contraction. Preferably, the polymer gel plug formed in the vas deferens is rigid enough so that the peristaltic contraction of the vas deferens does not break, dislodge, or otherwise affect the safety and/or efficacy of the polymer gel. According to one embodiment, the injection volume and length of polymer plug that forms is determined such that the subject becomes severely oligospermic or azoospermic as determined by analysis of semen samples. Upon administration, polymerization of the vas-occlusive polymer can be monitored in real time using ultrasound.

In embodiments, ultrasound is used to image the vas-deferens and the vas-occlusive polymer during and after placement inside the vas deferens. Ultrasound based imaging is a painless and convenient diagnostic method that functions by projecting sound waves into the body, and then measuring the refraction, reflection, and absorption properties of the imaged-tissue to assess fine structure. Essentially, the way in which certain structures reflect sound waves allows for the generation of an image of the underlying organs and tissues. For instance, ultrasound imaging works best on mechanically more elastic, sound conducting tissues. Calcifications in the body (such as bone, plaques, and hardened tissues) provide degrees of acoustic impedance that makes it difficult to image structures lying below them.

Ultrasound is an ideal candidate for imaging the tissues in the male reproductive system. First, ultrasound imaging is non-invasive and safe. There is no associated ionizing radiation produced with ultrasound as found in X-Ray, PET, and X-Ray imaging. Second, the male reproductive system, specifically the scrotum, does not contain bone, plaques, or hardened tissues which limit acoustic impedance. Finally, preparing a patient for ultrasound imaging is as simple as shaving the area of interest, cleaning the area of interest, applying an ultrasound-conducting fluid interface gel to the surface of the skin, and applying the ultrasound probe in the correct orientation and position. Therefore, ultrasounds are commonly found in urology clinics and are used primarily for imaging the scrotum and penis.

Various frequencies can be used for imaging the vas deferens and/or gel, including contrast-pulse sequencing mode (7 MHZ), B-Mode imaging (14 MHZ), and frequencies in between. Other possible ultrasound modes that can be used for the inventive methods include 2D mode, fusion, harmonic imaging (THI), color mode or color power angio, CW doppler mode, PW doppler mode, M-Mode, anatomical M-mode (live or frozen image), B-Mode, color tissue doppler, PW tissue doppler, panoramic imaging, 3D/4D imaging, and dual imaging. In some embodiments, the frequencies are between 1 and 20 MHZ, including 1, 2, 3, 4, 5, 6, 7, 8, 9, 10, 11, 12, 13, 14, 15, 16, 17, 18, 19, or 20 MHZ. Additionally, the ultrasound can be delivered at different intensities, such as between 0.1 to 1 W/cm$^2$, including 0.1, 0.2, 0.3, 0.4, 0.5, 0.6, 0.7, 0.8, 0.9, and 1.0 W/cm$^2$. Additionally, the ultrasonic energy can be delivered at a specific power, such as 0 to 20 Watts of energy, including 0, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20 Watts. Additionally, the ultrasonic energy can be delivered in pulsed or continuous mode. The ultrasound can be delivered through an ultrasound unit. The ultrasound unit can be portable. An example of a portable ultrasound unit for scrotal imaging is the LOGIQ V2, manufactured by GE Healthcare (Little Chalfont, United Kingdom). Another example of an ultrasound unit for scrotal imaging is the ClearVue 350 by Philips (Amsterdam, Netherlands).

According to embodiments, various ultrasound probes or transducers can be used for ultrasound imaging the vas deferens, including sector (phased array), linear and convex transducers. Ultrasound probes and their selection have been discussed in the literature (see T. L. Szabo et al., "Ultrasound Transducer Selection in Clinical Imaging Practice", Journal of Ultrasound in Medicine, 2013, 32(4):573-582). Ultrasound transducers differ according to their piezoelectric crystal arrangement, physical dimensions, shape, footprint (aperture), and operating frequency. It is within the ability of a skilled artisan (e.g. urologist or ultrasound technician) to choose a transducer with appropriate characteristics to image the area of the vas deferens that has been isolated. A hand-held probe may be chosen for imaging that is small enough to image the vas without interfering with other aspects of the procedure such as administration of the occlusive substance.

Transducers are multi-frequency, meaning the frequency can be switched electronically between a range of frequencies (e.g. abdominal transducers have 2-6 MHz). It is important for the user to select the highest frequency which adequate depth of penetration for the anatomic area of interest. In general, the higher the frequency of the transducer, the greater than axial resolution and better the anatomic representation of the image. However, there is a tradeoff between frequency and depth of penetration. For imaging the testis, because of the close proximity of the organ to the surface of the skin, imaging can be performed with high frequency transducers such as a linear array transducer of 12-18 MHz.

There are many factors that impact the image quality. Parameters and settings may be modified by the user of the ultrasound in order to adjust and manipulate the image including: gain, time-gain compensation, frequency, depth/size, field of view, and cine function. A "good quality image" includes: (1) sufficient and uniform brightness, (2) is sharp and in focus, (3) adequate size, and (4) is oriented and labeled for documentation purposes. Furthermore, selection of a transducer is critical for maximizing image quality. Linear array transducer probes produce a rectangular image whereas a curved array transducer produces a trapezoidal shape. Linear array transducers are most commonly used in urology for imaging the testes and male genitalia. However, a curved array transducer can be helpful in visualizing both testes simultaneously.

In regards to safety, the FDA advises that the mechanical index (MI) and thermal index (TI) are kept below 1.90 and 6 degrees C., respectively.

This disclosure reports that ultrasound is the ideal imaging modality for performing a guided injection into the vas deferens. The relatively shallow depth at which the vas deferens sits allows for easy identification by a medium or high frequency ultrasound. Ultrasound is rarely used in clinical applications for imaging the vas deferens. Thus, prior to the present disclosure, methods for optimal imaging of the vas deferens were limited. To the best of the knowledge of the present inventors, ultrasound-guided, percutaneous injection into the vas deferens has never been performed. Optionally using ultrasound as guidance for performing percutaneous vas injections is critically needed because: 1) every subject has different morphometric measurements of the vas (e.g. outer and inner diameter, depth, length), 2) the physician or other professional (e.g. technician, veterinarian, etc.) performing the procedure can visualize that the needle is inside the vas lumen as opposed to the smooth muscle layers of the vas, 3) the physician can visualize the polymer solution being injected into the lumen, 4) the physician can visualize the polymer forming a hydrogel in situ in real time, 5) the physician can observe the length of the gel plug, confirming that enough of the material was injected, 6) the physician can perform routine "checkups" on the composition using ultrasound days, weeks, or months after the composition is inserted, 7) the physician can locate the gel prior to reversal, 8) the physician can perform the reversal through ultrasound-guided, percutaneous injection, and 9) the physician knows that the reversal was successful if the gel is no longer visible on the ultrasound.

According to embodiments, the physician isolates the vas deferens using a finger technique and secures it to the scrotal skin using a vas clamp. In one embodiment, an ultrasound probe is placed on the vas deferens before, during, and/or after administration of the occlusive substance. The probe can be placed parallel to the vas such that the lumen will be visualized with a longitudinal view. In this view, the length of the vas can be determined as well as the inner and outer diameter. Alternatively or in addition, the probe can be placed perpendicular to the vas deferens such that the lumen of the vas will be visualized in axial/transverse view. In this mode, it is easy for the physician to discern the depth of the vas as well as determine the inner and outer diameter length.

According to one embodiment, the physician administers a vasodilator locally in the area of the secured vas deferens prior to administration of the occlusive substance. The vasodilator diffuses to the smooth muscle of the vas and causes it to relax, thereby expanding the lumen to a dilated state. This pharmacologic dilation of the vas can facilitate the procedure by 1) providing greater visibility of the lumen of the vas under ultrasound and 2) providing a larger target for insertion of a needle or catheter into the lumen, thereby reducing the chances of "off-target" insertion into the smooth muscle of the vas. Vasodilators are known in the art, including nitric oxide donors (e.g. nitroglycerin), acetylcholine, prostaglandins, papaverine, calcium channel blockers, phosphodiesterase type 5 (PDE-5) inhibitors, and the like. The vasodilator can be administered with an anesthetic agent or be present in the solution of the vas-occlusive substance. In one embodiment, the vasodilator is administered percutaneously. In other embodiments, the vasodilator is administered topically. In other embodiments, no vasodilator is administered.

According to embodiments, a local anesthetic agent is administered in the area of the vas deferens prior to administration of the vas occlusive substance. Various local anesthetic agents are known, including amino esters such as procaine (Novocaine), tetracaine (Pontocaine), benzocaine, as well as amino amides such as lidocaine, mepivacaine, bupivacaine, and etidocaine. To avoid constriction of the vas deferens lumen, it is preferred that the local anesthetic agent be substantially devoid of vasoconstrictive activity, and that no vasoconstrictive agents such as epinephrine be administered with the anesthetic. The anesthetic can be administered topically or percutaneously.

Once the lumen is visualized, the physician percutaneously inserts a needle, cannula, catheter, or needle-catheter into the lumen under optional guidance of ultrasound imaging and administers (e.g. injects) the occlusive substance (e.g. polymer solution) into the lumen. The injection process may be performed towards the direction of the testes, which would be against the flow of seminal fluid and assist in gel formation, or in the direction of the prostate. The region of the vas where the injection can be performed is either in the scrotal region or supra-scrotal region before the vas extends into the pre-pubic region. An echogenic needle can be used, which facilitates visual confirmation that the needle is inside the lumen via ultrasound before administration. Alternatively, an ultrasound with magnetic field needle guidance such as the eZono® 4000 (eZono AG, Jena, Germany) can also be used to guide the needle more precisely into the lumen in axial mode. The ultrasound may also be a hand-held, portable ultrasound.

If the polymer is echogenic, it will be seen being injected into the lumen. Then, the physician will be able to witness the polymer form a hydrogel in the vas deferens in real-time.

After the gel "plug", or occlusion, forms, the physician can confirm the procedure was done properly by ultrasound imaging the gel. Axial mode can be used for viewing to determine if the gel completely occluded the vas, whereas longitudinal mode can be used determining the length of the vas-occlusive gel plug. In this way, the dimensions (e.g. length, width, and diameter) of the occlusion can be determined through ultrasound imaging. If the occlusion is not of sufficient size in terms of diameter and length, additional material can be administered inside the vas deferens lumen, until the physician confirms administration of an appropriate amount of vas-occlusive material through ultrasound imaging.

Thus, one particular embodiment of the invention provides a method of vas-occlusive contraception which includes:

Non-surgically or surgically isolating the vas deferens in the scrotum such as by using a three-finger type technique;

Optionally, administering anesthesia to the subject, such as by administering local anesthesia to the vasal nerve region (e.g. vasal block);

Raising the vas deferens and securing it, such as by securing the vas deferens to the scrotal skin using a vas-clamp, making the vas as superficial as possible;

Placing an ultrasound probe on the vas deferens and administering ultrasonic energy to the vas deferens to visualize the vas deferens lumen in longitudinal and/or axial view; and, by way of ultrasound imaging:

Measuring one or more dimensions of the vas deferens lumen;

Placing a needle into the vas deferens and confirming placement of the needle or catheter or a portion thereof into the lumen;

Percutaneously administering a vas-occlusive polymer solution into the lumen;

Confirming formation of a polymer occlusion inside the lumen; and

Determining one or more dimensions of the occlusion in longitudinal and/or axial view.

The above procedure can then be repeated on the contralateral side.

Figure 1B:
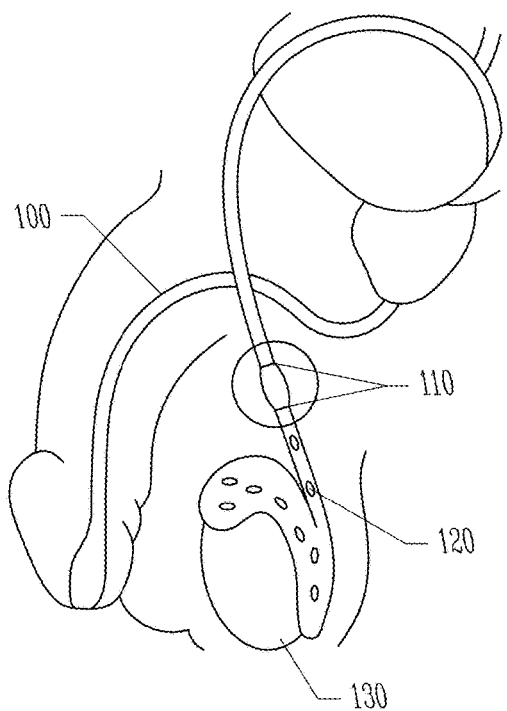
FIG. 1B is a diagram showing the result of the method of FIG. 1A (semen; no sperm (100), vas occlusive plug (110; lumen is occluded), sperm cells (120), testicle (130)).

For example, FIG. 1A is an illustrative diagram showing an embodiment of a procedure of the invention in which a vas clamp is used to hold the vas deferens close to the scrotal skin. First, the general area of the scrotum is shaved and an ultrasound-conducting fluid interface gel is applied to the scrotum (not shown). Then, an ultrasound probe is placed over the vas, ultrasonic energy is administered, and the physician percutaneously injects the vas-occlusive substance into the vas deferens optionally under the guidance of ultrasound imaging. FIG. 1B is an illustrative diagram showing occlusion of the left vas deferens by way of a vas occlusive plug after the procedure is performed such that sperm cells are blocked from progressing through the lumen of the vas deferens.

It is predicted that the inventive methods will be significantly quicker than a typical vasectomy due to the fact that no incision or exteriorization of the vas is required. Furthermore, the inventive methods skip the step of removing the sheath that surrounds the vas, which occurs during vasectomy (also adding a layer of safety which is of issue with surgery).

As discussed herein, different aspects of the procedure include length of the procedure, the use of local anesthesia, using a vas-clamp or holding vas superficially to skin with fingers, rate of injection or infusion, needle gauge size and/or length, syringes that can be used, vas deferens characteristics, such as depth of vas from skin, left or right vas, inner and outer diameter of vas, length of vas that is visible, which portion of vas is administration performed, which direction is the administration performed (towards testes or prostate), and ultrasound properties, such as machine specs, probe specs, frequency, intensity, depth, mechanical index, and gain. Such are within the capabilities of a skilled artisan.

The amount of occlusive substance (such as an echogenic gel) to be administered to a subject can vary based on several different criteria, including the duct or vessel where it is administered, the size of the lumen, the concentrations of the various components of the substance as administered, the molecular weight of the polymer in the gel, the volume of the gel solution that is administered, and the size of the occlusion that the physician or person who is administering the gel solution is trying to achieve.

For example, ultrasound imaging of the vas deferens is particularly important for determining the dimensions of its lumen, which determines the amount of substance administered. Administration of an insufficient amount of substance can result in the vas deferens only being partially occluded, while administration of too much substance (particularly at a high rate) can rupture the vas deferens. Thus, according to one embodiment, ultrasound imaging is used to determine the morphometrics and dimensions of the subject's vas deferens, including the inner luminal and outer total diameters, thickness of tunics, and length of the vas deferens. As use of the method increases, a robust database can be generated that will provide valuable information regarding the anatomical and physiological feature of the human male reproductive tract. This new information could potentially further novel advancements in male reproductive health, and will help to standardize known anatomical information on the vas deferens. In 107 men in China, it was reported that the average inner diameter was 0.56 mm and the average outer diameter was 2.17 mm (Liu, X. et al.). However, various other studies have shown that the inner diameter can be as little as 0.31 mm and can dilate as large as 1.8 mm (Liu, X. et al.). The injection volume of the occlusive agent that should be delivered to each individual is a function based on several criteria including: the size of the individual's vas lumen, the concentration of the polymer, the molecular weight of the polymer, monomer ratio of the polymer, injection speed, and desired plug length. Ultrasound allows for the determination of the patient's lumen and plug length. The same paper by Liu et al., reports that the mean rupture volume is around 0.05 mL for 1 cm of vas. During the inventive procedure, ultrasound can be used to ensure that the substance has occluded the lumen and that additional material should not be injected in order to prevent rupturing of the vas.

The vas-occlusive substance (e.g. polymer solution) can be administered into the as lumen by hand through a standard hypodermic needle and syringe, such as those manufactured by Becton Dickinson (Franklin Lakes, N.J.). In one embodiment, an injection device is used for the procedure wherein said device maintains an almost constant injection speed and volume during the injection. In one embodiment, this injection device is a pressure-controlled syringe. The polymeric composition can be provided in a pre-filled syringe, vial, or other suitable container. Alternatively, the vas deferens can be cannulated or catheterized by way of insertion of tubing and a vas-occlusive polymer can be administered mechanically through the use of an infusion pump, such as those manufactured by Cole-Parmer (Vernon Hills, Ill.). The use of an infusion pump facilitates precise, controlled flow rates and quantities of vas-occlusive polymer solution into the vas deferens lumen.

In embodiments, the vas-occlusive polymer is monitored at various times following administration. For example, it can be monitored using ultrasound at various times, including, days, weeks, months, and years after administration to determine whether it is still there and to monitor its integrity. Monitoring is useful for determining that the vas-occlusive polymer has polymerized to form a gel, the location of the gel, stability of the gel, effectiveness of the gel, and longevity of the gel, as well as its use as a contraceptive. In addition, ejaculates of the subject can be monitored and sperm counted and measured for viability, motility, activity, etc. and compared to the ultrasound results. Such monitoring can determine the need for a follow-up procedure, such as re-administration of the vas-occlusive polymer to the subject.

In embodiments, the longevity or stability of the polymer gel is estimated by counting the number or concentration of microbubbles inside the gel. The longevity or stability of the polymer gel can be further estimated by determining the echogenicity of the polymer gel using ultrasound. Alternatively, the longevity or stability of the polymer gel can be evaluated by observing the shape, size, or attachment of the polymer gel to the lumen of the vas deferens by way of ultrasound.

In embodiments, solutions of the invention are formulated with microbubbles which incorporate an agent which renders sperm immotile, infertile, or inviable. The agent can be incorporated inside the microbubbles or conjugated to the microbubbles.

Another embodiment of the invention is a method of delivering of an agent to the lumen of the vas deferens. The method includes non-surgically or surgically isolating the vas deferens of a subject, administering a solution into the lumen of the vas deferens, and applying ultrasonic energy at a frequency which is capable of lysing microbubbles present in the solution, thereby releasing the agent into the lumen of the vas deferens. Alternatively, the microbubbles may be allowed to slowly dissolve without the use of ultrasound such that the agent is released to the lumen at a constant rate over time. In this way, the vas-occlusive polymer provides both a physical barrier to the passage of a sperm as well as targeted inhibition of sperm cells.

For example, in one embodiment, focused ultrasound is applied at a particular frequency which causes the microbubbles to vibrate. At a particular threshold of intensity and/or frequency, the microbubbles can be destroyed, which can cause a local shock wave, resulting in cavitation and lysing of the gel. Thus, the use of ultrasound can provide a non-invasive method of reversing the vas-occlusive contraception provided by the invention. Accordingly, one embodiment of the invention provides a method of reversal of a vas-occlusive contraception comprising applying ultrasonic energy to a vas-occlusive gel plug at a frequency and/or intensity that is capable of destroying microbubbles inside the vas-occlusive gel plug, thereby lysing and destroying the occlusion.

In one embodiment, a level of ultrasonic energy needed for microbubble cavitation is determined. For example, a detector transducer receives a scattered level of ultrasonic energy, indicative of stable cavitation. Accordingly, a method for in vitro or ex vivo testing of microbubble cavitation is used to determine acoustic pressures necessary for reversal. In one aspect, the gel with microbubbles is precipitated in dialysis tubing. By way of example, the gel with microbubbles is precipitated in an excised vas deferens or synthetic vas deferens tissue, and an ultrasound probe is applied at varying frequencies, wherein for each frequency, the amount of gel lost is measured. Once a measurement is recorded which is expected to adequately reverse, de-precipitate, liquefy, dissolve, or flush out the polymer gel, such a frequency can be used to reverse, de-precipitate, liquefy, dissolve, or flush out the polymer occlusion in a subject.

An additional embodiment of the invention includes a method of reversal of a vas-occlusive contraception comprising non-surgically or surgically isolating the vas deferens and administering a solvent or solution in the lumen of the vas deferens that is capable of dissolving a vas-occlusive polymer plug disposed in the lumen of the vas deferens. For example, the method of reversal may rely on ultrasonic imaging to determine the location of the vas-occlusive polymer plug in the vas deferens. Then, the vas deferens may be isolated according to the three-finger technique and use of a vas-clamp as previously described. Then, a solvent or solution which is capable of dissolving the polymer may be administered into the lumen of the vas deferens by way of percutaneous injection. Alternatively, the solvent or solution can be used to "flush out" the occlusion. For example, the solvents can include DMSO and the solutions can include sodium or potassium bicarbonate. In one aspect, the solution has a pH from 8-9. As an alternative to bicarbonates, other alkaline solutions can be used. Anywhere from 0.01-3 cc of solvent or solution can be injected into the lumen of the vas deferens, such as 0.01 to 0.02 cc, 0.02 to 0.03 cc, 0.03 to 0.04 cc, and so on. However, the rate and volume of injections are limited such that the injection force does not rupture the walls of the vas deferens. The dissolution of the polymer occlusion can then be monitored in real time using ultrasound. Absence of the occlusion and patency of the vas lumen can be confirmed via ultrasound imaging, and ejaculates can be monitored post-procedure to determine restoration of sperm counts in the ejaculate. In this way, successful reversal of contraception can be confirmed.

In some embodiments, reversal of contraception is performed surgically. The vas deferens can be exteriorized, a small slit can be made, and the occlusion may be able to be pulled out (especially in the case of silicone devices). In some embodiments, the occlusion may be mechanically reversed using a miniature drill. If these methods are ineffective, the segment of the vas containing the gel may be ablated and re-anastomosed in a procedure identical to vasovasostomy.

According to additional embodiments, compositions and methods are provided that provide for radio-frequency, photoacoustic, and/or infrared detection of the occlusive substance in addition to ultrasound. For radio-frequency detection, particles include but are not limited to gold or radiofrequency identification (RFID) powder, both of which can be recognized by a recognition device/reader. RFIDs come in the form of chips or elements that are subjected to a radio frequency by a reader probe. Different RFIDs have been manufactured, including RFID powder, which has a surface area of around 0.3 $mm^2$ (see U.S. Pat. Nos. 8,440,487; 8,766,853; and 8,933,784). The powder may be added to a vas-occlusive polymer solution and incorporated into the contraceptive once the gel is formed. Similarly, a dye could be incorporated into the contraceptive for infrared imaging.

Thus, embodiments provide occlusive substances that are (1) effective long-term, (2) reversible, and (3) detectable by (i) ultrasound, (ii) radio-frequency, (iii) infrared, and/or (iv) photoacoustic imaging. Embodiments of the present invention include an occlusive substance which includes at least one polymer, a solvent medium, and at least one imaging agent, such that the occlusion is detectable when the substance is injected into a body cavity or lumen. Fields of use include, but are not limited to treatment (e.g., occluding) of the vas deferens, fallopian tube, aneurysms, blood vessels, ducts, tumors, and organs.

In one embodiment, the polymer is modified by adding or cross-linking a dye including but not limited to fluorescent dyes (e.g., atto680). In one aspect, the polymer gel modified with the dye can be reversed through exposure to a laser.

In one embodiment, the occlusive polymer gel contains microbubbles, radio-frequency detectable particles, ultrasound-detectable particles, photoacoustic-detectable particles, or a combination of them.

In one embodiment, the polymer gel contains particles that allow for the gel to be detectable with radio-frequency. For example, the particles may be gold nanorods, or the particles may be RFID chips, elements, powder, or some other means of imparting RFID properties to the polymer gel. In one aspect, the RFID is active or passive. In one aspect, if the RFID is active, it could be written on as well as read. In one aspect, if the RFID is active, it could be functioning constantly. In one aspect, if the RFID is passive, it does not require a battery.

In one embodiment, the gold nanorods encapsulated in the polymer gel are ultrasound visible. In one aspect, the gold nanorods have a polymer coating. In one aspect, the polymer coating is functionalized with an antibody or DNA. In one aspect, the gold nanorods have a silica coating. In one aspect, the gold nanorods can be excited with photoacoustic energy.

In a preferred embodiment, the RFID properties are imparted to the polymer gel in the form of RFID powder. The RFID powder may be distributed or added to the polymer solution such that when a gel forms, the RFID element would be dispersed within the gel composition. In one aspect, the RFID powder is 0.05 mm×0.05 mm×0.0005 mm. In one aspect, the RFID powder responds to 2.45 GHz frequency. In one aspect, the RFID powder has a 128-bit ID. The RFID powder may be placed or distributed at different points inside the polymer gel, wherein it may be dispersed randomly, non-randomly, uniformly, non-uniformly, or in some other manner. In one aspect, the RFID is fixed into place inside the gel. In one aspect, tens, hundreds, thousands, or more RFID powder granules or elements are implanted and/or dispersed inside of the polymer gel. In one aspect, different gauge needles are used to implant different amounts or sizes of RFID elements. In a preferred embodiment, a 34 gauge needle is used to implant the RFID, and the RFID element or powder is placed inside of the vas deferens.

In one aspect, the RFID element or RFID powder is contained within another substance or material, such as a casing or solution; for example, to make the RFID more biocompatible. In one aspect, the casing can be visualized, identified, or otherwise detected using ultrasound. In one aspect, the casing does not severely interfere with the tag's response or reading. In one aspect, the casing is chemical resistant to the gel that surrounds it. In one aspect, the casing material is inert. Preferably, the casing is not so thick that the RFID element is no longer functional or that the gel no longer has RFID properties.

In one embodiment, the silicon substrate that is the base of the RFID chip is replaced with a glass substrate, making the tag ultrasound visible.

In one embodiment, RFID technology is used to detect the presence of a substance within a body, including a vas-occlusive gel or some other occlusive gel. In one aspect, RFID technology is used to detect the formation of a polymer gel occlusion in the body. In one aspect, the polymer gel occlusion to be detected by RFID technology is inside the vas deferens. In one aspect, the polymer gel occlusion is inside the fallopian tubes. In another aspect, RFID technology is used to detect the presence, stability, longevity, effectiveness, and/or other property of an occlusive polymer gel hours, days, months, or years after the polymer gel is implanted. RFID technology may be used to detect changes in the presence, stability, longevity, effectiveness, and/or other property of a bodily substance over time.

In one embodiment, RFID technology is used to detect degradation of a substance in the body. In one aspect, said substance is a polymer gel. In one aspect, the degradation can be tracked over time. In one aspect, each tag contains a rectifier circuit which converts the signal into power for the device. In one aspect, the circuit can be used to power other devices. In one aspect, the RFID element can be activated to release a degrading agent, such as, for example, a reducing agent (e.g., a peptidase). In one aspect, RFID technology can be used to trigger the release of spermicide, antibacterial agents, or steroidal agents.

In one embodiment, RFID technology is used to detect whether the polymer gel was reversed. For example, when the polymer gel is reversed, de-precipitated, liquefied, dissolved, or flushed out, the RFID elements are excreted through urination or other means of removing foreign bodies (e.g., RFID elements) from the body. In one aspect, reversal is confirmed by the lack of RFID tag response.

In one embodiment, a multi-tag system using RFID technology is used. In one aspect, multiple RFID frequencies are used to differentiate tags. In one aspect, different frequencies are used to differentiate segments of a substance (e.g., polymer gel). In one aspect, multiple tags are used as backups. In another aspect, a multitude of tags are used to generate a higher response.

In one embodiment, different subjects can receive polymer gels having different RFID tags in order to, for example, differentiate subjects. In one aspect, this method is used to track patients. In one aspect, since each RFID has 128-bits of information, 238 different IDs can be created. In one aspect, each subject can have their own RFID tag or other identifier.

In one embodiment, a reader is used that can detect RFID technology or elements through human tissue. In one aspect, the reader can detect RFID powder. In one aspect, the reader can detect gold nanorods. In one aspect, the reader can detect RFID elements (e.g., powder) within or dispersed in a polymer gel. In one aspect, the reader can detect RFID elements (e.g., powder) within a polymer gel within a bodily duct (e.g., vas deferens). In one aspect, the RFID reader can examine, read, or detect the polymer gel within the vas deferens with less interference when the vas deferens is superficial to the scrotal skin.

In one embodiment, the reader can be an attachment for phones, computers, tablets, portable electronic devices, etc. In one aspect, the reader attachment would rely on the phone, computer, tablet, portable electronic device, etc. to process and/or analyze the data, while the reader may, for example, only record raw data. In one example, the reader is personalized so that it can only work for a certain RFID tag or person. In one aspect, a reader is designed for detecting and/or tracking the presence, stability, effectiveness, longevity, and/or other properties of a polymer gel containing RFID technology (e.g., RFID powder). In one aspect, the reader attachment allows the user to track his/her RFID implant, without visiting a physician or other healthcare professional.

In one embodiment, the gel can be imaged by an infrared detection device. In one aspect, the polymer gel contains an infrared dye, such as a clinical dye ICG. In one aspect, the polymer gel contains gold for infrared detection. In one aspect, a laser is used at low power to excite the fluorescence for detection. In one aspect, the excitation is at a 750-800 nm range. In one aspect, the emission filter is set with 20-60 nm shift. In one aspect, the infrared detection device is a camera. In one aspect, the detection device has a laser pointer. In one aspect, the detection device has a mated interference filter. In one aspect, the detection device has a camera chip. In one aspect, the camera chip is connected to a phone, computer, laptop, or other electronic device. In one aspect, the signal from the pigment of the skin is attenuated.

The methods and compositions of the invention can be used to provide long-lasting yet reversible contraception for human males, as well as male animals such as pets, farm animals, zoo animals, and wildlife. The methods have numerous advantages over other forms of contraception such as vasectomy or neutering in terms of reversibility, costs, ease of administration, and lack of complications. Further, as the method involves a one-time administration of a long-lasting contraceptive agent, the method lacks the issues associated with contraceptive drugs or hormones such as adverse effects and lack of compliance.

The methods offer several medical benefits over vasectomy due to the fact that they are significantly less invasive and do not require surgical ablation of the vas deferens. First, a percutaneous injection has been shown to be less painful than incision and exteriorization of the vas as during vasectomy and has less chance for hematoma and infection. Secondly, it is believed that implanting a polymer hydrogel may reduce the chance for granuloma formation; if the pores of a hydrogel allow fluids and small molecules to travel through, this may prevent sperm from extravasating and anti-sperm antibodies may decrease or build up at a slower rate. Thirdly, by allowing fluids to travel through or around the hydrogel, then hydrostatic pressure in the vas deferens will decrease. The buildup of hydrostatic pressure in the vas and epididymis after vasectomy is believed to be a major cause of post-vasectomy pain syndrome. Pain from post-vasectomy pain syndrome is thought to be also caused by sperm granulomas. Altogether, the methods potentially reduce the chance for a patient to develop granulomas, hematomas, pain, or post-vasectomy pain syndrome.

Further, around 6% of men who receive a vasectomy later undergo vasovasostomy (or vasectomy reversal). Vasovasostomy are difficult microsurgery procedures that requires general anesthesia, is expensive, and long (~3 hours). Research has shown that patients who have a vasectomy reversal >5-10 years after vasectomy decrease their chance for having offspring from 95% to 65% for reasons including the buildup of anti-sperm antibodies. Embodiments of the present invention provide methods of reversal that are similar to the contraceptive methods except instead of a polymer solution being injected into the vas lumen, a different solution is injected percutaneously into the lumen that de-precipitates, dissolves, or liquefies the occlusive substance. The present reversal methods are significantly shorter and easier to perform than vasovasostomy. After reversal is performed, the physician may confirm the procedure was successful based on if the gel is imageable or not on the ultrasound.

The following Examples describe particular implementations of the invention. They are intended to further illustrate the invention and should not be used to limit the scope of the invention.

Example 1

Imaging of the Human Vas Deferens with Ultrasound

Background:

The non-surgical procedure disclosed herein to inject the echogenic gel is novel and is significantly different from the no-scalpel vasectomy (the current gold standard) as well as the procedure used to administer RISUG and VASALGEL. To distinguish this minimally invasive procedure from the vasectomy or injection of other vas-occlusive contraceptives, this procedure from hereon in, is known as VASINTOMY™. In the no-scalpel vasectomy, the three-finger technique is used to locate the vas at which point a local anesthetic is injected into the scrotum and the vas. A small incision is made and the vas deferens is exteriorized. The sheath surrounding the vas is removed, and vas is ablated. After the ablation, the vas is placed back inside the scrotum. The procedure is performed on both sides. The injection of vas-occlusive contraceptives (RISUG, VASALGEL) is similar to the no-scalpel vasectomy, except for the injection of a gel into the lumen of a vas instead of ablating the vas.

A limitation of this procedure is that there is no way to visualize the gel or the injection. The lumen of the vas deferens is on average 0.4-0.6 mm in diameter. It is impossible to know if the urologist injected the gel correctly into the lumen, or if it was injected into the smooth muscle layers of the vas. Finally, there is no way to locate the gel in the vas post-procedure or monitor its effectiveness, stability, or longevity. Primary market research has also revealed that the main factor why men choose not to get a vasectomy is the surgical procedure.

Thus, a novel aspect of the invention is the VASINTOMY™ or ultrasound-guided, percutaneous injection of an echogenic contraceptive substance. This procedure uses ultrasound imaging to guide the injection into the lumen, at which point the release and precipitation or polymerization (or otherwise formation of a solid or an occlusion) of the gel can be visualized due to its echogenicity. The VASINTOMY™ requires no incisions, scalpels, or sutures. In this procedure, the three-finger technique can also be used to locate the vas and then a local anesthetic is injected. Then the vas is attached to the scrotum using a vas-clamp, making it as superficial as possible. The urologist places a standard ultrasound probe against the vas to see the lumen, and then the needle is guided through the skin into the lumen. The needle becomes visible under ultrasound once inside the lumen. Next, the injection is performed and the echogenic gel is released. Once formed or precipitated, the gel can be imaged again to guarantee the procedure was performed successfully. This procedure allows for real-time imaging of the contraceptive during the injection.

For proof-of-concept of the VASINTOMY™, an IRB was filed and approved by Dr. Ryan Smith, a urologist at the University of Virginia Urology Clinic. In this IRB, Dr. Smith clamped and imaged the vas of men receiving the vasectomy procedure. If the lumen was visible under ultrasound at high resolution, Dr. Smith was confident that he could do the injection percutaneously.

Objectives:
1. Prove that the lumen of the vas deferens can be visualized with high resolution after clamping it to the scrotal skin
2. Observe the lumen in various views.
3. Determine the time for the urologist to observe the lumen with high resolution.

Figure 2:
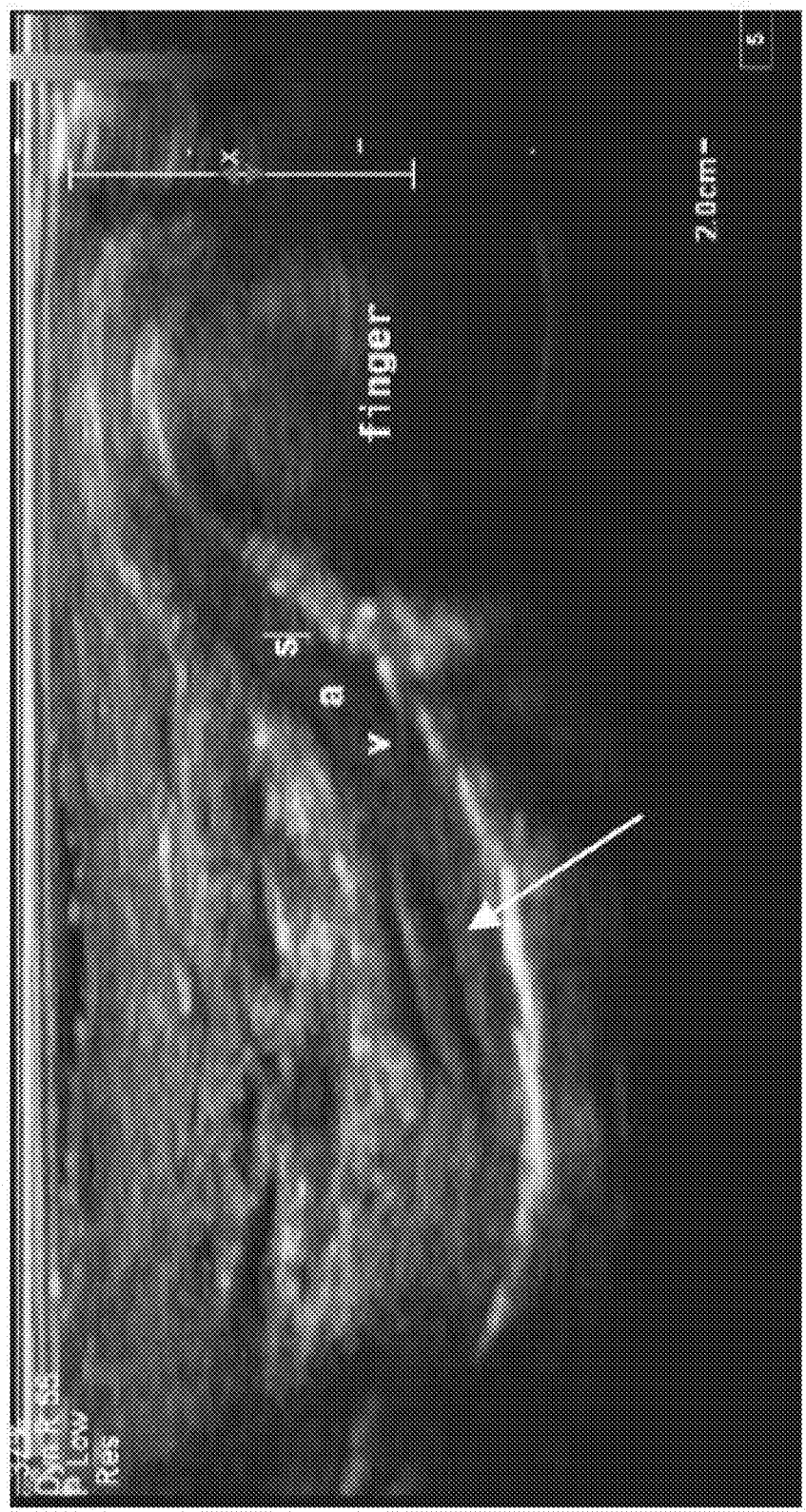
FIGS. 2, 4-7, and 10 are longitudinal ultrasound images of the vas deferens in a human male.
Figure 3:
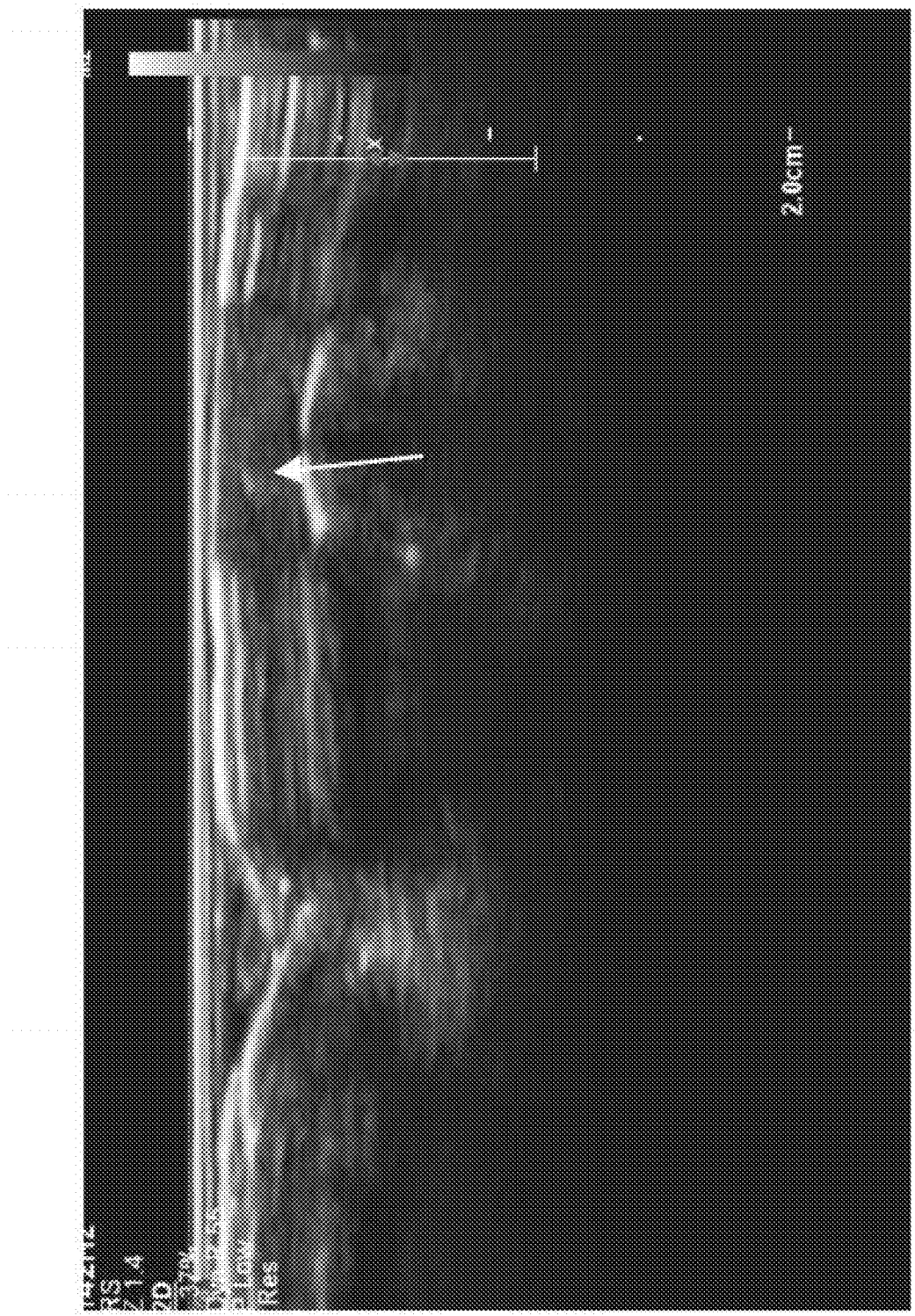
FIGS. 3, 8, and 9 are axial ultrasound images of the vas deferens in a human male.

Methods:

The vas was isolated using the three-finger technique, local anesthesia was injected into the area, and the vas was clamped to the scrotal skin or held the vas superficially to the skin using Dr. Smith's thumb. Then, Dr. Smith used a Philips HD XE 11 ultrasound with L15-7io probe (also known as hockey-stick probe) and placed the probe longitudinally to the vas Results:

In this clinical study, Dr. Smith from the UVA Urology Clinic took ultrasound images of the male patient's vas deferens prior to vasectomy. Dr. Smith stated that it took less than ten seconds to identify the lumen on the ultrasound. The ultrasound probe was positioned to view the vas in both transverse (FIG. 2) and axial view (FIG. 3). In both of these cases, the lumen could be seen clearly (marked by arrows).

Figure 4:
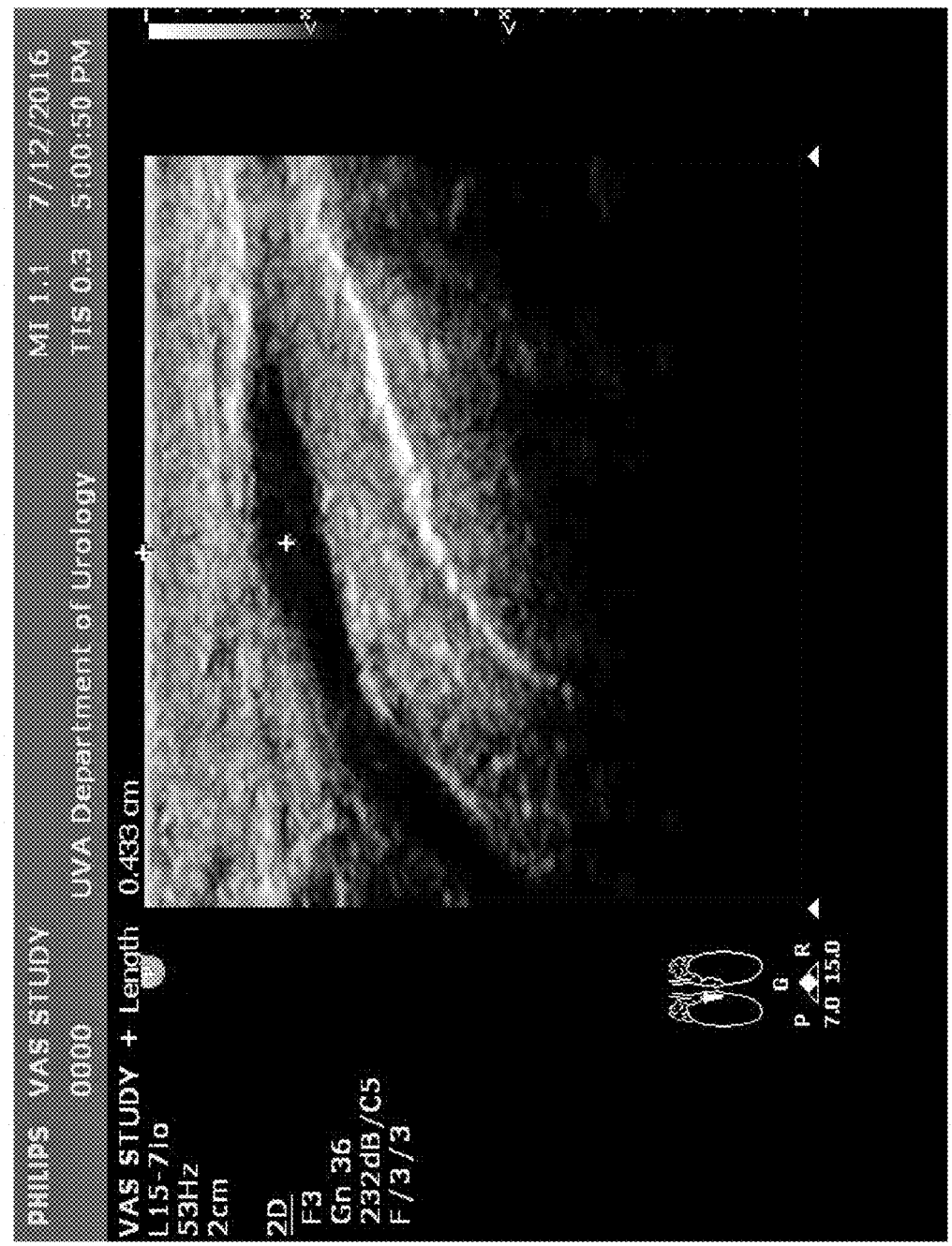

The ultrasound image of FIG. 4 shows that the lumen of the vas deferens is distinguishable based on the fact that it has a black void running the length of the lumen compared to the tissue surrounding the vas. Using a measurement tool on the ultrasound (shown by plus signs), Dr. Smith measured the depth of the vas (from skin to mid-lumen) to be around 0.4 cm or 4 mm. Thus, the vas is required to be as superficial for high resolution, high-frequency imaging.

Figure 5:

As shown in the ultrasound image of FIG. 5, Dr. Smith determined the inner lumen of the vas deferens to be 1.90 mm in the same patient. This corresponds similarly to reported literature of the dilated inner lumen diameter.

Figure 6:
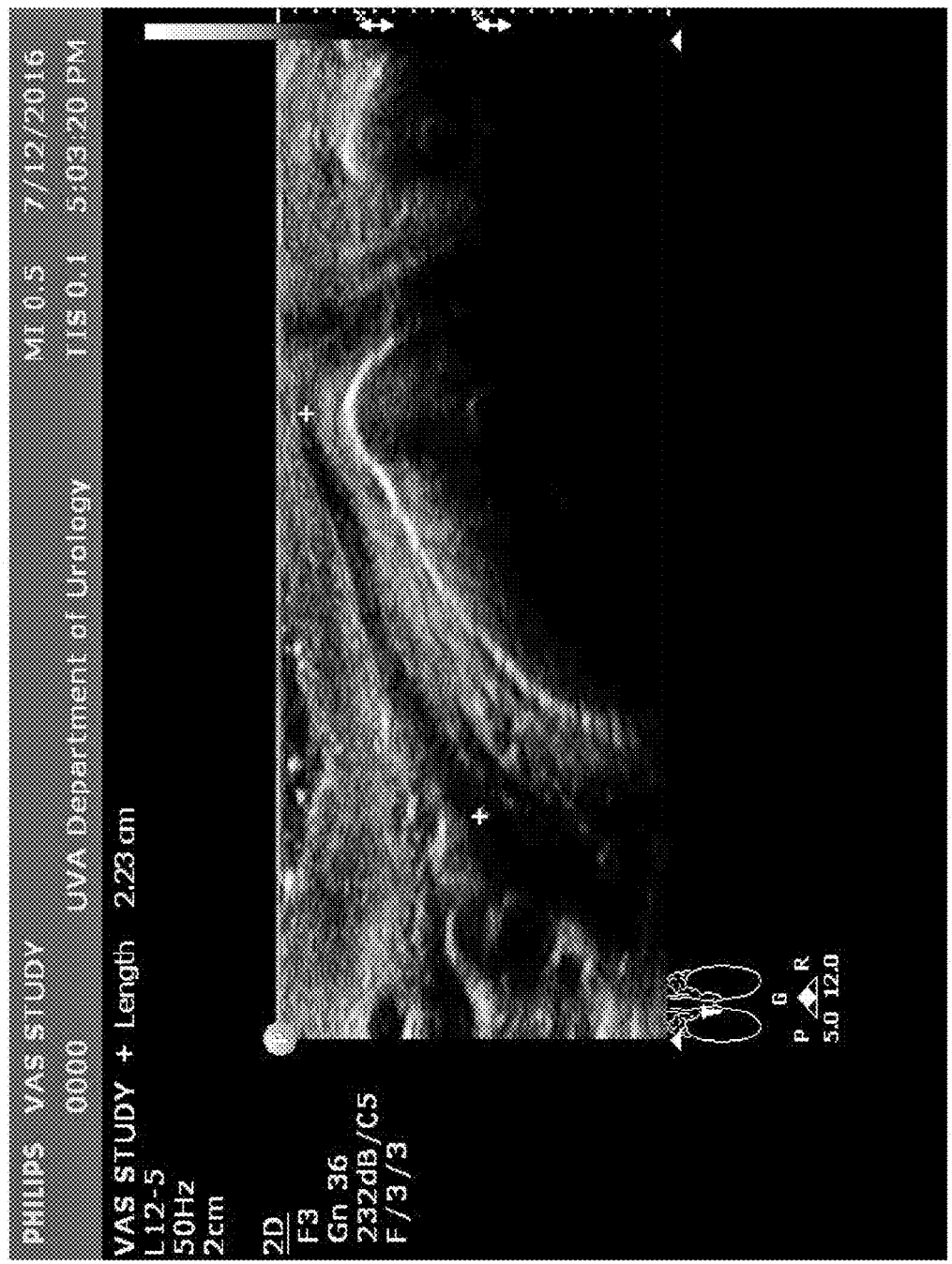

As shown in the ultrasound image of FIG. 6, Dr. Smith was also able to visualize the lumen of the vas deferens in the same patient using a lower frequency probe L12-5. A length of 2.23 cm of the vas lumen could be visualized in this image. Thus, if a polymer gel was implanted during this imaging, up to 2.23 cm of the gel would be able to be visualized.

Figure 7:
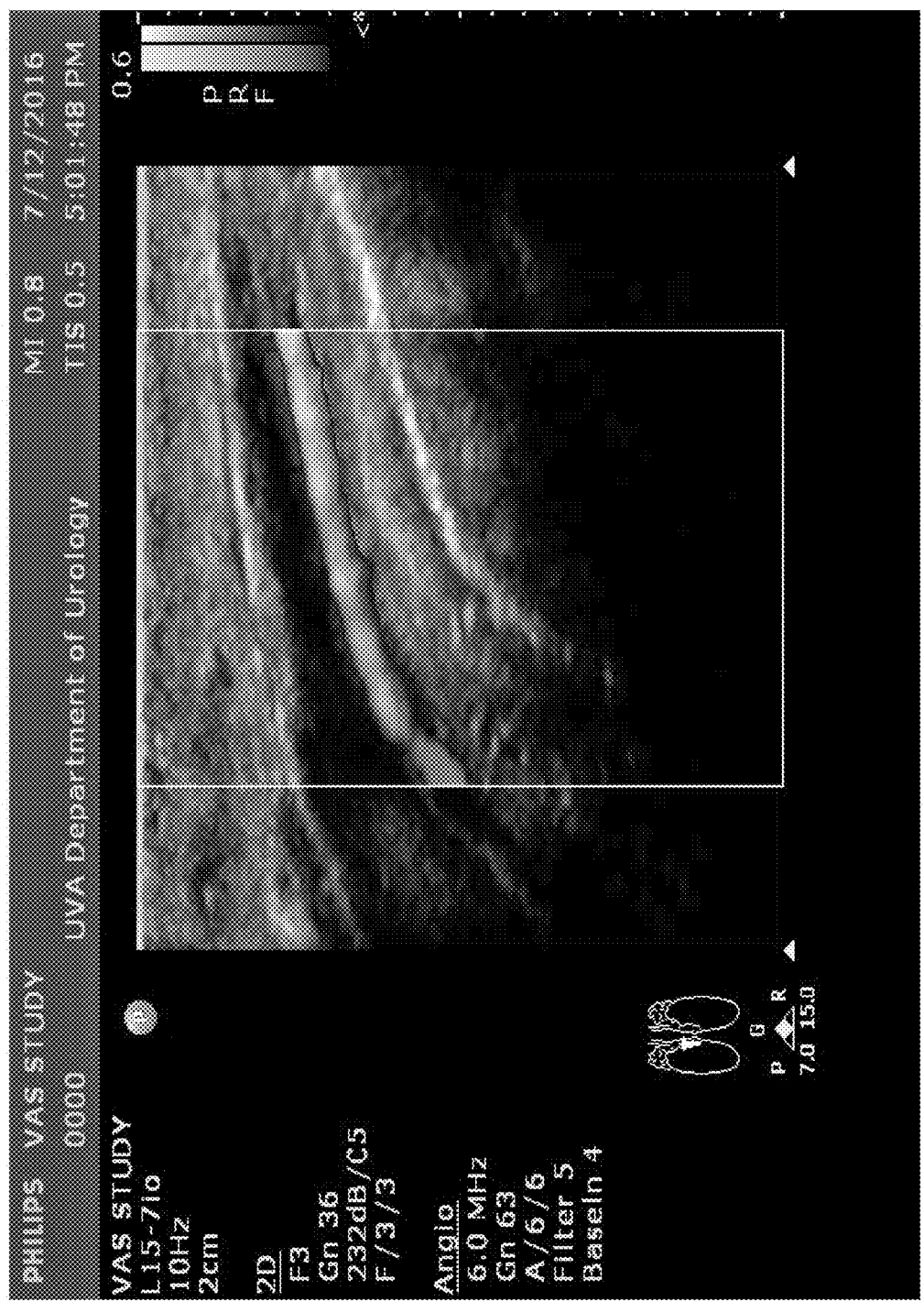

The image in FIG. 7 shows a Doppler ultrasound and color flow mapping of the artery that lies adjacent to the vas deferens in the spermatic cord. Color flow mapping using Doppler ultrasound allows real-time mapping of blood flow patterns. Color Doppler ultrasonography allows for the evaluation of the velocity and direction of an object in motion. A color map may be applied to the direction. The most common color map uses blue for motion away from the transducer and red for motion towards the transducer. The velocity of motion is designated by the intensity of the color. The greater the velocity of the motion, the brighter the color displayed. In urology clinics, Color Doppler is useful for characterizing blood flow in the kidneys, testis, penis, and prostate. In most clinical circumstances, the angle between the transducer and direction of motion should be less than or equal to 60 degrees. This figure shows that Color Doppler may also be applied for imaging the vas deferens to distinguish the tube from the artery. This is a precautionary method that the physician can utilize to prevent him or her from injecting the polymer material into a blood vessel.

Figure 8:
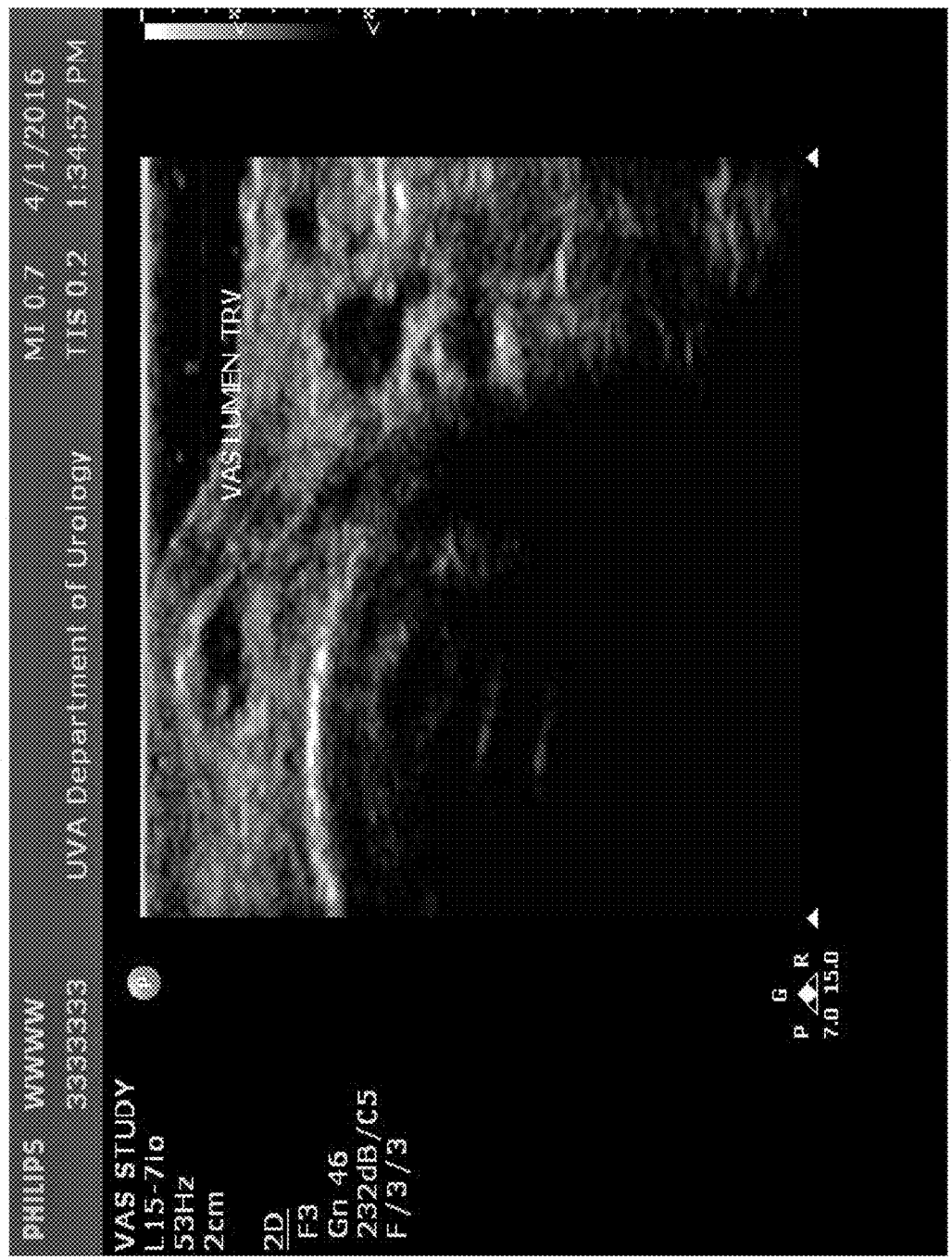

In axial mode imaging using a high frequency probe (L15-7io), as per FIG. 8, the physician is able to discern the vas lumen (on the left hand side) as opposed to the arteries and veins (on the right hand side). The vas can be distinguished by the extensive smooth muscle layers that surround it. Around 90% of the vas deferens is made of smooth muscle. In this view, the physician can confirm that he or she successfully isolated the vas deferens using the three-finger technique from the arteries and veins in the spermatic cord.

Figure 9:

FIG. 9 is another axial ultrasound image of a patient's vas deferens lumen using a high frequency probe. Dr. Smith determined that the inner lumen diameter was approximately 1.41 mm in this patient.

Figure 10:
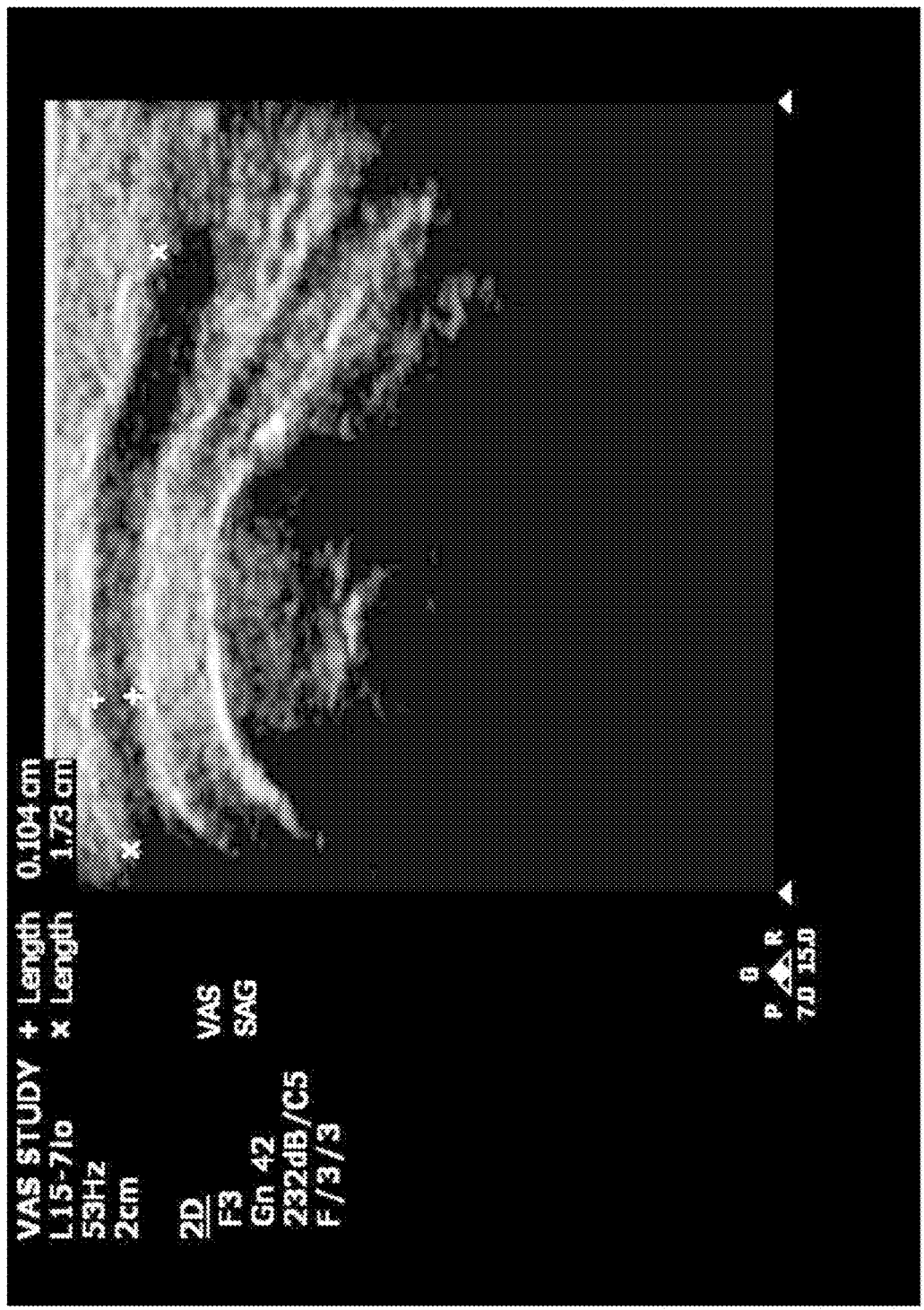

FIG. 10 is a longitudinal ultrasound image performed in the same patient. In this image, the inner diameter is shown to be approximately 1.04 mm (much smaller than the other patient's) and the length of the vas visible is 1.73 cm. A hollow segment of the artery is also visible under the vas deferens. The vas can easily be distinguished by its large hollow lumen and large segment of smooth muscle.

Discussion

This experiment tested and proved the feasibility of using a clamp and ultrasound to observe the lumen of the vas deferens with high resolution. It took Dr. Smith only ten seconds to locate the lumen. He was confident that the ultrasound guidance would allow for the injection to be performed percutaneously. This VASINTOMY™ procedure can potentially reduce the surgical complications associated with a vasectomy such as infection, granulomas, hematomas, and post-vasectomy pain syndrome. The VASINTOMY™ is much less invasive and quicker than a vasectomy.

If the urologist is injecting a solution into the lumen to reverse the contraceptive gel, whether by dissolving or flushing it out, the procedure can also be performed through the ultrasound-guided, percutaneous injection. Therefore, the VASINTOMY™ reversal will be much quicker, simpler, and less invasive than the vasectomy reversal.

Example 2

Ultrasound Imaging of Synthetic Vas Deferens

This experiment involved ultrasound imaging synthetic vas deferens (purchased from SynDaver Labs (Tampa, Fla.)), which are commonly used for practicing vasectomy and vasovasostomy procedures. The synthetic tissue has been validated to have similar mechanical properties to human vas tissue. Thus, the synthetic vas deferens makes for a good ex vivo model for the VASINTOMY™ procedure.

Figure 11:
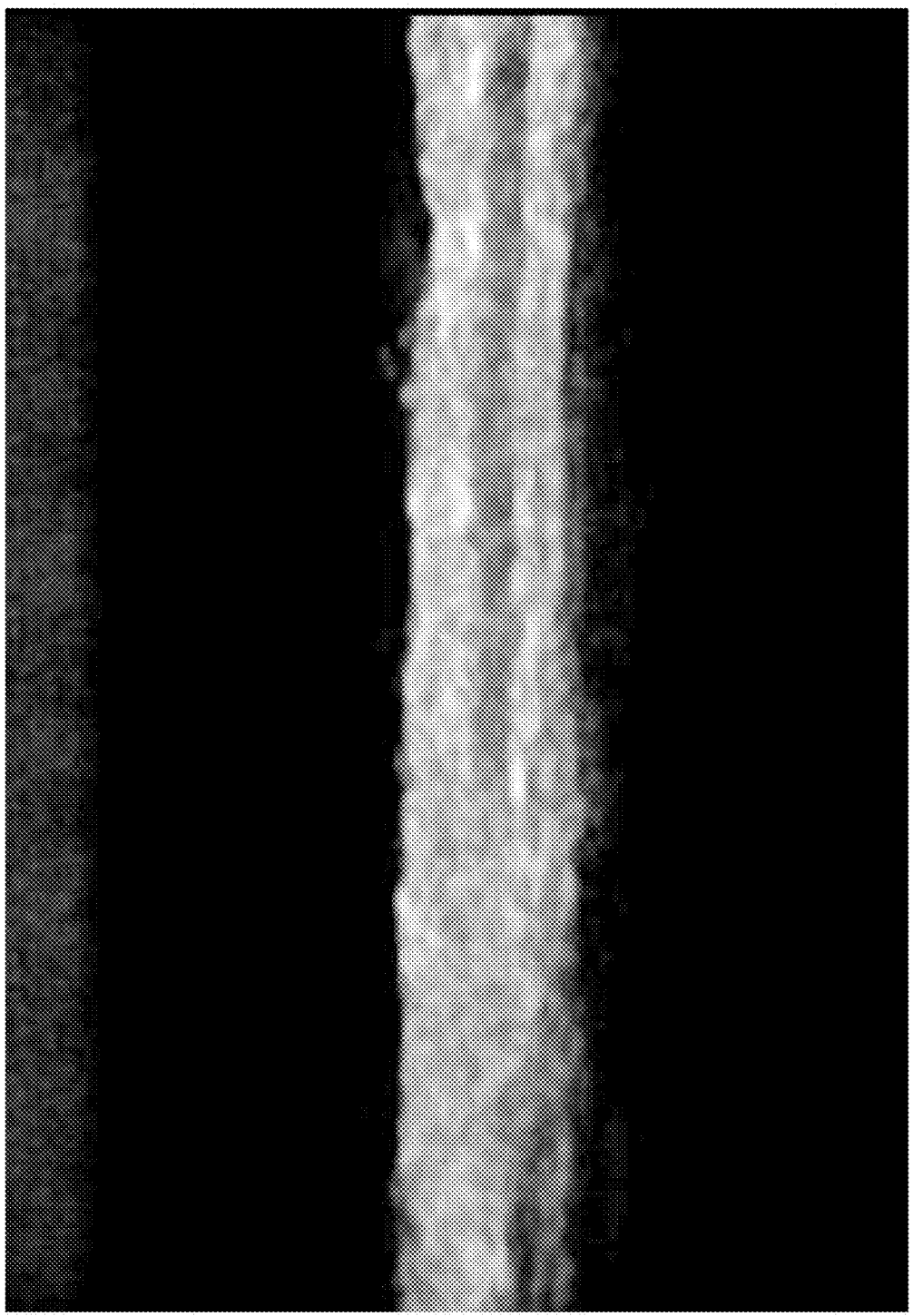
FIG. 11 is a longitudinal ultrasound image of a synthetic vas deferens.
Figure 12:
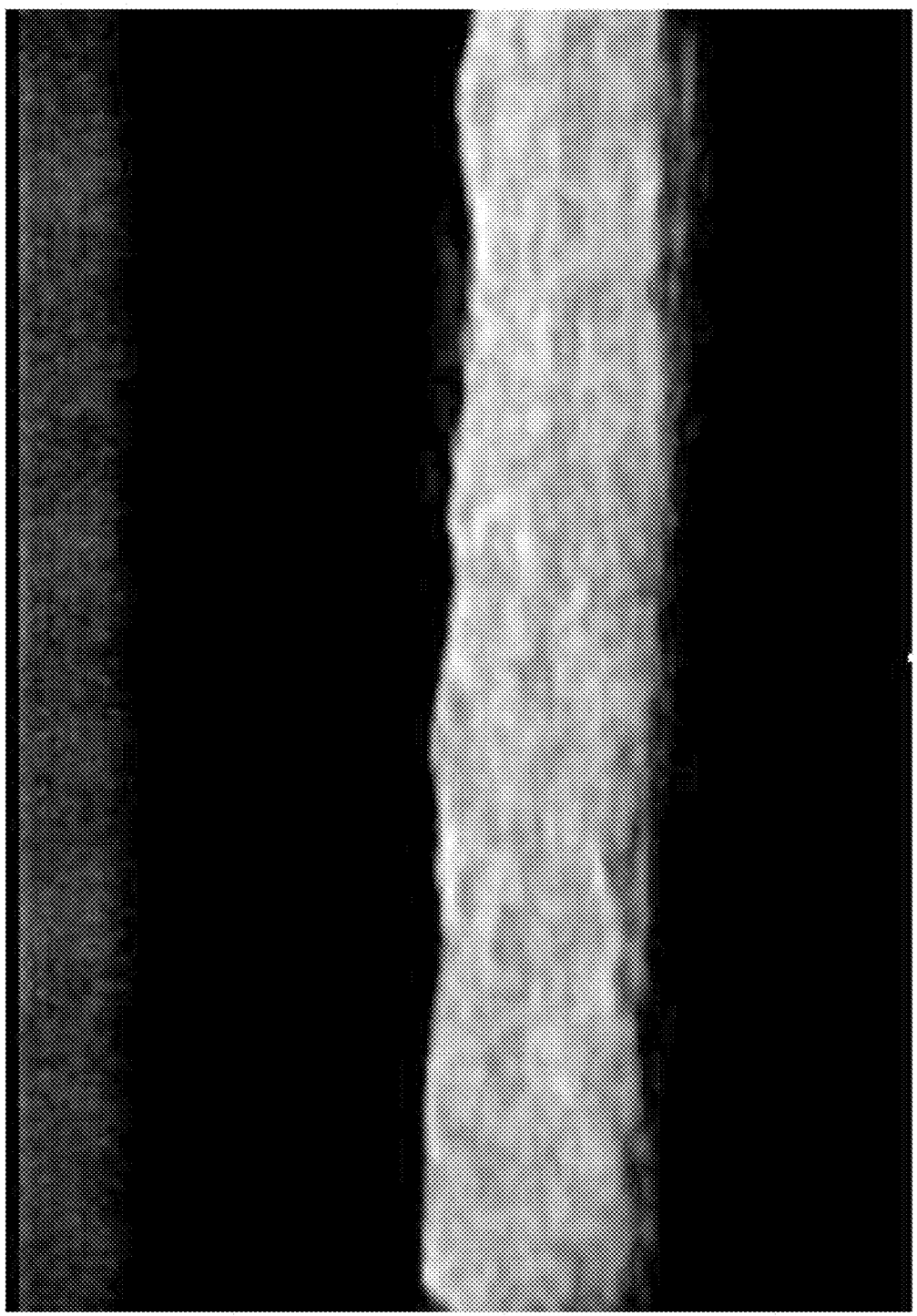
FIG. 12 is a longitudinal ultrasound image of a synthetic vas deferens filled with an EVOH 32-15% polymer gel implant.

The synthetic vas deferens in FIG. 11 has an empty lumen while the synthetic vas deferens in FIG. 12 contains an EVOH 32-15% polymer gel implant. Both synthetic vas were held in place in Knox gelatin, which was formulated according to the manufacturer's recommendations for water:powder ratio. Each vas was imaged in "general" focus and "high" frequency settings using an EZONO 4000 ultrasound. In the longitudinal image of FIG. 11, the hollow lumen of the synthetic vas is clearly visible, while in the longitudinal image of FIG. 12, the lumen of the vas is filled with the polymer gel. Thus, the polymer gel successfully occluded the lumen. This figure also depicts that the EVOH polymer gel is highly echogenic on ultrasound without the need for echogenic particles to be added.

Figure 13A:
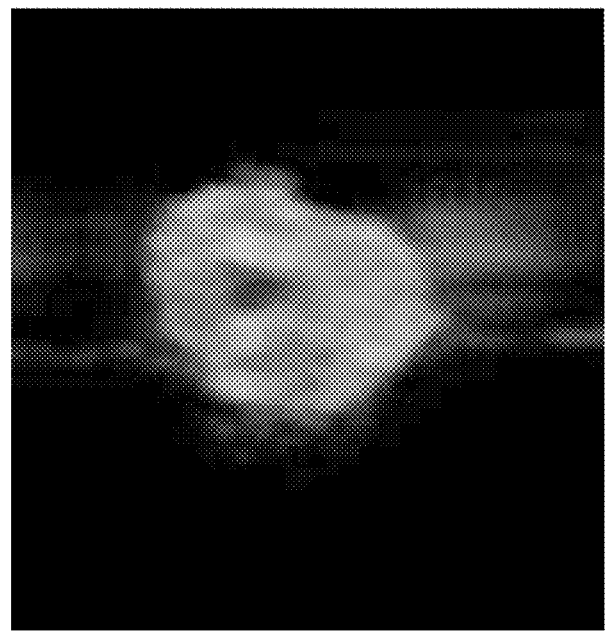
FIG. 13A is an axial ultrasound image of the synthetic vas deferens of FIG. 11.
Figure 13B:
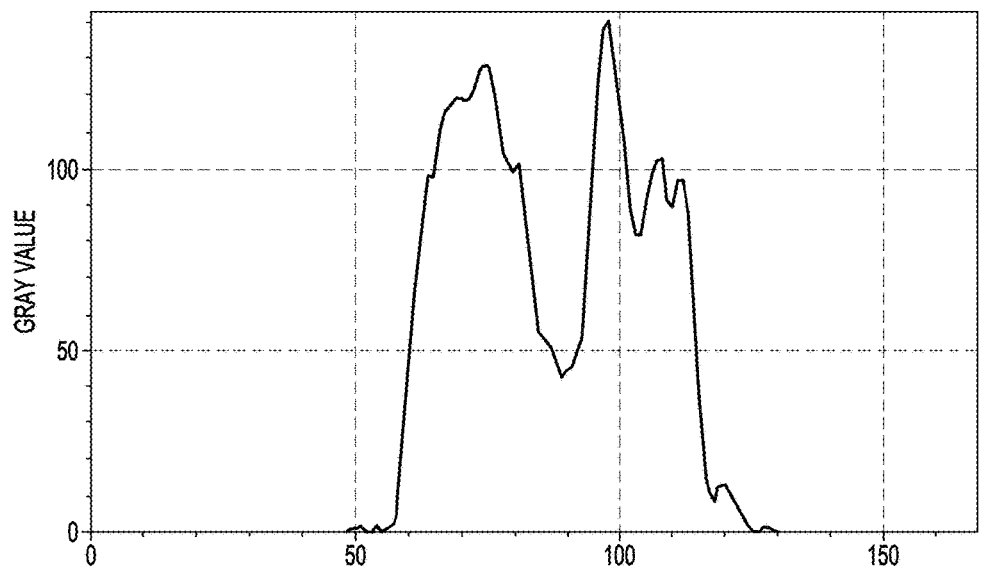
FIG. 13B is a graph of the grayscale values of FIG. 13A.

The synthetic vas was also imaged in axial mode (FIG. 13A). In this mode, the hollow lumen is also visible (shown as the black void). A graph of the grayscale values is shown in FIG. 13B. This graph depicts that at the lumen, the grayscale value drops to below 50.

Figure 14A:
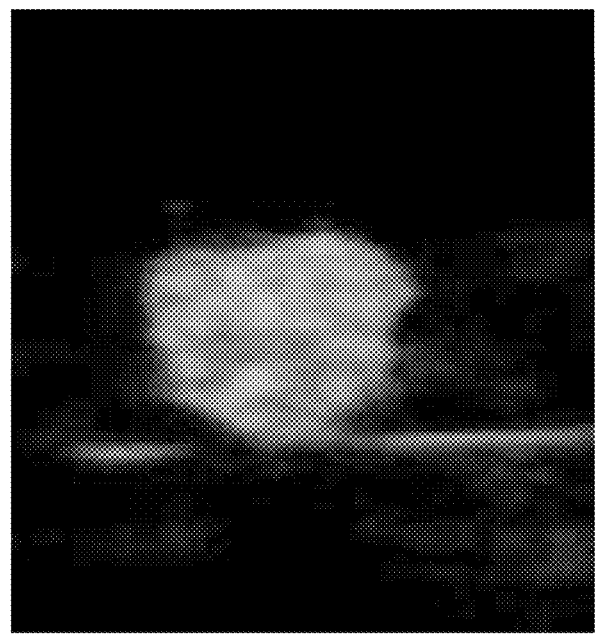
FIG. 14A is an axial ultrasound image of the synthetic vas deferens filled with an EVOH 32-15% polymer gel implant of FIG. 12.
Figure 14B:
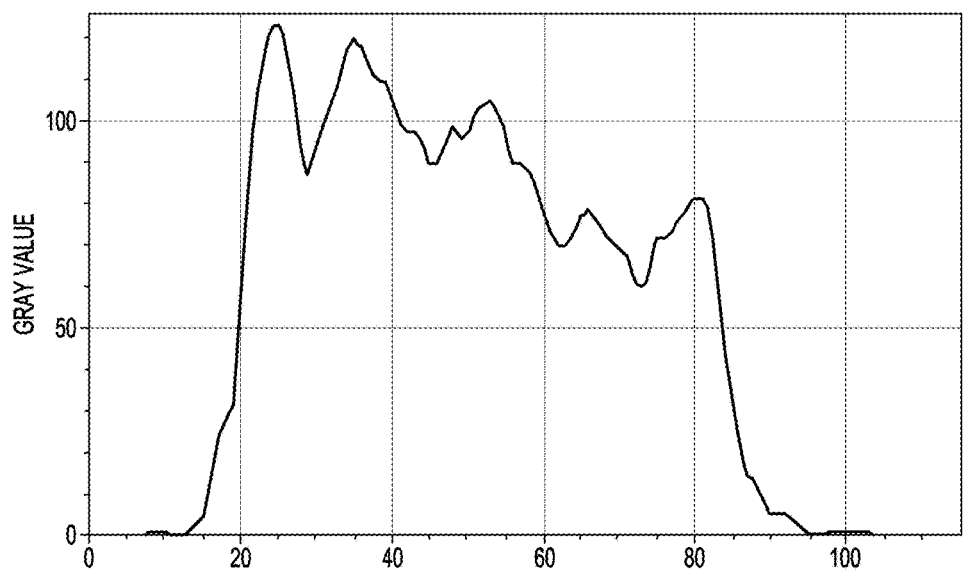
FIG. 14B is a graph of the grayscale values of FIG. 14A.

The synthetic vas containing EVOH 32-15% was also imaged in axial mode (FIG. 14A). In this mode, the hollow lumen is not visible due to the fact that the polymer gel completely occluded the lumen. A graph of the grayscale values is shown in FIG. 14B. This graph depicts that the grayscale value does not drop to below 50, suggesting that the lumen is not void.

Example 3

Testing of a Vas-Occlusive Polymer in Male Rats

This testing relates to the development of a polymer gel for injection into the vas deferens of male rats for use as a contraceptive. The product can be formulated for use in non-hormonal pet and human contraception applications. A polymer is dissolved in sulfoxide (DMSO). Once injected, the DMSO is absorbed by the epithelial lining of the vas deferens, resulting in precipitation of the polymer to form an occlusion. The gel formulation also contains microbubbles, which enhance the contrast of the gel and allow the contraceptive to be visible under ultrasound.

In embodiments, the product is a non-hormonal, ultrasound-imageable contraceptive for male pets and humans. Rats can be used to collect baseline data on the effectiveness of the gel composition as a contraceptive. In such research, in vivo experiments should be used because an in vitro model cannot accurately replace the anatomy and physiology of a vas deferens by transporting and pumping sperm with the same fluid dynamics. A mouse model cannot be used, because the vas deferens is too small to manipulate using the procedure that is proposed for pets and humans. Vasectomy studies are often conducted in rats (see Flickinger C J. Alterations in the fine structure of the rat epididymis after vasectomy. Anat Rec, 1972. 173(3): 377-300; Flickinger C J. Ultrastructure of the rat testis after vasectomy. Anat Rec, 1972. 174(4): 477-493; and Flickinger C J, et al. The influence of vasovasostomy on testicular alterations after vasectomy in lewis rats. Anat Rec, 1987. 217(2): 137-145) due to their larger vas deferens and similar anatomy to larger mammals. A rat model is also the easiest method to study the effects of the gel on sperm concentration, viability, and motility as they pass through. Furthermore, a live animal model must be used to examine the histopathological findings months after the gel has been implanted into the vas deferens.

Rats can be used to confirm the efficacy of an echogenic polymer gel as an ultrasound-imageable, effective contraceptive. The echogenic gel can be formulated as a polymer in DMSO with microbubbles, for example, homogeneously dispersed within. For example, the testing can be organized such that four rats can receive an injection of purely DMSO bilaterally as a negative control and four rats can receive a bilateral vasectomy as a positive control. As in the Koul study, twenty rats can undergo a bilateral injection of a non-echogenic polymer solution in DMSO and twenty rats can undergo a bilateral injection of an echogenic polymer composition (see Koul V., et al. Reversibility with sodium bicarbonate of styrene maleic anhydride, an intravasal injectable contraceptive, in male rats. Contraception, 1998. 58(40): 227-231). The volume injected can be held constant at 60 μL and the concentration can be 0.5 mg of polymer to 1 μL of DMSO. The sperm plug post-mating can be analyzed once a week until 1 month, and then once every 30 days. In both the echogenic and non-echogenic gel receiving groups, eight of the twenty rats can be euthanized after 3 months to perform histopathology of the vas deferens. Eight can undergo reversal of the contraceptive by flushing it out with 10% sodium bicarbonate at pH 8.9. One month after reversal, the rats can be euthanized to examine their histology. Therefore, the total number of male rats necessary for such a study is 4+4+20+20=48 rats. If mating of the male rats with female rats to collect the sperm plug is performed, 12 female rats will be needed as well. The total number of rats is 48+12=60 rats. 15 additional male rats can be used for training purposes. Final count: 75 rats.

One month prior to the procedure, male rats can be allowed to mate with female rats to determine their mating performance. Only male rats with a proven mating performance should be used. Should the female rats become pregnant, the rat pups can be euthanized, and the females can be allowed to recover and used for the subsequent mating studies. For the procedure, the male rat is weighed and anesthetized by intraperitoneal injection with Ketamine/Xylazine (80/10 mg/kg) combined dose (the same anesthesia can be used as maintenance anesthesia during surgery if the procedure lasts more than 30 minutes). Sustained release buprenorphine (0.5 mg/kg) is injected subcutaneously into the scruff of the neck as a primary analgesic. The rats' eyes are treated with petrolatum ophthalmic ointment to prevent dry eyes. Once unconscious, the rats are checked for the absence of a rear foot reflex by pinching the toe, and for the absence of palpebral reflex. Surgeries are performed under sterile conditions, and follow the ACUC Policy on Rodent Survival Surgery. The vasectomy is performed through a vertical midline transabdominal approach. The anesthetized male rat is placed on its back to expose the abdomen. The fur is removed from the ventral area above the penis using electric clippers. The shaved area is sanitized by wiping three alternating times with 10% povidone iodine and 70% ethanol. The sterile drape with a hole exposing the shaved area is placed on the rat. A 10-15 mm longitudinal skin incision is made in the medial line of the abdomen, about 1 cm above the penis. Then, a 5-10 mm longitudinal incision is made in the linea alba. The testicular adipose pad is pulled with dissecting serrated forceps to expose the testis, vas deferens, and epididymis. The vas deferens is located medial to the testis and is a clearly distinguishable free tube, unconnected to the testis, and has a blood vessel running along one side.

In order to perform a vasectomy, the vas deferens loop is held with forceps. At the same time, another pair of forceps is heated with a Bunsen burner until it turns red. Then, the vas is cut and cauterized in two points at once with the hot forceps. The cut should be 5 mm of the vas deferens and leave two clearly separated ends. The testicle, epididymis, and vas deferens are moved back to the abdominal cavity. This procedure is repeated on the contralateral side through the same incision in the abdomen. Rats that undergo a bilateral implantation of the gel can have the same procedure done, as the rats receiving a vasectomy, except instead of cutting/cauterizing the tube, the lumen of the vas is injected with 60 μL of the polymer/microbubble/DMSO composition. The injection is done slowly (0.05 cc/min) using a 23 gauge needle with the flow directed towards the ampulla. The polymer composition does not require sterilization because DMSO is an organic solvent and does not have any bacteria in it. However, sterilization of the composition can be performed according to any available technique, including, for example, by using a 0.22 micron filter that is DMSO compatible, dry heat, autoclave, ethylene oxide, gamma, and/or e-beam, etc. Compression can be maintained with the fingers, just distal to the injection site, to avoid retrograde flow. The polymer precipitates into a gel within a few minutes, causing partial occlusion of the vas. The testicle, epididymis, and vas deferens is moved back into the abdominal cavity. The procedure is repeated on the contralateral side. The muscle will be sutured with one or two horizontal mattress stitches made with 5-0 absorbable sutures (Dexon), and the skin is sutured with a non-absorbable 4-0 monofilament suture (Prolene). Primary post-operative analgesics and a fluid bolus (5-10 mL) are given at this point. The rat is placed on a warm stage and allowed to recover from anesthesia (conscious and maintain sternal recumbency). Ketoprofen (2.5 mg/kg) is given subcutaneously as a secondary analgesic to provide systemic analgesia after the procedure. The rats are monitored every day for 3-4 days post-operation to ensure no surgery related complications such as bleeding, etc. arises. The skin sutures are removed after 10-14 days. Afterward, they are monitored once weekly to ensure the animals are properly recovering and not demonstrating any signs of discomfort or pain. Once fully recovered, the male rat is allowed to mate with a female rat. Mating is confirmed by the presence of sperm plugs (vaginal plugs). It is hypothesized that the contraceptive will prevent conception, but should this happen, the rat pups that are born will be euthanized with carbon dioxide followed by decapitation. The female rats are allowed to recover and be used for subsequent mating. The male also undergo non-invasive ultrasound imaging twice a month for the presence of the polymer gel in the vas deferens. For this, the rat is sedated using an intraperitoneal injection of Ketamine (60 mg/kg) and Xylazine (3.0 mg/kg). The ultrasound probe that can be used is the Acuson 15L8-S at a frequency of 8 MHz. The duration should not be longer than 25 minutes. At 3 months, eight of the rats who received the polymer implant are euthanized by isoflurane overdose and cervical dislocation, and their tissues (distal vas, injection site, proximal vas, cauda epididymis, caput epididymis, and testis) are harvested and examined for the presence of the polymer gel. The inflammatory response of the wall and adventitia of the vas deferens is studied. Eight of the rats undergo reversal of the polymer through a similar procedure as described above, except that a 0.5 mL solution of 10% sodium bicarbonate at pH 8.4 is injected into the vas to flush out the gel. The time to regain fertility can be measured. One month later, the rats who received a reversal are euthanized and histology of the genitourinary tissues is performed.

The rats are observed every day for 3-4 days post operation and weighed once weekly to determine if any problems (redness, swelling, infection) or distress (weight loss >20%, abdominal breathing, lethargy, twitching) appear. If there are any problems, additional analgesics (Buprenorphine, Ketoprofen) are administered for 1-2 days to see if signs are relieved.

Example 4

Method for Forming the Polymer Solutions

In this example, the inventive composition consists of a polymer, ethylene vinyl alcohol (EVOH), dissolved in an organic solvent, such as dimethylsulfoxide (DMSO). EVOH pellets are weighed and suspended in 99.9% DMSO at a desired weight percentage using the following formula:

Wt %=(mass of EVOH)/[(mass of EVOH)+(mass of DMSO)]

The equation can also be rearranged to calculate for the mass of EVOH needed to achieve a certain weight %:

Mass of EVOH=[(wt %)(mass of DMSO)]/(1−wt %)

Once the EVOH pellets are weighed out and suspended in DMSO, the solution is vortexed and left on an orbital shaker for >6 hours (preferably overnight) at >50 degrees C.

The molecular structure of EVOH is shown in FIG. 15B. The structure of styrene maleic acid (SMA) is shown in FIG. 15A for comparison.

It has been shown that the optimal concentrations for the composition are between 6 and 20 wt % of EVOH, with this range seemingly falling within the concentrations ranging from 10-18 wt %. EVOH begins to reach its saturation point at 20 wt %. As the wt % increases, so does the viscosity making injection of the material difficult.

The molecular weights and monomer ratios of EVOH may also be controlled during the polymer synthesis process. For instance, EVOH 27 signifies that the pellet has an ethylene content of 27% and vinyl alcohol content of 73%. For vas-occlusive purposes, the present inventors shown that the optimal ethylene contents are from 27% to 38%, preferably 31-33%. The ethylene content controls the hydrophilicity/hydrophobicity of the polymer: the lower the ethylene content, the higher the vinyl alcohol and therefore, greater hydrophilicity. These factors can impact how the hydrogel forms in water, swells, absorbs water, its viscosity, thermal stability, and durability.

The hydrogen bonds present in the skeletal structure of EVOH polymer, and forming at its crosslink locations, allow for a high degree of mechanical strength. The selection of specific molecular weight (corresponding to the length of the carbon chain backbone) of EVOH allows for the specific observable elastic properties we see in the inventive compositions. Shorter, lower molecular weight polymers have been observed to exhibit fracture and for lack of a better word "brittleness," while the higher molecular weight formulations exhibit higher elastic properties.

Higher molecular weight compounds (corresponding to longer polymer chains) allow for increased polymer flexibility. This is due to the fact that larger molecular weight chains allow for rotation of the chain around the single carbon-carbon bond.

In embodiments, the polymers can have a weight average molecular weight ($M_w$) or number-average molecular weight ($M_n$) ranging from about 1,000 to 1,000,000 as measured by GPC (gel permeation chromatography) with polystyrene equivalents, mass spectrometry, or other appropriate methods. In embodiments, the number-average molecular weight ($M_n$) or the weight average molecular weight ($M_w$) of polymers of the invention can range from about 1,000 to about 1,000,000 Daltons, such as from about 3,000 to about 60,000 Daltons, or from about 20,000 to about 90,000 Daltons, or from about 150,000 to about 900,000 Daltons, or from about 200,000 to about 750,000 Daltons, or from about 250,000 to about 400,000 Daltons, or from about 300,000 to about 800,000 Daltons, and so on. Further, the degree of polymerization of the polymers in embodiments can range from 1 to 10,000, such as from 50 to 500, or from 500 to 5,000, or from 1,000 to 3,000.

The chain length or degree of polymerization (DP) can have an effect on the properties of the polymers. In the context of this specification, the degree of polymerization is the number of repeating units in the polymer molecule. Included are polymers comprising from 2 to about 10,000 repeating units. Preferred are polymers comprising from 5 to 10,000 repeating units, such as from 10 to 8,000, or from 15 to 7,000, or from 20 to 6,000, or from 25 to 4,000, or from 30 to 3,000, or from 50 to 1,000, or from 75 to 500, or from 80 to 650, or from 95 to 1,200, or from 250 to 2,000, or from 350 to 2,700, or from 400 to 2,200, or from 90 to 300, or from 100 to 200, or from 40 to 450, or from 35 to 750, or from 60 to 1,500, or from 70 to 2,500, or from 110 to 3,500, or from 150 to 2,700, or from 2,800 to 5,000, and so on.

Example 5

Manufacture of Microbubbles

Figure 16:
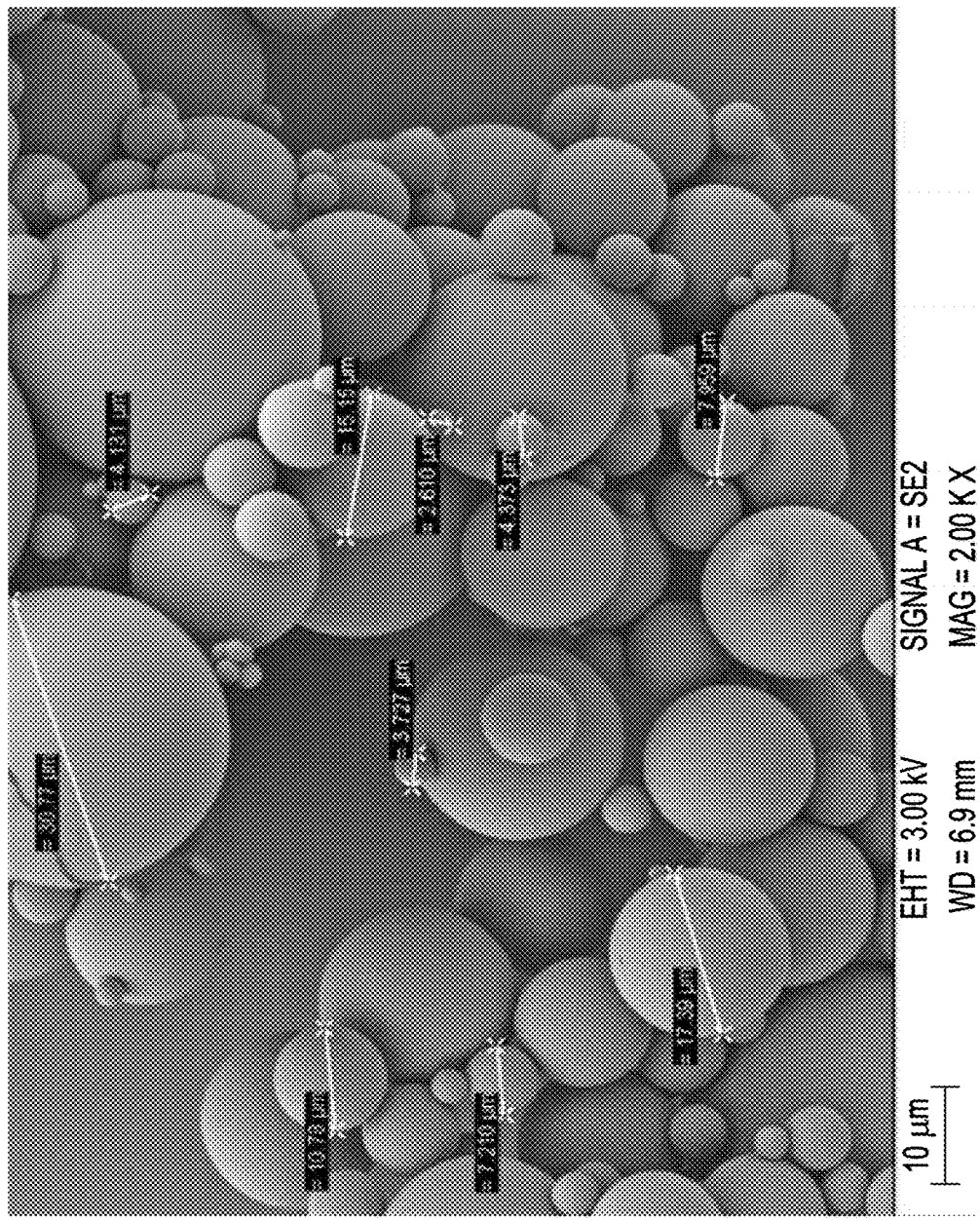
FIG. 16 is a microscopic image of polystyrene microbubbles.

Custom-synthesized polystyrene microbubbles were manufactured. A microscopic image of the microbubbles is shown in FIG. 16.

Example 6

Biocompatibility

Figures 18, 19:
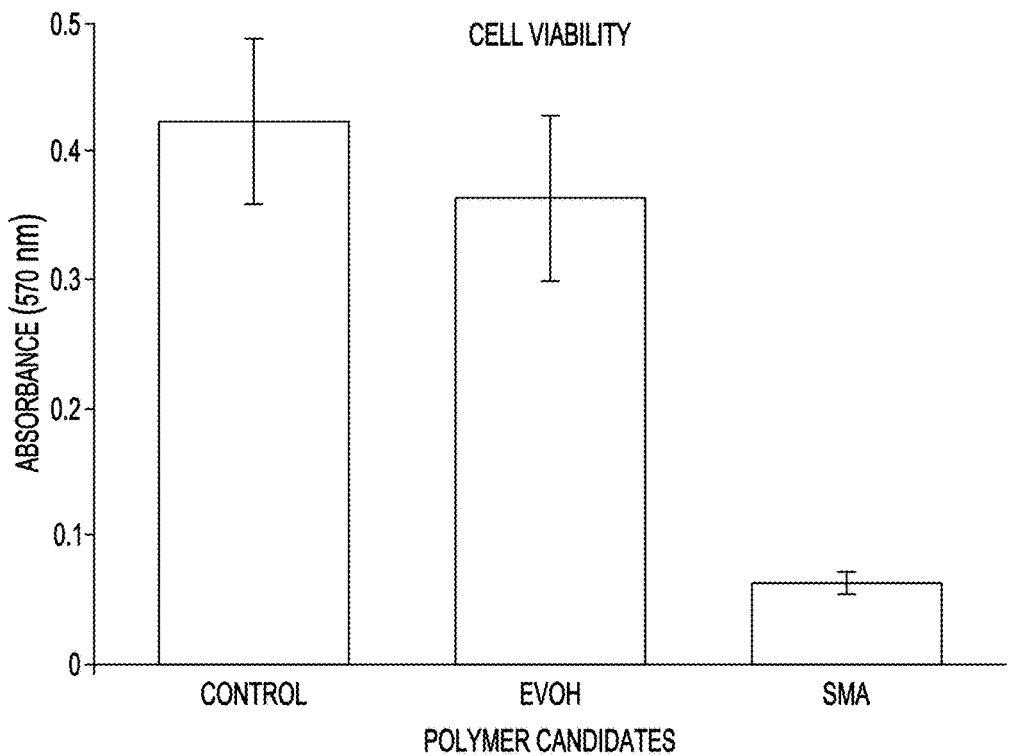
FIG. 18 is a graph showing the results of a cell viability (MTT) assay of EVOH, SMA, and control samples.
FIG. 19 is a table showing the results of statistical analysis (Tukey testing) of the results of FIG. 18.

The cytotoxicity of various polymer formulations including ethylene vinyl alcohol (EVOH), styrene maleic acid (SMA), and control (no polymer gel) was evaluated on mouse Leydig cells (testosterone-producing endocrine cells found in the testes). Leydig cells were chosen as a "worst-case scenario" using a cell line that is unique to the male reproductive tract, and which is sensitive to noxious agents. The assay utilized was an MTT assay, a widely accepted assay for measuring the effect of drugs and devices on cellular cytotoxicity. The polymer gel formulations were allowed to incubate with the cells for 24 hours. After the addition of the MTT reagents and following the standard MTT protocol, the absorbance was read at 570 nm. The results are shown in FIG. 18. Increasing absorbance levels reflect greater mitochondrial activity and therefore, biocompatibility. EVOH polymer formulations cytotoxicity in this assay was compared to that of SMA polymer formulations and the negative control (no gel); the results are shown in FIG. 19. Comparing cytotoxicity of EVOH and the negative control using ANOVA testing and post hoc Tukey testing showed a p-value of 0.076 (greater than an alpha of 0.01), suggesting that there is no significant statistical difference in cytotoxicity between EVOH polymer formulations and the control. Similar comparisons were performed to assess the relative cytotoxicity of SMA to the control; in this case, the resulting p-value was 0.001 (<0.01), suggesting a significant statistical difference between the two exposures. Therefore, it can be concluded that the EVOH polymer formulations tested provide significantly higher biocompatibility compared to SMA polymer formulations. It was also observed that the DMEM media of the cells exposed to SMA polymer gels turned from pink to yellow, suggesting a pH change from neutral to acidic. It is hypothesized that the maleic acid moieties of SMA increase the hydrogen ion concentration, resulting in the pH difference and leading to cell death.

Figures 20, 21:
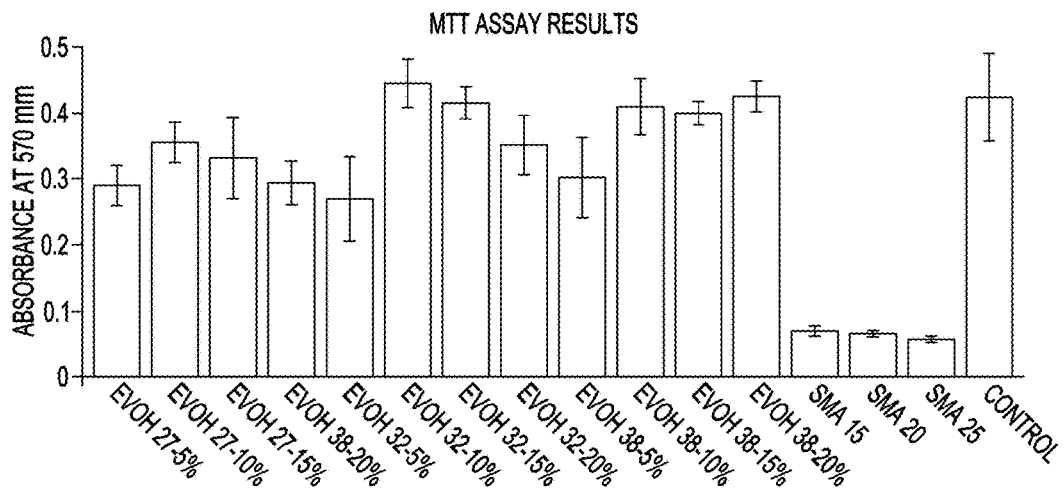
FIG. 20 is graph showing the results of a cell viability (MTT) assay of select polymer candidates.
FIG. 21 is a table showing the results of statistical analysis (Tukey testing) of the results of FIG. 20 comparing EVOH 27, EVOH 32, and EVOH 38.

FIG. 20 shows the results from an MTT assay used to assess the cytotoxicity of a variety of EVOH polymer formulations comprising different monomer ratios of ethylene: vinyl alcohol and weight percentages, as well as several SMA polymer formulations of constant molecular weight (350,000 daltons), but different weight percentages (15%, 20%, and 25%). The VASALGEL formulation is SMA, 350 kD, and 25 wt % in DMSO, which has shown to be very cytotoxic. Similar to the previous experiment, all EVOH formulations were more biocompatible than SMA. This data was analyzed using ANOVA testing and several post-hoc Tukey testings to draw conclusions on the comparisons.

In FIG. 21, post-hoc Tukey testing was used to assess the effect of monomer ratios on cytotoxicity. EVOH 27 polymers are more cytotoxic than EVOH 32, EVOH 38, and the negative control (p values of 0.029, 0.003, and 0.002 respectively). Similarly, it can be concluded that the cytotoxicity of EVOH 32 and EVOH 38 are no different than that of the negative control (p values of 0.248 and 0.499 respectively). Therefore, for vas-occlusion, EVOH 27 should be eliminated as a polymer candidate.

In FIG. 22, post-hoc Tukey testing was used to assess the effect of polymer weight percent on cytotoxicity. Conclusions from these results are that EVOH at 5 wt % has a significantly higher cytotoxicity when compared to the other wt % tested and the negative control (p values of 0.001, 0.001, 0.002, and 0.001 for mass weight percents 10%, 15%, 20%, and the negative control respectively). Therefore, EVOH 5 wt % should be eliminated. This is non-obvious because ONYX and URYX, two medical devices FDA approved for embolization, use 6 wt %. This wt % is not concentrated enough for effective and safe vas-occlusion.

FIG. 23 shows the results of non-GLP Cytotoxicity (MEM Elution) for various polymer solutions. EVOH 32-10%, EVOH 32-15%, and EVOH 28-15% did not exhibit toxicity in the assay.

Several conclusions can be drawn as a whole from the cytotoxicity testing described above. First, SMA based polymers present with significantly higher cytotoxic effects when compared to EVOH polymers. Second, low weight percent EVOH polymers are more cytotoxic than high wt % formulations. This is likely due to the lower degree of polymerization that occurs with these samples, and thus the presence of more active monomer units that can have negative cellular effects. Finally, EVOH 27 formulations of all weight percentages demonstrate increased cytotoxicity when compared to the control, suggesting that such formulations should be excluded as viable products.

Example 7

Rodent Animal Model

Sexually mature, 11-16 week old rats received either vasectomy or VASINTOMY™ via surgical approach transabdominally. The technique involved injection of 60 µL of SMA or EVOH gel approximately 4 cm caudal to the prostate with injection proceeding antegrade. The animals recovered for a period of 3 days or 14 days. At the end of the time period, the rats were humanely euthanized and their reproductive tract was studied by macroscopic and microscopic pathologic examinations.

Figure 24:
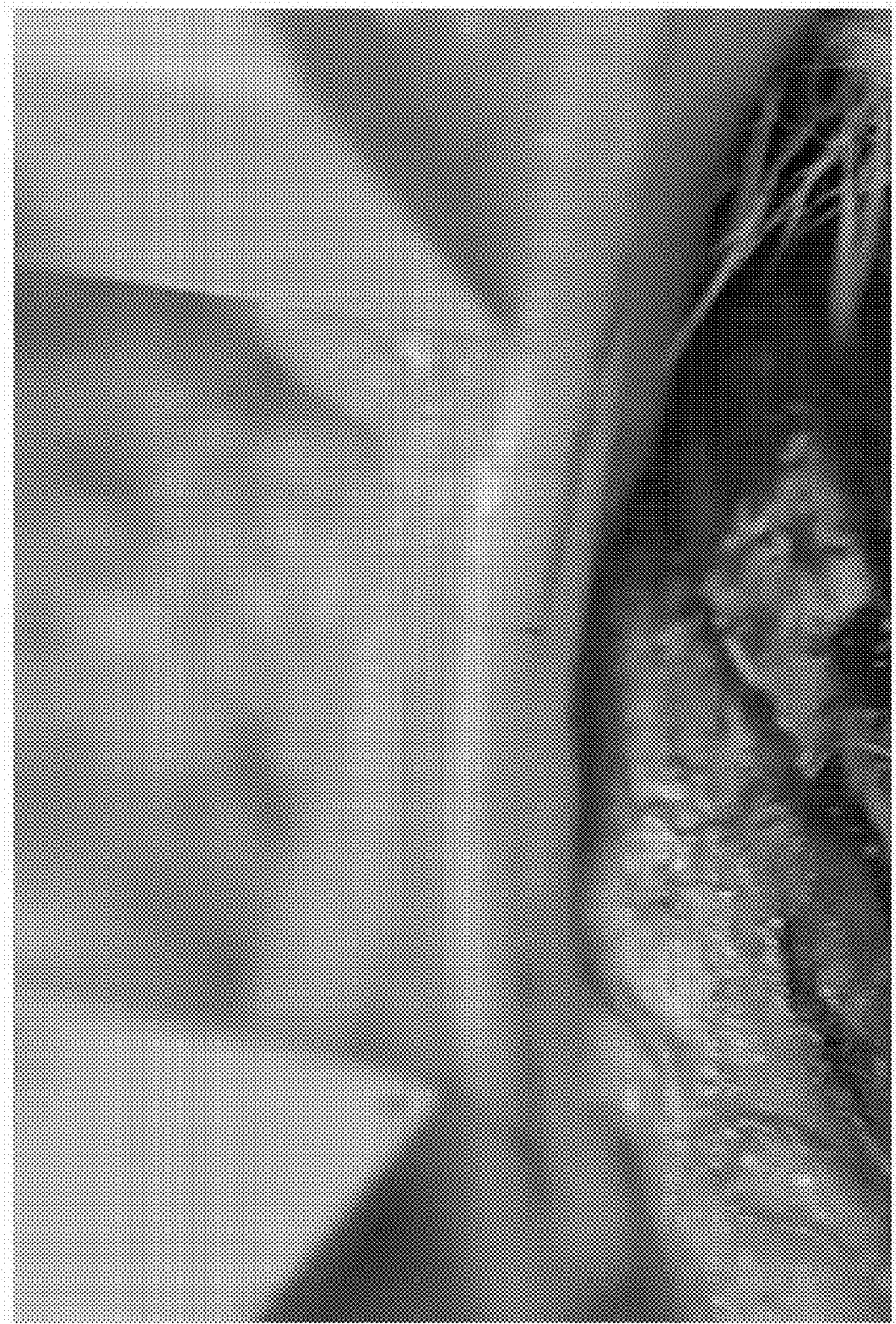
FIG. 24 is a photograph showing results of injection of a polymer in the vas deferens in a rodent model.
Figure 25A:
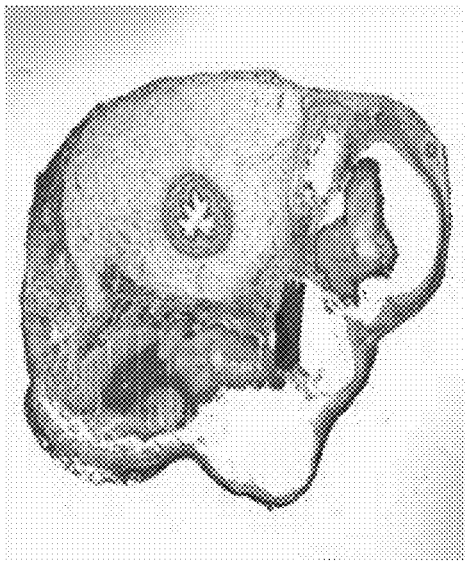
FIGS. 25A-25D are histopathology images of the vas deferens of 12 week old, Sprague-Dawley male rats which received injections of a SMA polymer solution.
Figure 25B:
Figure 25C:
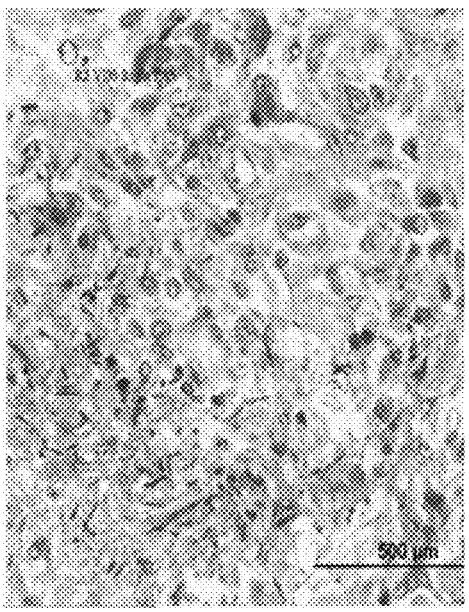
Figure 25D:
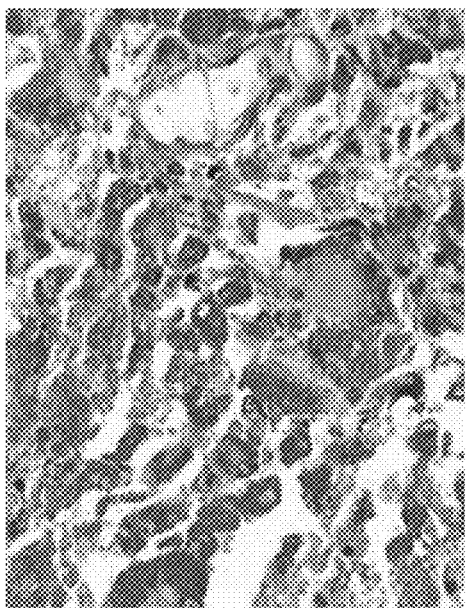

FIG. 24 below shows the results of a VASINTOMY™ in an animal model with a detailed view of the injected EVOH 32-15%. Note the yellowish-white, opaque material visualized through the outer muscular tunics of the vas deferens.

In preliminary rodent trials, the present inventors' studies showed that SMA incited an intense inflammatory reaction within the muscular wall or spermatic cord connective tissues. FIGS. 25A-25D show histopathology images of the vas deferens of 12 week old, Sprague-Dawley male rats received bilateral vasectomy or VASINTOMY™ using SMA. Vas deferens were examined via histopathology on post-surgical day 14 after implantation. As shown in the figures, sections of vas deferens which contained surgically implanted SMA gels were characterized by presence of numerous inflammatory cells. The cells were associated with abundant intra- and extra-cellular amorphous, lightly basophilic material and/or spermatozoa. The material was noted to be PAS positive on special stains, and was consistent with SMA hydrogel. Many of these collections and nodules were present in the wall of the vas deferens or adjacent fat or fascia. These findings indicate that further study is needed to characterize SMA in mammalian animal model systems, and that EVOH may provide a better composition.

Studies by the inventors have demonstrated that EVOH gel injection in rodent animal models induces a dense plug that has the potential to completely occlude the vas deferens lumen resulting in azoospermia. In one preliminary rodent trial, 16-week old, Sprague-Dawley male rats received bilateral vasectomy or VASINTOMY™ using EVOH 32-15%. Vas deferens were examined via histopathology on post-surgical day 3 after implantation. EVOH was associated with inflammation in some animals, however, this reaction was different from that of SMA, in that there was rapid connective tissue proliferation associated with the vasal epithelial and lamina proprial layers. The changes, including fibrosis and fibroplasia were similar to microscopic changes evoked intravascularly with FDA-approved use of the composition in arteries. Further characterization of the in vivo safety and efficacy are forthcoming.

Figure 26A:
FIGS. 26A-26C are histology images of the vas deferens which represent the change in the luminal diameter and content of the vas deferens after injection of an EVOH polymer solution.
Figure 26B:
Figure 26C:
Figure 27B:
FIGS. 27A-27D are histology images which show the resting diameter of the epithelial lamina propria.
Figure 27D:
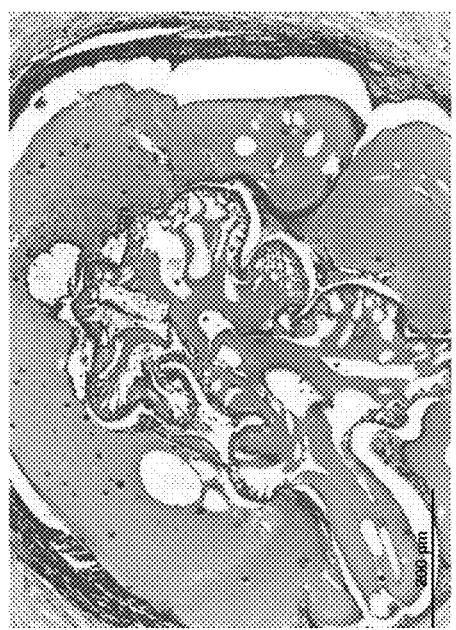
Figure 27A:
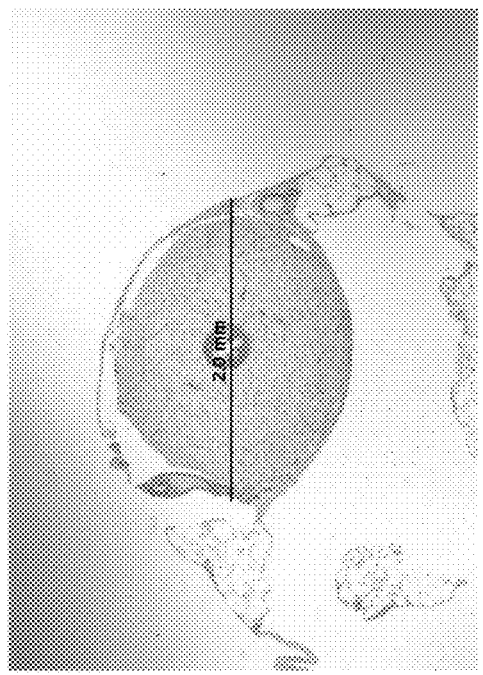
Figure 27C:
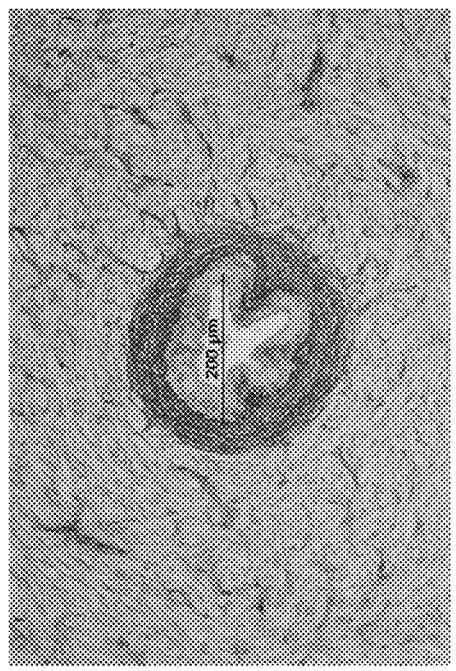

The following figures show histology images which represent the change in the luminal diameter and content of the vas deferens of a 16 week old rodent subjects on post-surgical day 3. FIG. 26A shows an age-matched control vas deferens (day 0). Note the small diameter, of the lumen relative to the thick muscular wall of the tunica muscularis. FIG. 26B shows the vas deferens (HE staining) of a treated subject. EVOH 32-15% in lumen of vas deferens is associated with dilation of lumen and muscular tunics, with retention of overall diameter of the vas deferens when compared with control. FIG. 26C (PAS staining) shows that the EVOH 32-15% serial section of FIG. 26B exhibits intense affinity of the hydrogel (polymer implant) for PAS stain.

FIGS. 27A-27D are histology images which show that the resting diameter of the epithelial lamina propria is approximately 200 μm. The vas luminal diameter with polymer implant increased to nearly 1.0 mm in this subject. Dilation of the lumen is characterized by attenuation and compression of the normal mucosal folds with compression of the smooth muscle tunic cells, while preserving overall total vas deferens diameter.

Example 8

Injection Volume for Humans Based on Vas Diameter

FIG. 28 is a table showing the relationship between inner diameter (dilated) and injection volume and for various targeted occlusion sizes for human vas-occlusive contraception. The source of the table is a study by Zhao Shengcai.

Example 9

Porosity

Porosity is an essential parameter to predict the efficacy of the inventive compositions. The polymer gel must have porosity tailored for preventing the passage of sperm cells, while allowing for appropriate levels of fluid infiltration. Sperm cells present with a wedge-shaped head with dimensions of 3 μm×5 μm. Thus, the vas-occlusive contraceptive should have an average pore size below 3 microns.

Figure 30A:
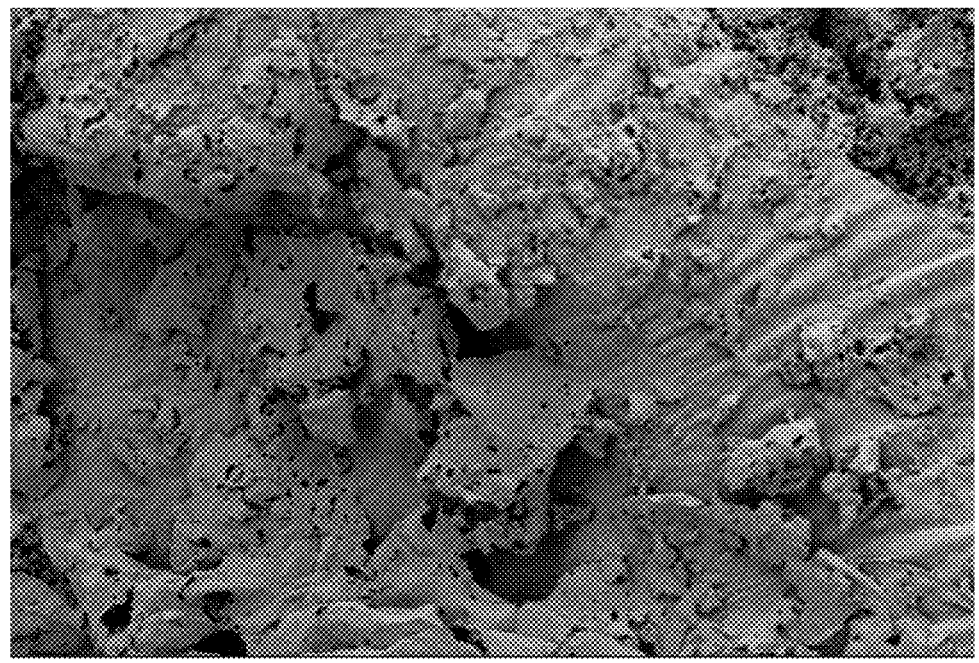
FIG. 30A shows a scanning electron microscopy image for the EVOH 32-10% of FIG. 29.
Figure 30B:
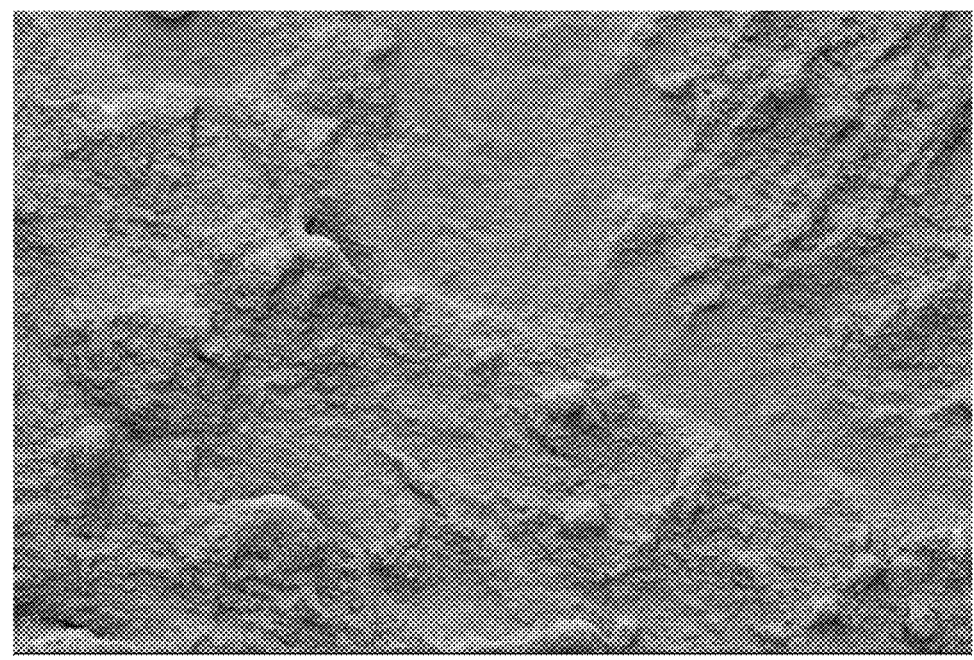
FIG. 30B shows a scanning electron microscopy image for the EVOH 32-15% of FIG. 29
Figure 30C:
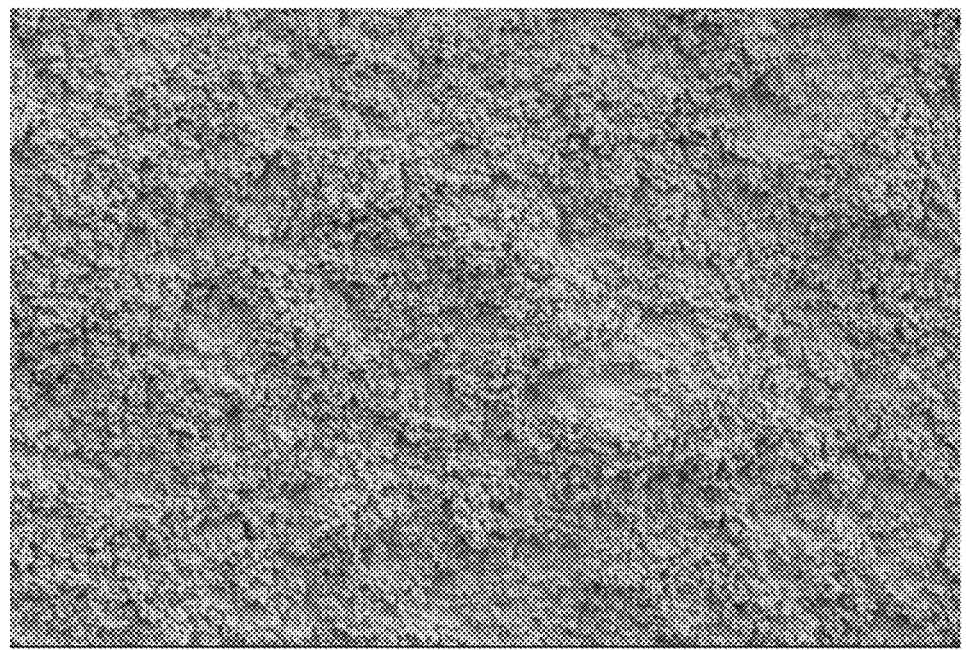
FIG. 30C shows a scanning electron microscopy image for the EVOH 32-20% of FIG. 29

Porosity of the gels was assessed several ways. Scanning electron microscopy (SEM) allowed for visualization of the pores on a 10 μm scale. Pore size was assessed by direct software-assisted measurement. However, this method was not optimal for determining the average of all the pores on the polymer's surface. Brunauer-Emmett-Teller (BET) analysis is a superior quantitative method which can measure the number of gas molecules that adhere to a surface at a given pressure differential. This number can be related to the surface area of the sample in question via BET analysis. BET surface area analysis and subsequent Barrett-Joyner-Halenda (BJH) pore size and volume analysis allow for the comparable quantification of sample pore size and surface area. The BET results for select polymer candidates are shown in the table of FIG. 29, while representative SEM images are shown in FIGS. 30A-C. The SEM results show that EVOH 32-10% (FIG. 30A) did have small pores present, while EVOH-32 15% (FIG. 30B) and 20% (FIG. 30C) did not. The 15% had a very flat surface while 20% exhibited classic spinoidal decomposition (meaning that there was a phase separation of the polymer from solvent). Basically, 20% was the saturation point for EVOH.

Pore size was determined using the following equation:

$$\text{Average Pore Diameter} = (4 * \text{Av.Pore Volume}) / \text{Specific Area}$$

BET analysis suggests that EVOH polymers, in general, has a much lower average pore diameter than SMA polymers. This supports the fact that EVOH films are used for wrapping and preserving food, to prevent gases from traveling through. Furthermore, as the weight % increased, the pores on the EVOH gels became smaller. At EVOH 32-15 wt % and 20%, the average pore size is below the size of atoms (0.5 nm). Initial experiments suggest that at high wt %, EVOH is essentially non-porous.

Pore size is an essential modifiable parameter relating to the efficacy of the inventive compositions as a vas-occluding technology. The porosity of male-contraceptive compositions must be tailored to appropriately allow flow through of fluid, while preventing such negative effects as sperm granuloma, vas deferens rupture, and subsequent epididymitis.

Example 10

Hardness/Elasticity

In a study by Bank et al., (see Bank et al., "Contribution of Collagen, Elastin, and Smooth Muscle to In Vivo Human Brachial Artery Wall Stress and Elastic Modulus", Circulation. 1996; 94:3263-3270), it was determined that the greatest active stress generated by the smooth muscle in the brachial artery was $1.24 \times 10^{\wedge}6$ dynes/cm$^2$. If it is assumed that 70% of the brachial artery cross-sectional area is smooth muscle, then the active stress generated by the smooth muscle is $1.77 \times^{\wedge}6$ dynes/cm$^2$ (or 177 kPa).

Elastic modulus is representative of a material's ability to deform under stress without undergoing permanent plastic deformation. The present inventors have predicted the stress that the vas deferens will be generate during ejaculation based on the thickness of smooth muscle in the organ and the known force-production properties of smooth muscle during arterial contraction (see reference above). Therefore, using this prediction of the stress that the inventive compositions will be under, we are able to determine a design parameter defining the elastic properties that our compositions must have.

Figures 31, 32:
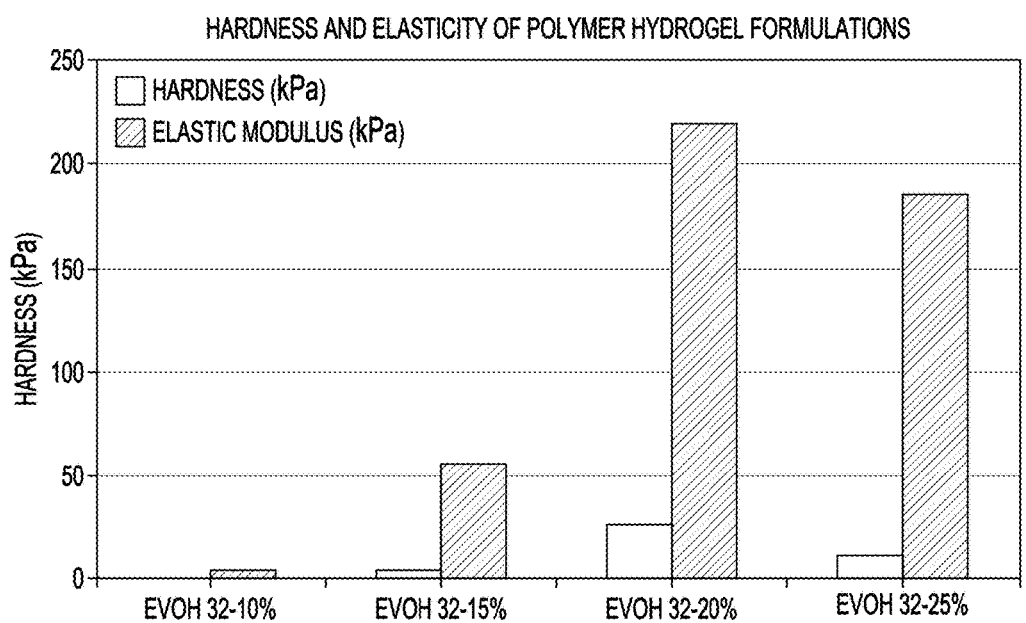
FIG. 31 is a table showing the hardness and elastic modulus of select polymer candidates.
FIG. 32 is a graph of the results of FIG. 31.

Assuming the smooth muscle in the vas has similar elastic properties as the smooth muscle in the brachial artery (124 kPa) and 90-93% of the cross-sectional area of the vas is made of smooth muscle (this was calculated using measurements of inner and outer vas diameters), then the maximum stress that the smooth muscle in the vas can generate is 1.37×10^6 dynes/cm^2 or 137 kPa. As per the table in FIG. 31 and the graph in FIG. 32, only EVOH 32-20% and SMA-25% would be able to withstand the stress of the vas since their elastic modulus is greater than 137 kPa.

Example 11

Spermicidal Effects of the Compositions

Figure 33:
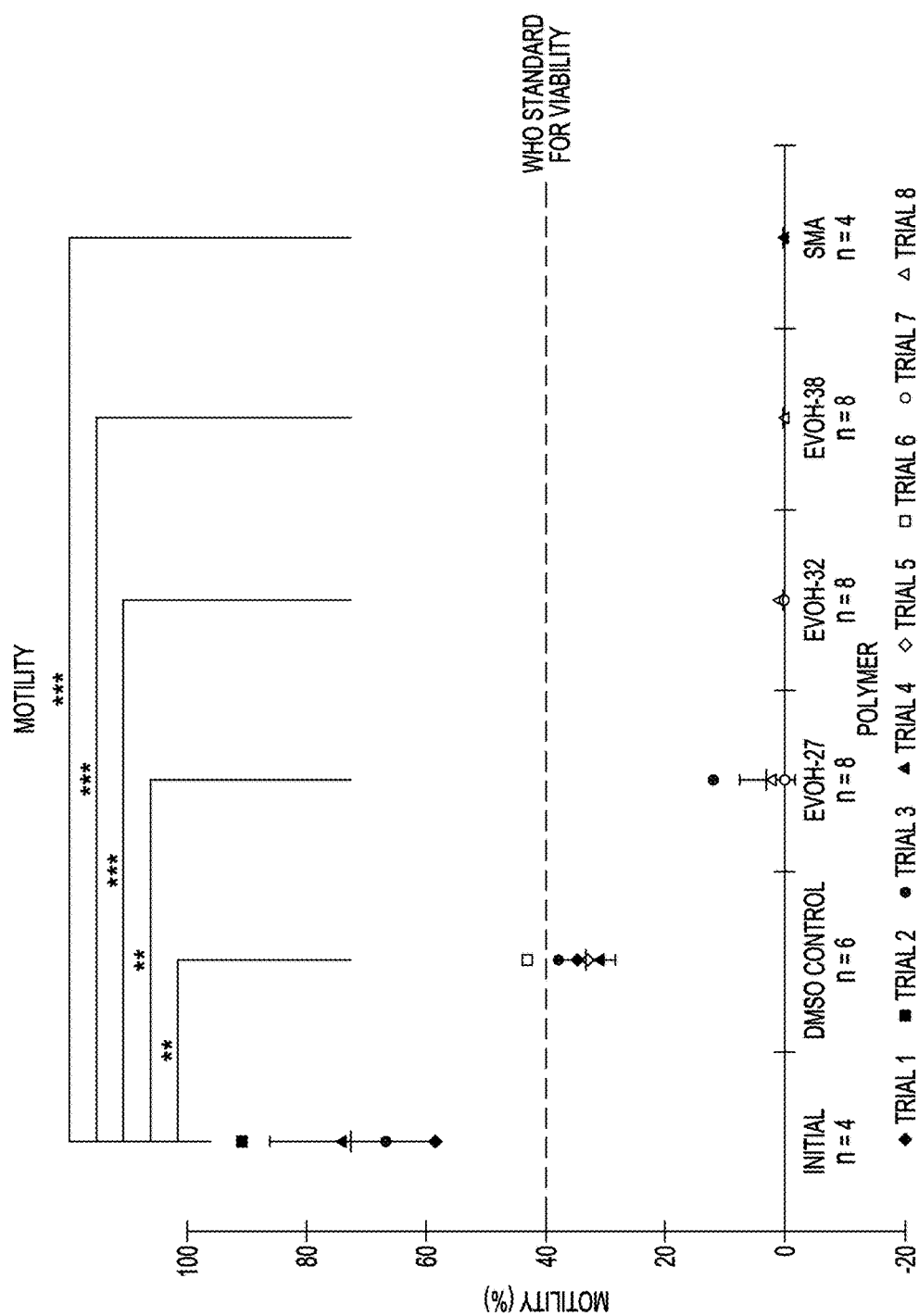
FIG. 33 is a graph showing the results of a sperm motility assay of select polymer candidates.

In addition to blocking sperm, it was also discovered that different polymer formulations may have spermicidal characteristics. This effect, most likely a secondary "mode of action", may help increase the efficacy of the inventive compositions in vivo. An in vitro set-up was designed where the gels were precipitated on top of a mesh in cell strainers and human sperm samples were added to the top of the gels. After 30 minutes of exposure, sperm cells were observed under a microscope and scored for motility. The results are shown in FIG. 33. Initial ANOVA analysis of the results showed a significant difference between treatment groups, therefore post-hoc Tukey HSD was applied in order to determine whether EVOH and/or SMA polymers decreased sperm motility (FIG. 34A). Tukey testing (FIG. 34B) showed that sperm interaction with EVOH and SMA polymers significantly decreased motility below WHO standards when compared with DMSO negative control. The decrease in motility in the DMSO (negative control) samples were most likely due to natural physiological changes in motility over time and were likely not caused by DMSO itself. Furthermore, EVOH 32, EVOH 38, and SMA did a better job of decreasing sperm motility than EVOH 32.

Figure 35:
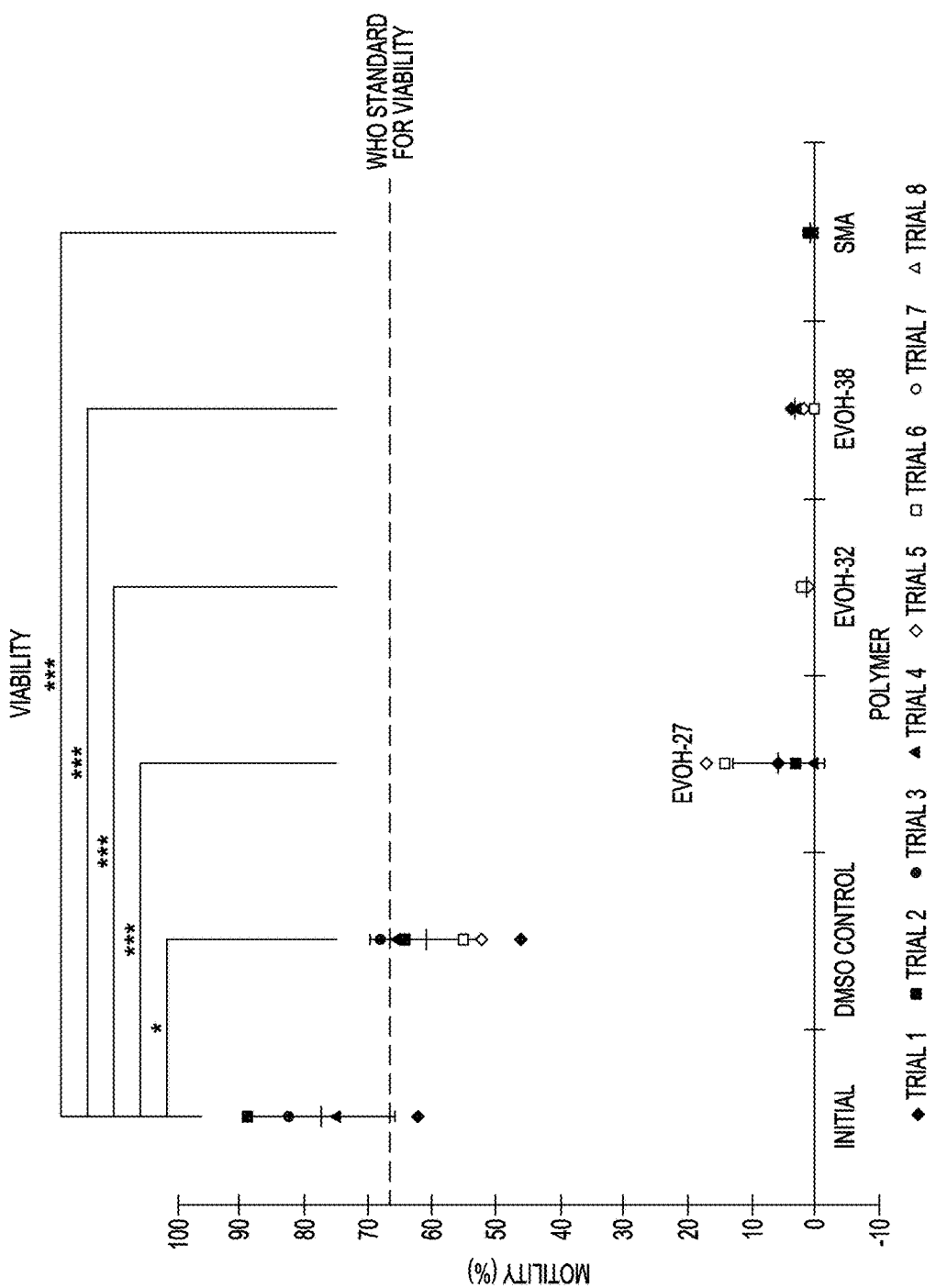
FIG. 35 is a graph showing the results of a sperm viability assay of select polymer candidates.

Spermicidal characteristics of the EVOH polymer implant was tested by using a viability assay in which human sperm cells were incubated with gels formed on cell strainers. After 30 minutes of exposure, sperm cells were stained with Trypan Blue dye and observed under a microscope. The percentage of viable sperm were recorded for each sample. The results are shown in FIG. 35. Initial ANOVA analysis of the results showed a significant difference between treatment groups, therefore post-hoc Tukey HSD was applied in order to determine whether EVOH and SMA polymers decreased sperm motility (FIG. 36A). Tukey testing showed that incubation with EVOH polymers significantly decreased motility when compared with DMSO negative control (FIG. 36B). The significant decrease in viability due to incubation with DMSO was most likely due to natural physiological changes in viability and not likely caused by DMSO itself.

Example 12

Viscosity and Rheological Properties of the Polymer Solutions

Figure 37:
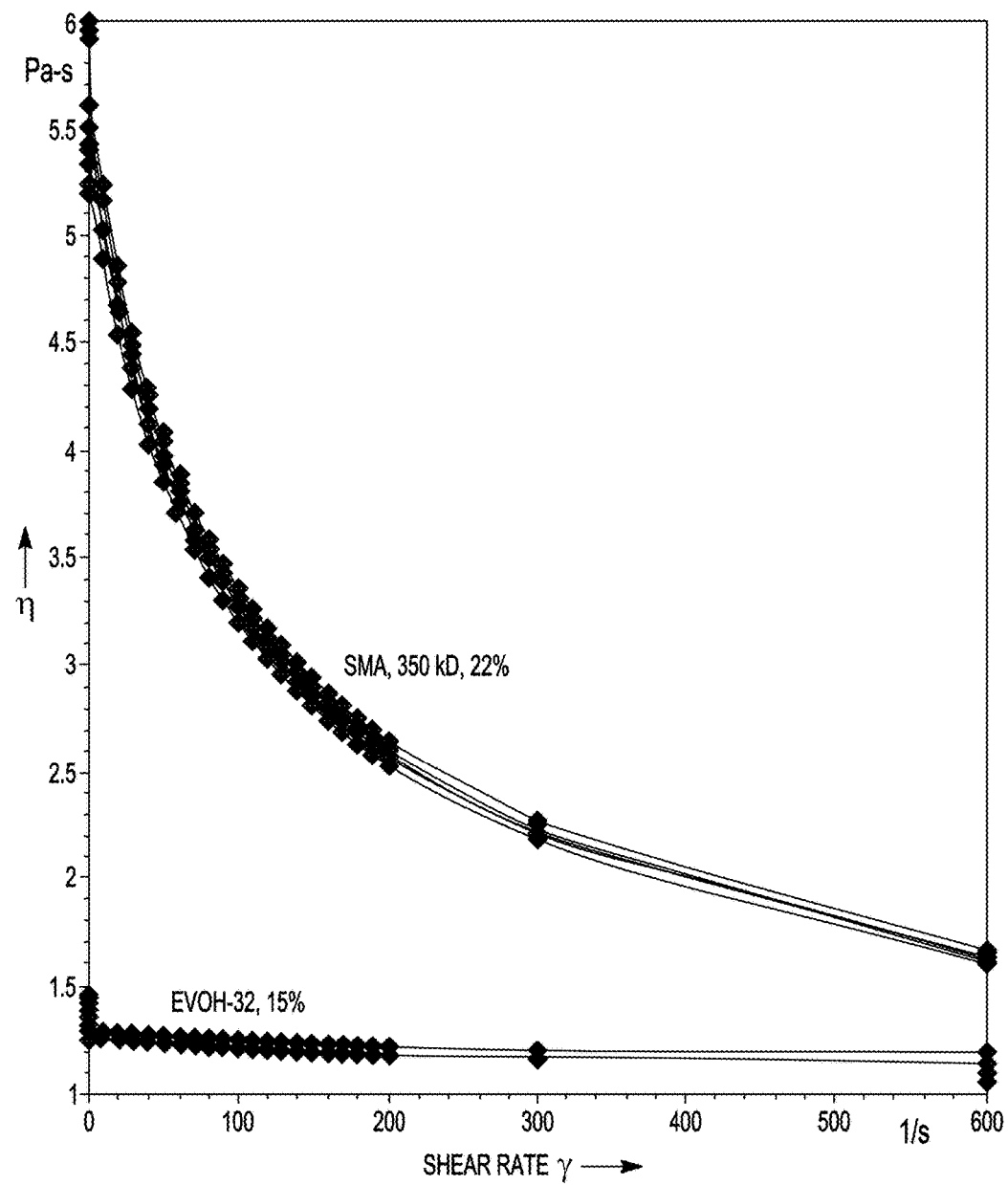
FIG. 37 is a graph showing viscosity as a function of shear rate for select polymer candidates.

A controlled shear rate test was performed with an Anton Parr rheometer (Physica MCR 301) to measure the viscosities of SMA (350 kD) 22 wt % and EVOH 32-15%. The viscosity as a function of shear rate graph shown in FIG. 37 shows that SMA has an extremely pronounced shear-thinning behavior, meaning that its viscosity decreases as the shear rate increases. This behavior stems from the increase in the disentanglement of polymer molecules at higher shear rates. However, the graph shows that the viscosity for EVOH is independent of shear rates. This Newtonian fluid behavior is particularly significant in that it is the simplest mathematical model of fluids that account for viscosity, and the application of Hagen-Poiseuille relation that relates the viscosity measurements to the formulation of injection mechanisms is much more simplified compared to one for the non-Newtonian shear-thinning behavior exhibited by SMA. The graph also illustrates that the viscosity of SMA at 22 wt % is about 4 times higher than that of EVOH 15 wt %. The relatively small value of viscosity for EVOH is also allows for more efficient injection mechanism, as the smaller needle gauge (with larger bore) will be required to extrude the polymer solution for higher viscosity solutions.

Figure 38:
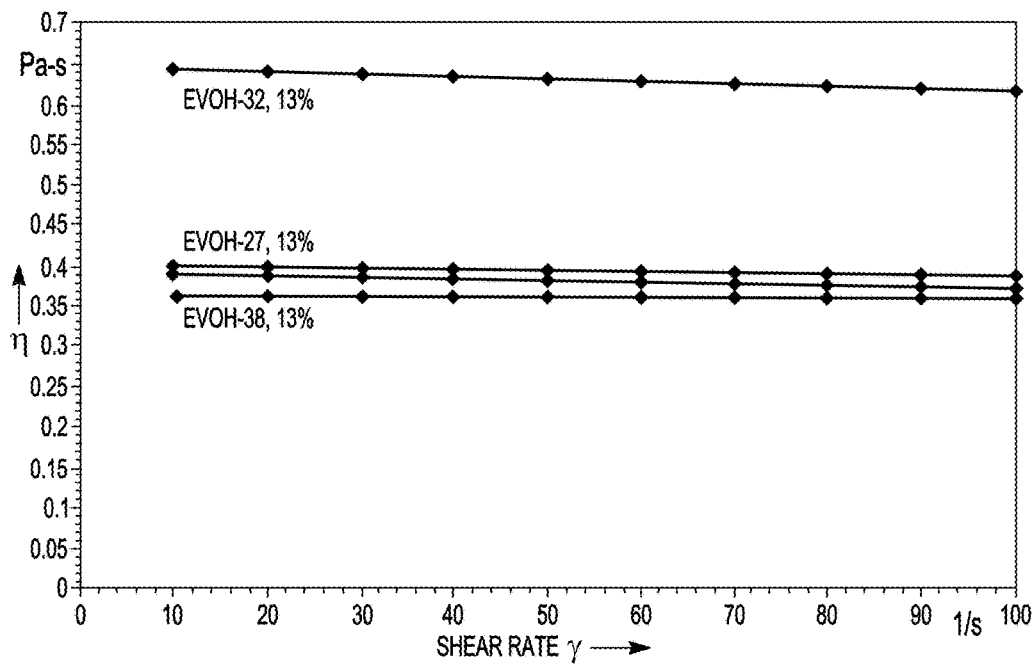
FIG. 38 is a graph showing the effect of ethylene mol % on the viscosity of EVOH as a function of shear rate using the controlled shear rate test.

The effect of ethylene mol % on the viscosity of EVOH was tested with a controlled shear rate test under isothermal condition (T=37 degrees Celsius). The graph in FIG. 38 shows the lower shear rate range of the data for EVOH. The results show that an increase in the ethylene mol % does not necessarily correspond to an increase in the viscosity. It is generally established that higher molecular weight of polymers results in increased strength, stiffness, and therefore viscosity. Based on this general premise and the viscosity data, it is hypothesized that the EVOH 38 has a lower molecular weight than EVOH 27. To prove this hypothesis, GPC (Gel Permeation Chromatography) or DSC (Differential Scanning calorimetry) will need to be conducted to accurately determine the molecular weight distribution.

Figure 39:
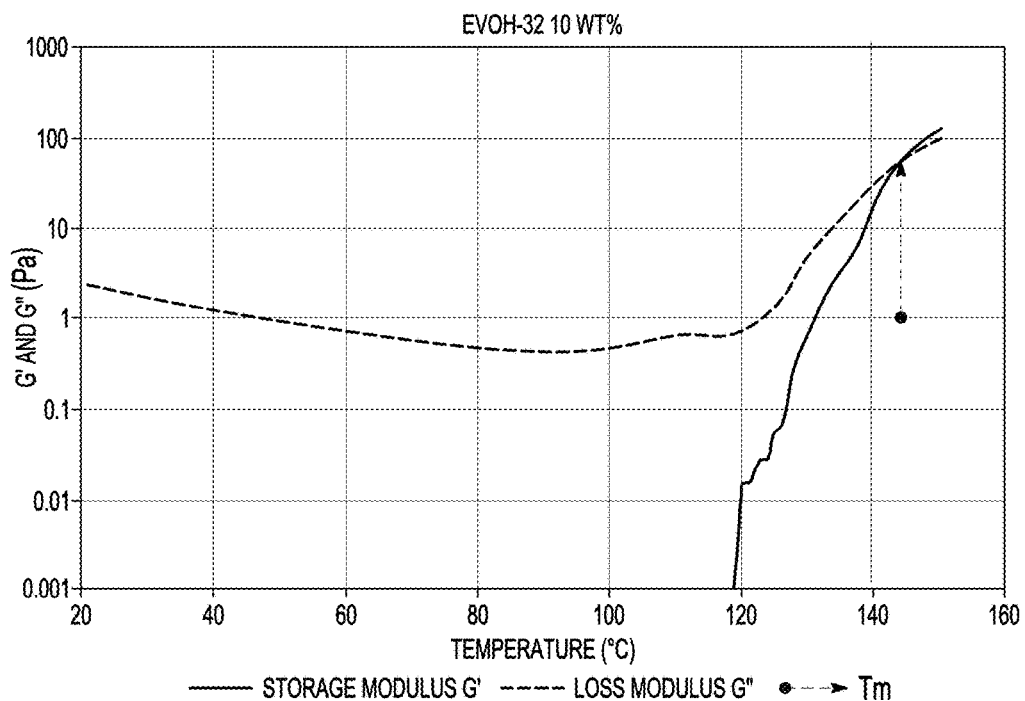
FIGS. 39-41 are graphs showing melting temperatures and glass transition temperatures for EVOH 32-10%, EVOH 32-15%, and EVOH 38-15%, respectively.

To determine the gel time in form of the sol/gel transition point, an oscillatory test in the linear viscoelastic (LVE) deformation range was performed for EVOH 32 at different wt %. The results are shown in FIG. 39. The melting point occurs at the crossover point of storage modulus G' and loss modulus G". For 10 wt %, the melting point occurred at approximately 144 degrees Celsius. The glass transition point occurs at the first inflection point of G', which was absent in this run. More trials are needed to confirm the accuracy of the data.

Figure 40:
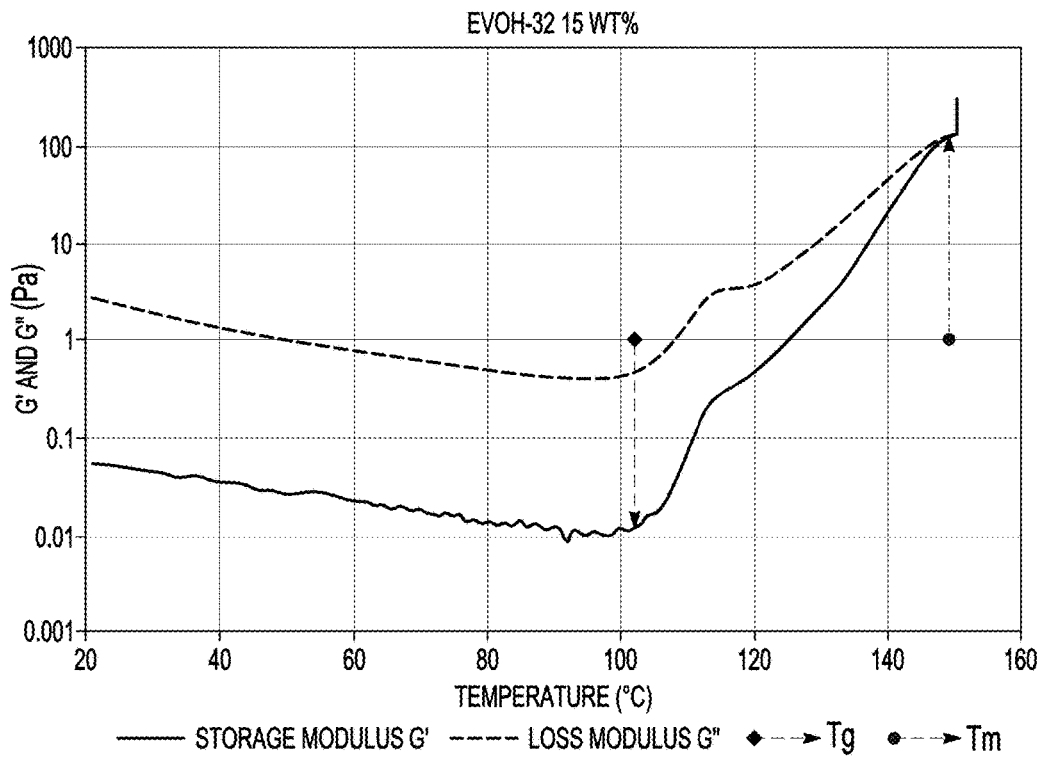

For EVOH 32-15% (FIG. 40), the melting point occurred at 149 degrees Celsius, which is 5 degrees higher than that for 10 wt %. The glass transition point occurred at 102 degrees Celsius, indicating that the reversible transition from a hard, brittle material to a soft, rubbery material occurs at that temperature.

Figure 41:
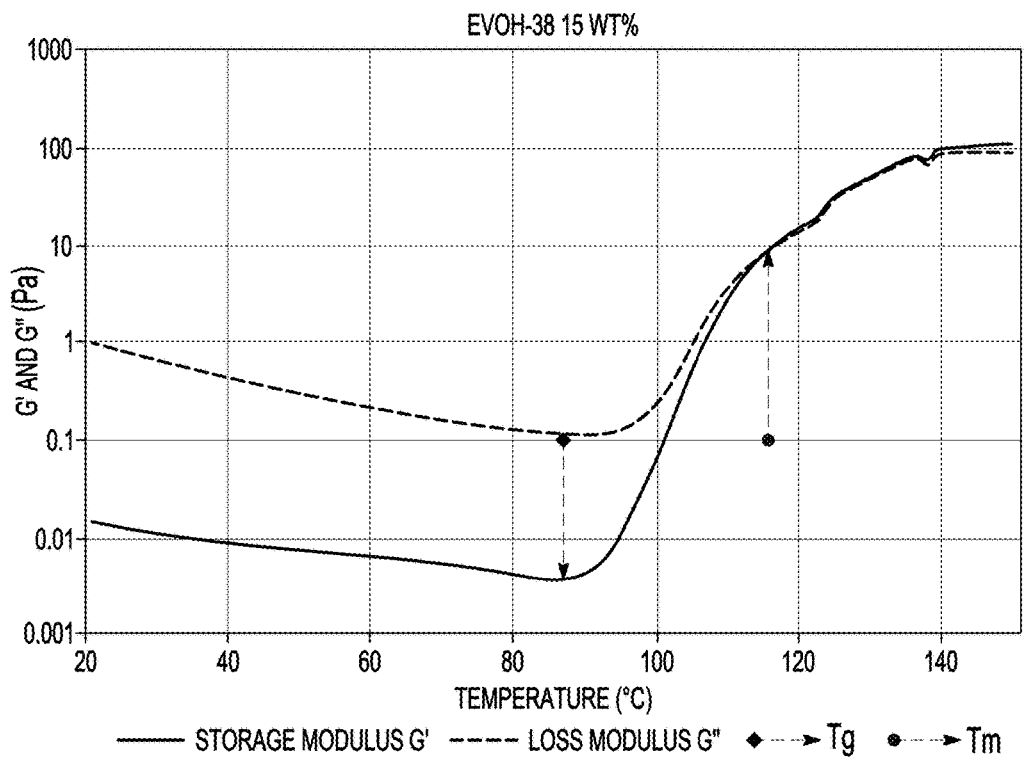

For EVOH 38-15% (FIG. 41), the melting temperature occurred at 116 degrees Celsius and the glass transition temperature occurred at 87 degrees Celsius. Compared to EVOH 32-15%, the melting point temperature decreased by 33 degrees Celsius and the glass transition temperature by 15 degrees Celsius. This comparison leads to the conclusion that for higher ethylene mol % of EVOH, the transition of the polymer solution from a solid state to a liquid/gel-like state occurs at a lower temperature.

Example 13

Hydrogel Swelling Studies

Figure 42:
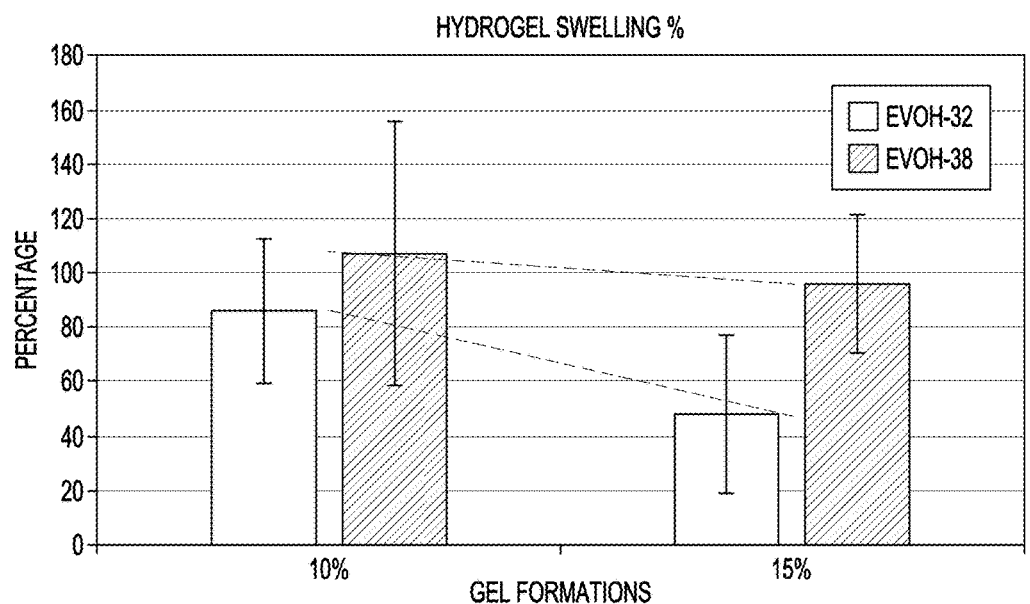
FIG. 42 is a graph showing mass percent swelling for select polymer candidates.
Figure 43:
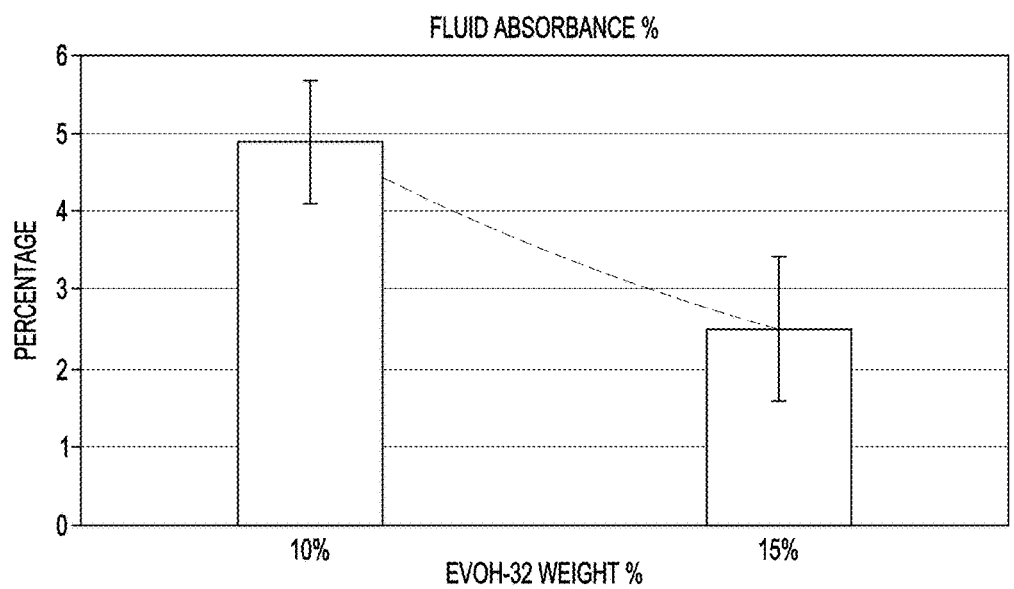
FIG. 43 is a graph showing percent fluid absorbance for select polymer candidates.

FIG. 42 represents the mass percent swelling of different polymer formulations in a proprietary media (hereby known as IVVM) simulating the human vas deferens environment by having the same osmolarity and pH. Mass percent swelling for each sample was measured by freeze-drying ten samples of cured polymer formed from a volume of 0.1 mL of resinous polymer, weighing these samples to determine an initial mass, exposing each of the samples to 1 mL of IVVM for three hours, and then reweighing to determine the final mass after swelling. Percent swelling was calculated as: % SW=((Mf−Mi)/Mi)*100. The results of this experiment suggest that percent swelling decreases as the weight percent of the polymer increases and that EVOH 38 has a higher percent mass swelling than EVOH 32. The fluid infiltration of EVOH 32-10% and EVOH 32-15% are shown in the graphs of FIG. 43.

Example 14

Degradation Studies

Figure 44:
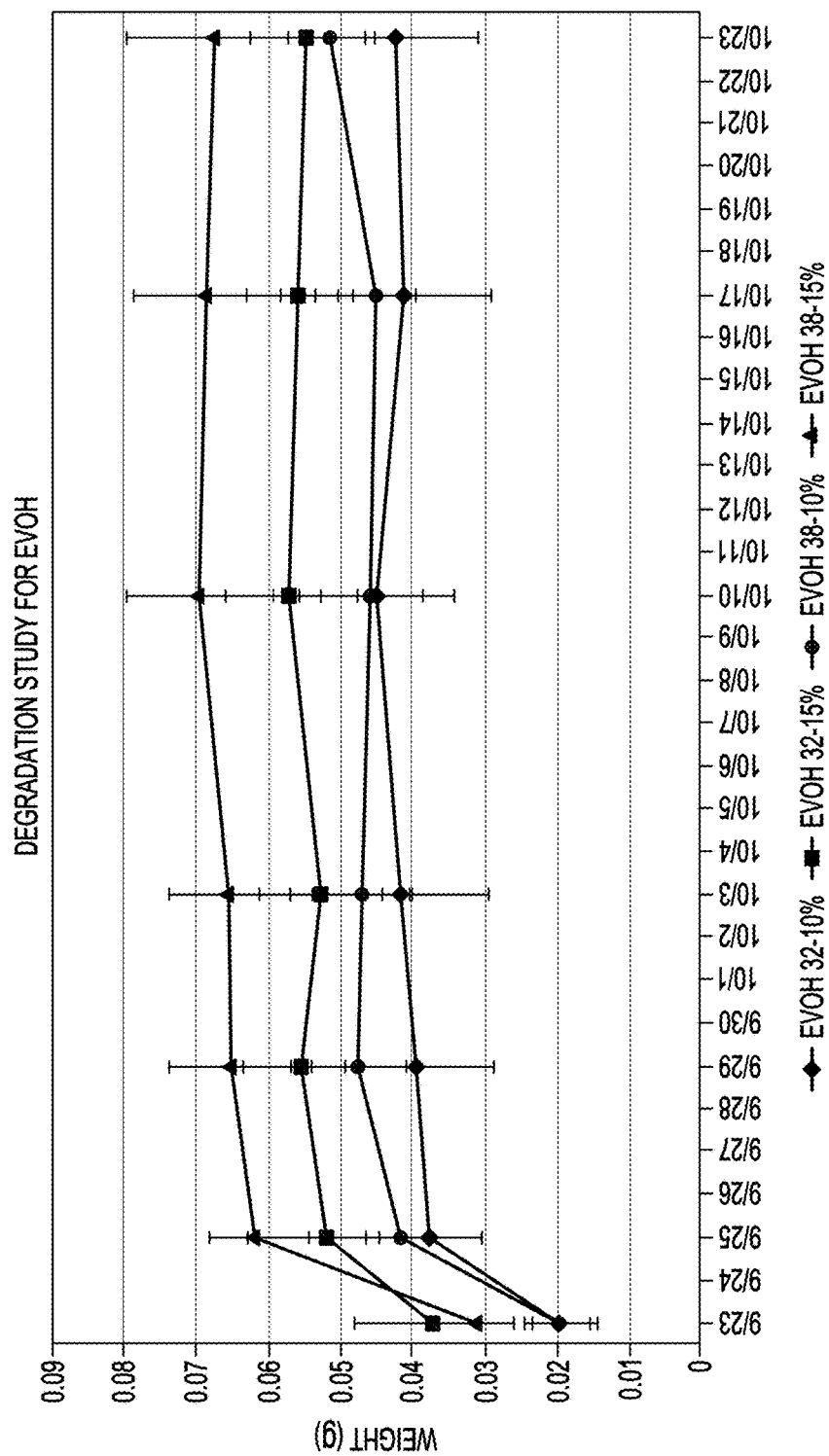
FIG. 44 is a graph showing the results of a degradation study for select EVOH polymer candidates. Mass is plotted on the y axis and date is plotted in the x axis.

FIG. 44 is a summary of the results of an accelerated aging study to assess the stability/durability of several different EVOH polymer formulations in vitro. The experiment has been designed to simulate the vas deferens microenvironment, which involves maintaining the hydrogels at the same temperature found in the vas deferens (35 degrees Celsius; slightly below body temperature) and in media consisting of the same osmolarity (ion concentrations) and pH. A proprietary media, coined in vitro vas media (IVVM), was used to simulate this environment. Samples were introduced to 1 mL of IVVM after being lyophilized (freeze-dried). Initial swelling has been observed for several formulations as the samples are re-hydrated. Degradation is being measured by weight % gain or loss over time.

Polymer gels with higher stability in a biological environment will show a slower rate of degradation (or mass % lost) when compared to other, degradable polymers. The results of this study demonstrate that all EVOH hydrogels are non-degradable for 1 month. The EVOH hydrogels swell to almost double their weight in the first two days. Their mass then remains steady for the remaining weeks. The results hold similar to the swelling study, where EVOH 38 has been shown to swell more than EVOH 32. However, in this degradation study, the 15 wt % EVOH gels swelled more than the 10 wt %.

Figure 45:
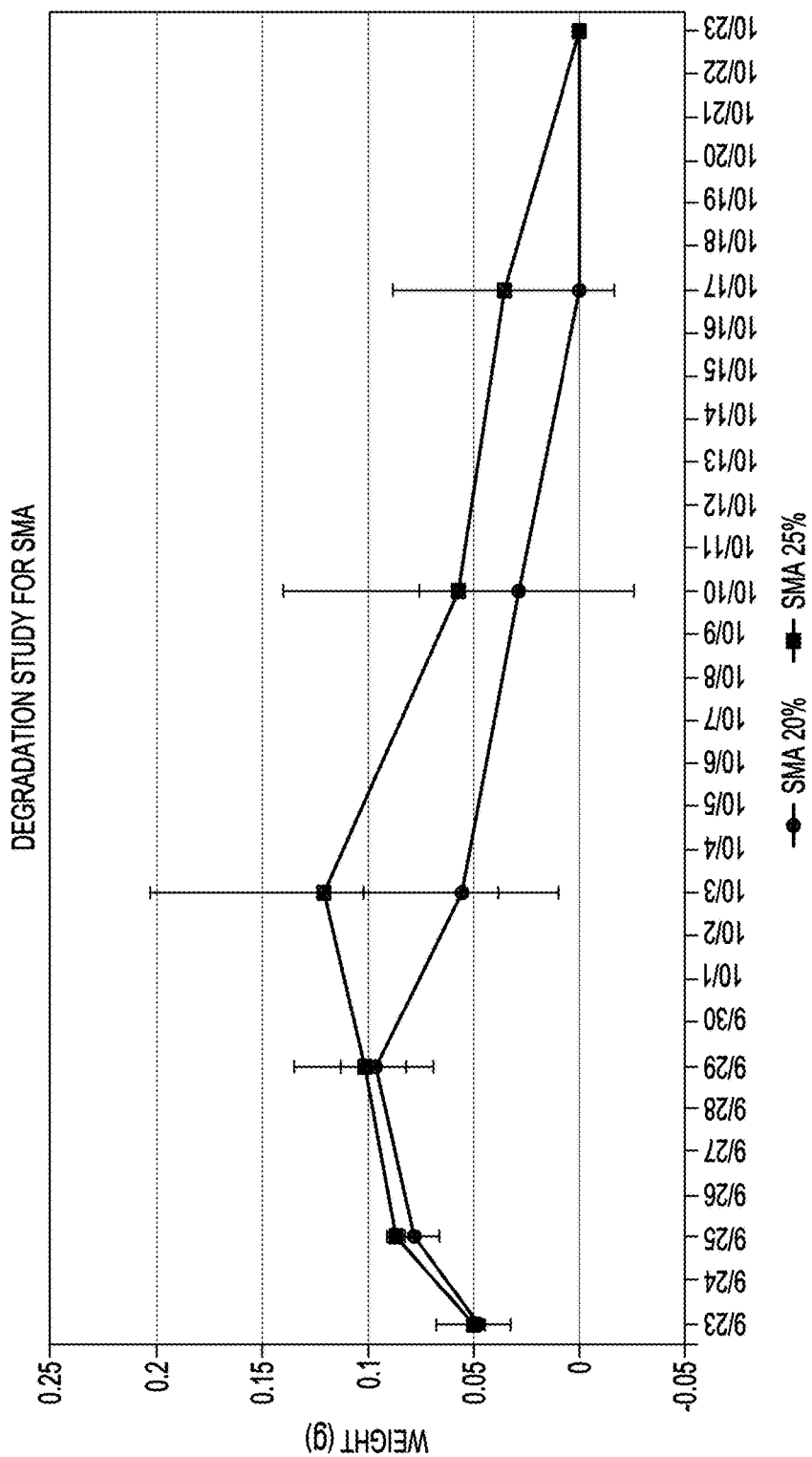
FIG. 45 is a graph showing the results of a degradation study for select SMA polymer candidates. Mass is plotted on the y axis and date is plotted in the x axis.

Unlike EVOH, SMA was highly degradable (FIG. 45). The polymer swelled for 6-10 days (depending on the wt %) and then began to degrade at 35 degrees C. and in vas-simulating media. It took 20-25 days for the SMA polymers to degrade. Thus, it is shown that SMA would not be a good candidate for long-term (>1 year) vas-occlusive contraception.

Example 15

Echogenicity

Formulations of ninety-six test gels were created within a 96-well plate and arranged in a Knox gelatin construct to compare the average echogenicity of the different compositions. Each well was filled with 0.5 mL of gel solution and was then exposed to 1.5 mL of DI water. The mixture was given a quick stir to ensure that the gel solutions had full contact with water and were allowed to precipitate and harden. The Knox gelatin was created according to the manufacturer recommended water-powder ratio. Eight technical replicates were performed for each of the twelve formulations, and each gel was imaged in five different locations throughout their length to average out non-homogenous sections. The gels were imaged with an Ezono 4000 ultrasound using a linear transducer in "general" focus and "high" frequency settings.

Figure 46:
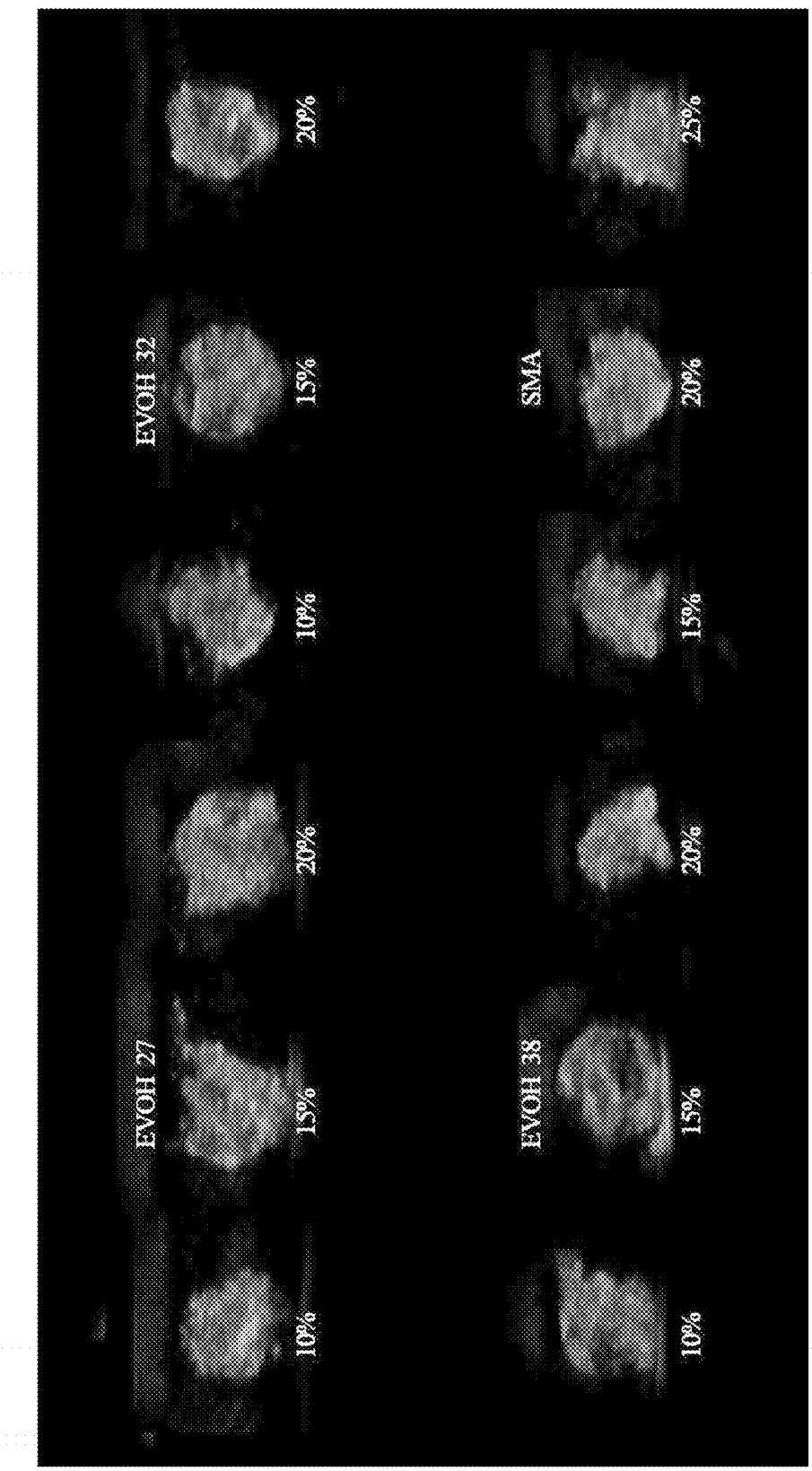
FIG. 46 is an array of ultrasound images showing axial cross-sections of select polymer gel candidates.
Figure 47C:
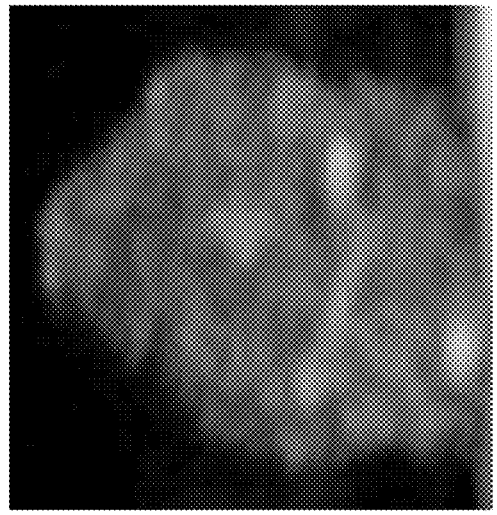
FIGS. 47A-47C are ultrasound images showing three of the EVOH 32 gels in an expanded view.
Figure 47B:
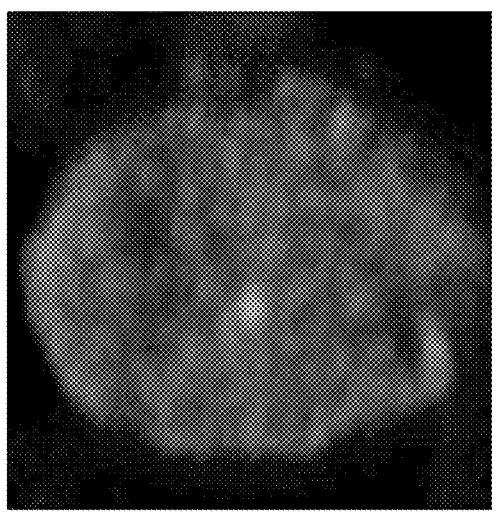
Figure 47A:
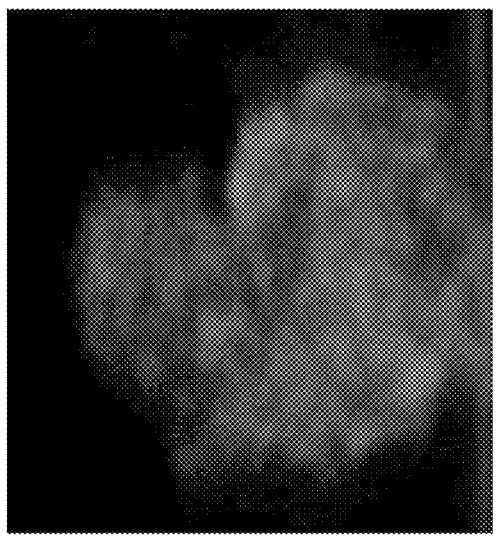

FIG. 46 shows axial cross-sections of representative gels. The brightness of these gels relative to the background would be the metric for how ultrasound visible they would be within the body during the VASINTOMY™ procedure. FIGS. 47A-47C show three of the EVOH 32 gels in an expanded view.

Figure 48:
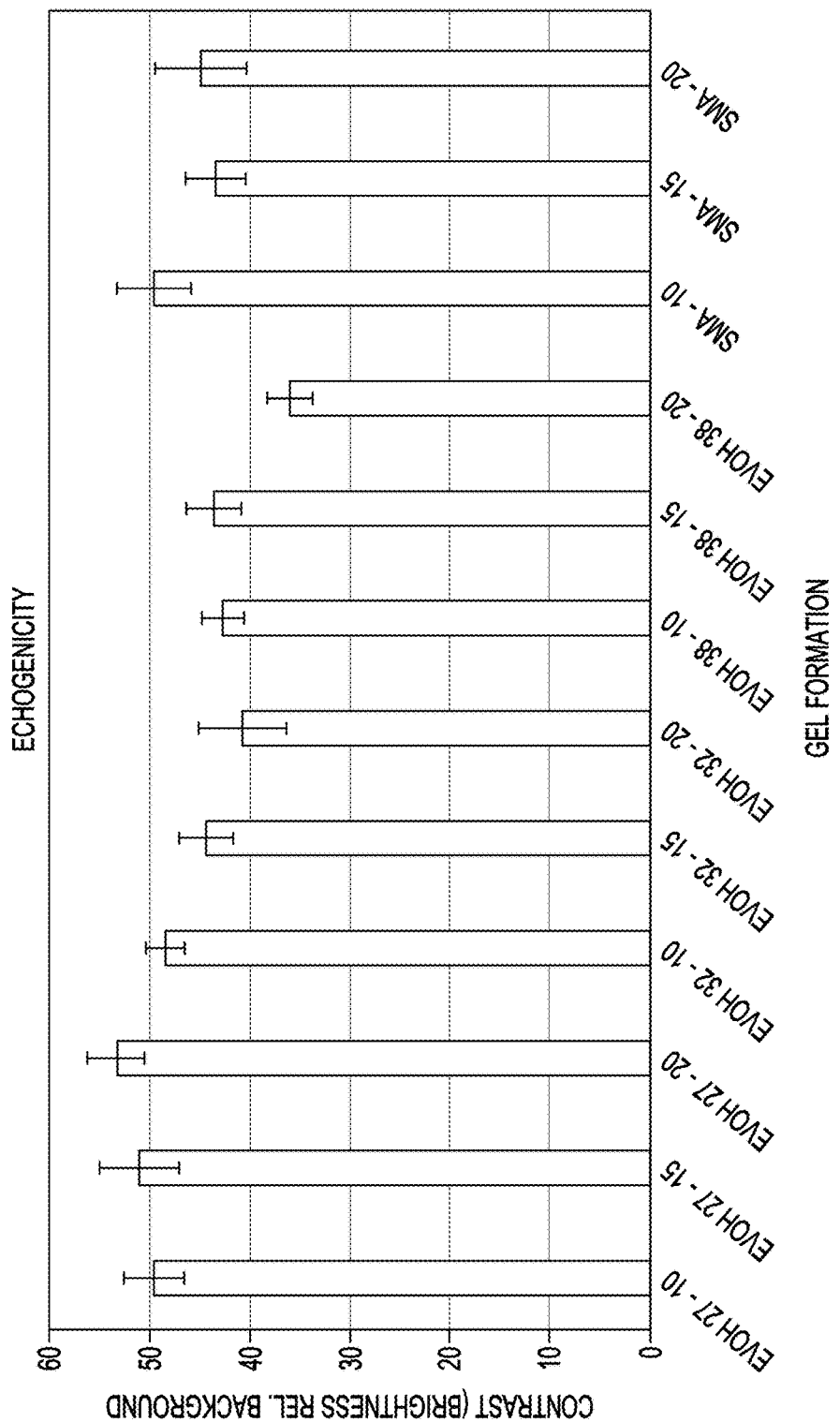
FIG. 48 is a graph showing an average pixel brightness and standard deviation of ultrasound images for select polymer candidates.

The entirety of the gel within each image was traced out on ImageJ and an average pixel brightness of that image was recorded. This value would be averaged with the other four images from that gel to ensure a representative brightness value. This process was repeated for each replicate and an average brightness and standard deviation for each gel formulation was generated. The results are shown in the graph in FIG. 48.

From this data, it can be seen that EVOH 27 was more echogenic than EVOH 32 and EVOH 38. There was not a clear pattern in increase in echogenicity based on weight %. All gels were strongly contrasted with the background (>35 brightness) and would easily be distinguished from the lumen of the vas using ultrasound.

Example 16

Ultrasound Imaging of Ethylene Vinyl Alcohol Gels with and without Microbubbles

Figure 17A:
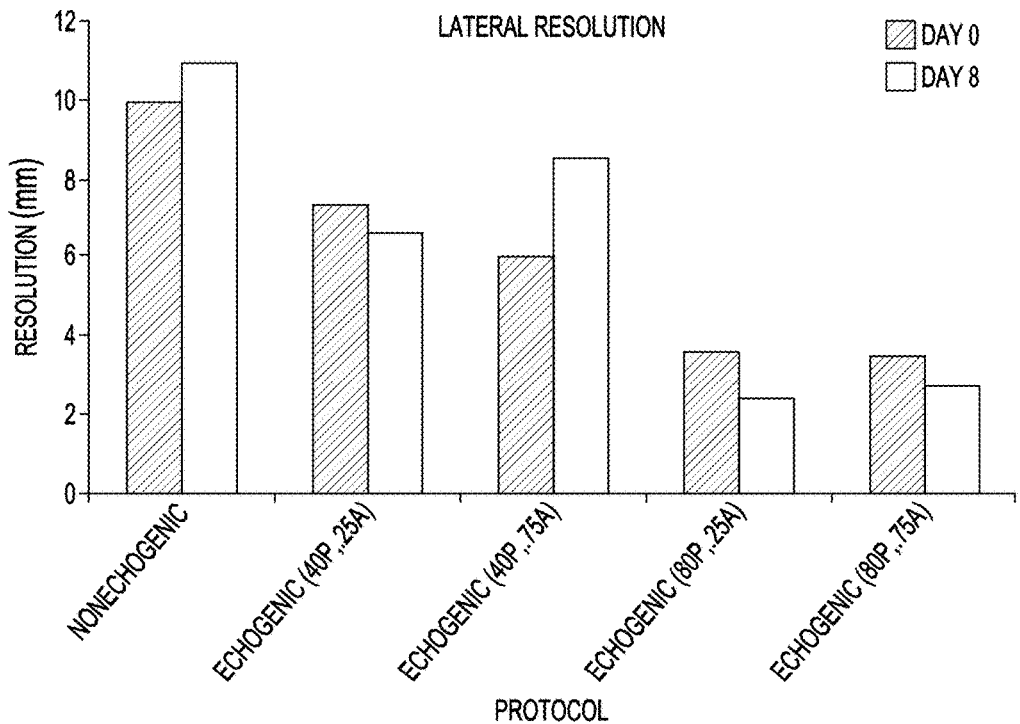
FIGS. 17A and 17B are graphs showing lateral (FIG. 17A) and axial (FIG. 17B) resolutions of various echogenic EVOH gel images.
Figure 17B:
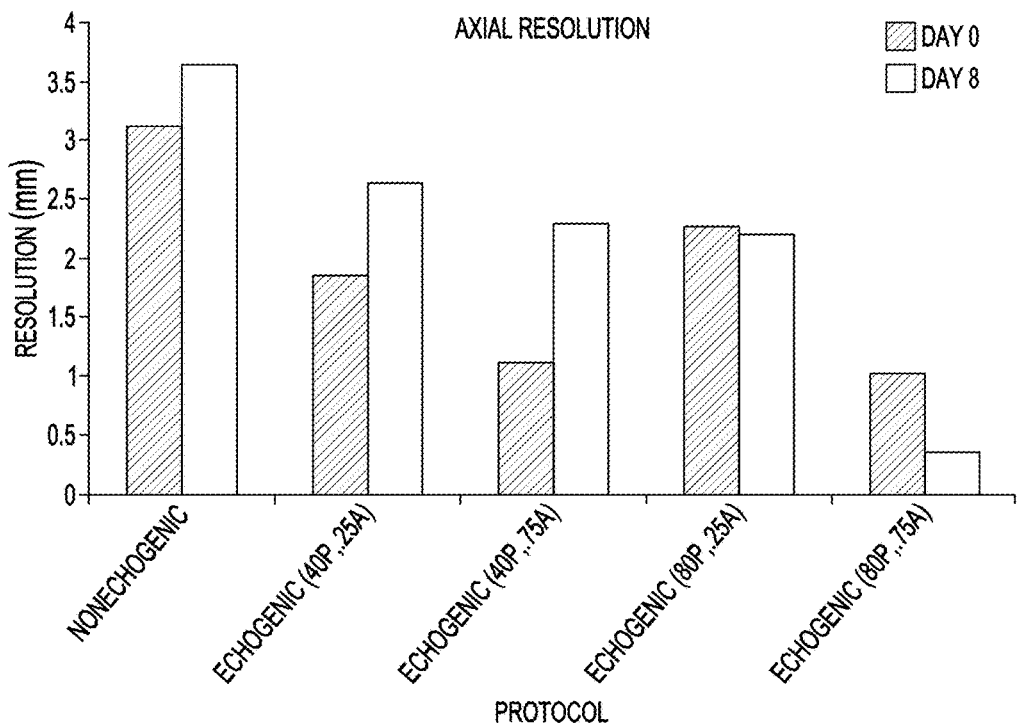

Gels were precipitated in a cuvette filled with water-based ultrasound gel. The gels were 10% EVOH (32% ethylene content) in DMSO. Full-width half-maximum resolution was calculated for images taken. Lateral and axial resolution of imaged gels from varied double syringe agitation protocols (1 week trial). Double syringe agitation was performed using EVOH 32-10% by varying the # of pumps (40 or 80) and volume of air introduced (0.25 mL or 0.75 mL). The gels were precipitated in a cuvette with ultrasound goo and the full-width half-maximum resolution was calculated for the ultrasound images taken. Lateral (FIG. 17A) and Axial (FIG. 17B) resolutions of various echogenic EVOH gel images at Day 0 and Day 8 (n=1) are shown, with P=plunges and A=mL of air introduced to double syringe system.

In general, the higher the resolution, the lower the echogenicity. Thus, the non-echogenic gels had lower longitudinal and axial echogenicity than the gels containing air microbubbles formed by agitation. Furthermore, the echogenicity increased with increased # of pumps. The amount of air introduced did not significantly increase the echogenicity. In most cases, the polymer lost echogenicity after 8 days in the cuvette. However, the echogenic gels formed with 80 pumps increased in echogenicity from day 0 to day 8.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" or "including" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. Further, the ranges of values disclosed in this specification are not limited to those explicitly disclosed but can include any value recited in this specification as an upper or lower limit. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure, including patents, published applications, and non-patent literature are each individually incorporated by reference herein in their entireties and as such are intended to provide an efficient way of supplementing the enabling disclosure of this invention as well as provide background detailing the level of ordinary skill in the art.

What is claims is:

1. A method. of occluding an animal or human body lumen comprising:
   puncturing the body lumen using a needle;
   administering a first and second substance into the body lumen; and forming a mass in the body lumen by having the first and second substances crosslink with each other by way of a bioorthogonal reaction, wherein as a result of crosslinking an occlusion is formed in situ in the body lumen; and
   wherein a plurality of pores having an average pore size in the range of about 0.1 nm to about 3 μm are formed in the occlusion from interaction between the first and second substances.

2. The method of claim 1, wherein the occlusion is echogenic.

3. The method of claim 2, wherein microbubbles are present in the first and/or second substances and are encapsulated in the occlusion and the microbubbles have an average size in the range from about 1 to about 1,000 μm in diameter.

4. The method of claim 3, wherein the microbubbles have a shell comprising a polymer, a protein, a surfactant, a monosaccharide, a polysaccharide, or glass.

5. The method of claim 4, wherein the polymer comprises one or more of natural or synthetic monomers, polymers, copolymers or block copolymers, biocompatible monomers, polymers, copolymers or block copolymers, polystyrene, neoprene, polyetherether 10ketone (PEEK), carbon reinforced PEEK, polyphenylene, PEKK, PAEK, polyphenylsulphone, polysulphone, PET, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, TEFLON® TFE, polyethylene terephthalate (PETE), TEFLON® FEP, TEFLON® PFA, and/or polymethylpentene (PMP) styrene maleic anhydride, styrene maleic acid, polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamine) (PNIPAM), poly (vinylmethylether), poly (ethylene oxide), poly (ethyl (hydroxyethyl) cellulose), poly(2-ethyl oxazoline), polylactide (PLA), polyglycolide (PGA), poly(lactide-co-glycolide) PLGA, poly(e-caprolactone), polydiaoxanone, polyanhydride, trimethylene carbonate, poly(β-ydroxybutyrate), poly (g-ethyl glutamate), poly(DTH-iminocarbonate), poly(bisphenol A iminocarbonate), poly(orthoester) (POE), polycyanoacrylate (PCA), polyphosphazene, polyethyleneoxide (PEO), polyethylene glycol (PEG), polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly(vinyl alcohol) (PVOH), PEG diacrylate (PEGDA), poly(hydroxyethyl methacrylate) (pHEMA), N-isopropylacrylamide (NIPA), poly(vinyl alcohol) poly (acrylic acid) (PVOH-PAA), collagen, silk, fibrin, gelatin, hyaluron, cellulose, chitin, dextran, casein, albumin, ovalbumin, heparin sulfate, starch, agar, heparin, alginate, fibronectin, fibrin, keratin, pectin, elastin, ethylene vinyl acetate, polyethylene oxide, PEG or any of its derivatives, PLLA, PDMS, PIPA, PEVA, PILA, PEG styrene, Teflon RFE, FLPE, Teflon FEP, methyl palmitate, NIPA, polycarbonate, polyethersulfone, polycaprolactone, polymethyl methacrylate, polyisobutylene, nitrocellulose, medical grade silicone, cellulose acetate, cellulose acetate butyrate, polyacrylonitrile, PLCL, and/or chitosan.

6. The method of claim 1, whereby a hydrogel occlusion is formed.

7. The method of claim 6, wherein the first and/or second substance is a solution and the hydrogel occlusion is formed in situ and once formed comprises a plurality of pores sized to restrict passage of sperm cells but permit passage of fluids through the pores.

8. The method of claim 1, wherein the first and the second substance crosslink with each other by way of a Click reaction.

9. The method of claim 8, wherein the first substance and the second substance are each a polymer chosen from one or more of natural or synthetic monomers, polymers, copolymers or block copolymers, biocompatible monomers, polymers, copolymers or block copolymers, polystyrene, neoprene, polyetherether 10 ketone (PEEK), carbon reinforced PEEK, polyphenylene, PEKK, PAEK, polyphenylsulphone, polysulphone, PET, polyurethane, polyethylene, low-density polyethylene (LDPE), linear low-density polyethylene (LLDPE), high-density polyethylene (HDPE), polypropylene, polyetherketoneetherketoneketone (PEKEKK), nylon, TEFLON® TFE, polyethylene terephthalate (PETE), TEFLON® FEP, TEFLON® PFA, and/or polymethylpentene (PMP) styrene maleic anhydride, styrene maleic acid, polyurethane, silicone, polymethyl methacrylate, polyacrylonitrile, poly (carbonate-urethane), poly (vinylacetate), nitrocellulose, cellulose acetate, urethane, urethane/carbonate, polylactic acid, polyacrylamide (PAAM), poly (N-isopropylacrylamine) (PNIPAM), poly (vinylmethylether), poly (ethylene oxide), poly (ethyl (hydroxyethyl) cellulose), poly(2-ethyl oxazoline), polylactide (PLA), polyglycolide (PGA), poly(lactide-co-glycolide) PLGA, poly(e-caprolactone), polydiaoxanone, polyanhydride, trimethylene carbonate, poly(β-hydroxybutyrate), poly(g-ethyl glutamate), poly (DTH-iminocarbonate), poly(bisphenol A iminocarbonate), poly(orthoester) (POE), polycyanoacrylate (PCA), polyphosphazene, polyethyleneoxide (PEO), polyethylene glycol (PEG), polyacrylacid (PAA), polyacrylonitrile (PAN), polyvinylacrylate (PVA), polyvinylpyrrolidone (PVP), polyglycolic lactic acid (PGLA), poly(2-hydroxypropyl methacrylamide) (pHPMAm), poly(vinyl alcohol) (PVOH), PEG diacrylate (PEGDA), poly(hydroxyethyl methacrylate) (pHEMA), N-isopropylacrylamide (NIPA), poly(vinyl alcohol) poly(acrylic acid) (PVOH-PAA), collagen, silk, fibrin, gelatin, hyaluron, cellulose, chitin, dextran, casein, albumin, ovalbumin, heparin sulfate, starch, agar, heparin, alginate, fibronectin, fibrin, keratin, pectin, elastin, ethylene vinyl acetate, polyethylene oxide, PEG or any of its derivatives, PLLA, PDMS, PIPA, PEVA, PILA, PEG styrene, Teflon RFE, FLPE, Teflon FEP, methyl palmitate, NIPA, polycarbonate, polyethersulfone, polycaprolactone, polymethyl methacrylate, polyisobutylene, nitrocellulose, medical grade silicone, cellulose acetate, cellulose acetate butyrate, polyacrylonitrile, PLCL, and/or chitosan, wherein the first substance comprises a thiol end group and the second substance comprises a maleimide end group.

10. The method of claim 1, wherein imaging is used to identify the animal or human body lumen during and/or after forming the mass.

11. The method of claim 1, wherein the occlusion comprises a plurality of pores sized to restrict passage of sperm cells, but the occlusion absorbs and allows passage of fluids through.

12. The method of claim 1, wherein the first and second substance each have a viscosity less than or equal to 7 Pa*s.

13. The method of claim 1, wherein the first and/or second substance includes one or more of a contraceptive, an occlusive device, a therapeutic agent, an imaging agent, an echogenic agent, microbubbles, spermicide, antimicrobials, vasodilators, and/or a composition or device for increasing or decreasing motility, viability, and/or fertility of sperm or ova.

14. The method of claim 1, wherein the first and/or second substance comprises an imaging agent.

15. The method of claim 1, wherein the body lumen is chosen from one or more of a vas deferens, fallopian tube, aneurysm, blood vessel, ducts, tumors, and organs.

16. The method of claim 1, wherein after the occlusion is formed, the occlusion swells to secure itself within the body lumen.

17. The method of claim 1, wherein the occlusion is formed within 10 minutes.

18. A method of occluding a body lumen comprising:
imaging a body lumen with ultrasound;
injecting a first composition and a second composition into the body lumen; and
allowing the first and second compositions to crosslink with each other by way of a bioorthogonal reaction to form a mass in the body lumen;
wherein, as a result of the crosslinking, a plurality of pores having an average pore size of 3µm or less are formed in the mass from interaction between the first and second compositions.

19. The method of claim 18, wherein the body lumen is chosen from one or more of a vas deferens, fallopian tube, aneurysm, blood vessel, ducts, tumors, and organs.

20. The method of claim 19, wherein the body lumen is a vas deferens.

21. The method of claim 18, wherein the first and/or second composition before the crosslinking has a viscosity in the range of about 1 to 7 Pa*s.

22. A method of occluding an animal or human vas deferens lumen comprising:
puncturing the vas deferens lumen using a needle;
administering a first and second substance into the vas deferens lumen; and
forming a mass in the vas deferens lumen by having the first and second substances crosslink with each other by way of a bioorthogonal reaction; and
performing at least one of the following steps under ultrasound imaging:
percutaneously placing a needle or catheter or portion thereof into the vas deferens lumen;
administering the first and second substance into the vas deferens lumen through the needle or catheter;
confirming formation of the occlusion inside the vas deferens lumen;
determining one or more dimensions of the occlusion inside the vas deferens lumen.

23. The method of claim 22, wherein at least two steps are performed under ultrasound imaging.

24. The method of claim 22, wherein at least three steps are performed under ultrasound imaging.

25. A method of removing an occlusion disposed in a body lumen, comprising:
imaging a body lumen and an occlusion disposed therein using ultrasound imaging, wherein the occlusion is formed from:
puncturing an animal or human body lumen using a needle;
administering a first and second substance into the body lumen; and
forming a mass in the body lumen by having the first and second substances crosslink with each other by way of a bioorthogonal reaction;
performing one or more or all of the following:
administering a substance into the body lumen and allowing the substance to deteriorate, break down, degrade, disintegrate, reverse, dissolve, destroy, remove, dislodge, de-precipitate, liquefy, flush and/or reduce the occlusion in whole or part; and/or
administering ultrasonic energy to the occlusion at an intensity and/or frequency capable of deteriorating, breaking down, degrading, disintegrating, reversing, dissolving, destroying, removing, dislodging, de-precipitating, liquefying, flushing and/or reducing the occlusion in whole or part; and
confirming a change associated with durability, longevity, or placement of the occlusion using ultrasound imaging.

26. The method of claim 25, wherein the body lumen is chosen from one or more of a vas deferens, fallopian tube, aneurysm, blood vessel, ducts, tumors, and organs.

* * * * *